(12) United States Patent
Taylor et al.

(10) Patent No.: US 8,889,595 B2
(45) Date of Patent: Nov. 18, 2014

(54) HERBICIDES

(75) Inventors: John Benjamin Taylor, Bracknell (GB);
Jeffrey Steven Wailes, Bracknell (GB);
Stephane André Marie Jeanmart, Stein (CH); Mangala Govenkar, Ilhas Goa (IN)

(73) Assignees: Syngenta Participations AG, Basel (CH); Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/139,432

(22) PCT Filed: Dec. 9, 2009

(86) PCT No.: PCT/EP2009/066712
§ 371 (c)(1),
(2), (4) Date: Oct. 25, 2011

(87) PCT Pub. No.: WO2010/069834
PCT Pub. Date: Jun. 24, 2010

(65) Prior Publication Data
US 2012/0065064 A1  Mar. 15, 2012

(30) Foreign Application Priority Data
Dec. 15, 2008  (GB) .................... 0822834.8

(51) Int. Cl.
*A01N 43/60* (2006.01)
*A61K 31/54* (2006.01)

(52) U.S. Cl.
USPC ................ 504/235; 514/222.2; 585/100

(58) Field of Classification Search
USPC ................ 585/100; 504/235; 514/222.2
See application file for complete search history.

(56) References Cited

U.S. PATENT DOCUMENTS

| | | | |
|---|---|---|---|
| 4,338,122 A | 7/1982 | Wheeler | |
| 4,409,153 A | 10/1983 | Hodakowski | |
| 4,526,723 A | 7/1985 | Wheeler et al. | |
| 4,551,547 A | 11/1985 | Wheeler | |
| 5,684,205 A | 11/1997 | Norman et al. | |
| 5,808,135 A | 9/1998 | Fischer et al. | |
| 5,840,661 A | 11/1998 | Fischer et al. | |
| 6,251,833 B1 | 6/2001 | Erdelen et al. | |
| 6,358,887 B1 | 3/2002 | Fischer et al. | |
| 6,458,965 B1 | 10/2002 | Lieb et al. | |
| 6,515,184 B1 | 2/2003 | Fischer et al. | |
| 6,642,180 B1 | 11/2003 | Fischer et al. | |
| 6,894,005 B1 | 5/2005 | Maetzke et al. | |
| 2003/0216260 A1 | 11/2003 | Ruther et al. | |
| 2005/0054535 A1 | 3/2005 | Fischer et al. | |
| 2006/0058194 A1 | 3/2006 | Fischer et al. | |
| 2006/0166829 A1 | 7/2006 | Fischer et al. | |
| 2007/0015664 A1 | 1/2007 | Fischer et al. | |
| 2007/0298698 A1 | 12/2007 | Ali et al. | |
| 2007/0398698 | 12/2007 | Terry et al. | |
| 2009/0137393 A1 | 5/2009 | Fischer et al. | |
| 2009/0227563 A1 | 9/2009 | Fischer et al. | |
| 2009/0239906 A1 | 9/2009 | Fischer et al. | |
| 2009/0298828 A1 | 12/2009 | Fischer et al. | |
| 2009/0305891 A1 | 12/2009 | Fischer et al. | |
| 2011/0263428 A1 | 10/2011 | Jeanmart et al. | |
| 2012/0021912 A1 | 1/2012 | Mathews et al. | |
| 2012/0028800 A1 | 2/2012 | Mathews et al. | |
| 2012/0094832 A1 | 4/2012 | Tyte et al. | |
| 2012/0142529 A1 | 6/2012 | Tyte et al. | |
| 2012/0178623 A1 | 7/2012 | Foley et al. | |

FOREIGN PATENT DOCUMENTS

| | | |
|---|---|---|
| CA | 2322158 A1 | 8/2000 |
| CA | 2456776 A1 | 2/2004 |
| CA | 2636352 A1 | 7/2008 |
| EP | 0701988 A1 | 3/1996 |
| WO | 9601798 A1 | 1/1996 |
| WO | 9603366 A1 | 2/1996 |
| WO | 9625395 A1 | 8/1996 |
| WO | 9635664 A1 | 11/1996 |
| WO | 9839281 A1 | 9/1998 |
| WO | 9943649 A1 | 9/1999 |
| WO | 9948869 A1 | 9/1999 |
| WO | 0109092 A1 | 2/2001 |
| WO | 0117972 A2 | 3/2001 |
| WO | 2001074770 A1 | 10/2001 |
| WO | 0313249 A1 | 2/2003 |
| WO | 03013249 | 2/2003 |
| WO | 2004037749 A2 | 5/2004 |

(Continued)

OTHER PUBLICATIONS

Wermuth, C.G.: "Molecular variations based on isosteric replacements", Practice of Medicinal Chemistry, Jan. 1, 1996, pp. 203-237.
M. Muchlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

(Continued)

*Primary Examiner* — Paul V. Ward
(74) *Attorney, Agent, or Firm* — R. Kody Jones

(57) ABSTRACT

Compounds of the formula (I) wherein the substituents are as defined in claim 1, are suitable for use as herbicides.

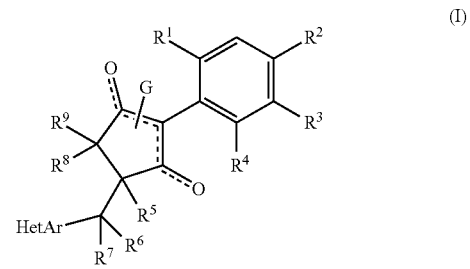

(I)

18 Claims, No Drawings

(56) References Cited

FOREIGN PATENT DOCUMENTS

| WO | 2004080962 A1 | 9/2004 |
| WO | 2004111042 A1 | 12/2004 |
| WO | 2005092897 A2 | 10/2005 |
| WO | 2007068427 A2 | 6/2007 |
| WO | 2007080066 | 7/2007 |
| WO | 2007080066 A2 | 7/2007 |
| WO | 2007096058 A1 | 8/2007 |
| WO | 2007121868 A1 | 11/2007 |
| WO | 2007140881 A1 | 12/2007 |
| WO | 2008071405 A1 | 6/2008 |
| WO | 2008110307 A1 | 9/2008 |
| WO | 2008110308 A2 | 9/2008 |
| WO | 2008145336 A1 | 12/2008 |
| WO | 2010000773 | 1/2010 |

OTHER PUBLICATIONS

J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

J. Wenger, T. Nidermann and C. Mathews, "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

Wermuth, C.G., "Molecular variations based on isosteric replacements," Practice of Medicinal Chemistry, XX, Jan. 1, 1996, p. 203-236.

HERBICIDES

This application is a 371 of International Application No. PCT/EP2009/066712 filed Dec. 9, 2009, which claims priority to GB 0822834.8 filed Dec. 15, 2008, the contents of which are incorporated herein by reference.

The present invention relates to novel, herbicidally active cyclopentanedione compounds, and derivatives thereof, to processes for their preparation, to compositions comprising those compounds, and to their use in controlling weeds, especially in crops of useful plants, or in inhibiting undesired plant growth.

Cyclopentanedione compounds having herbicidal action are described, for example, in WO 01/74770 and WO 96/03366.

Novel cyclopentanedione, and derivatives thereof, having herbicidal and growth-inhibiting properties have now been found.

The present invention accordingly relates to compounds of formula I

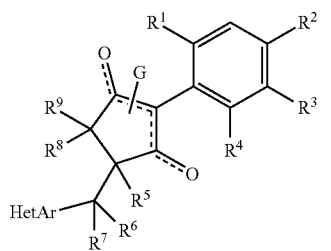

wherein
G is hydrogen or an agriculturally acceptable metal, sulfonium, ammonium or latentiating group,
$R^1$ is methyl, ethyl, n-propyl, isopropyl, cyclopropyl, halomethyl, haloethyl, vinyl, ethynyl, halogen, $C_1$-$C_2$alkoxy or $C_1$-$C_2$haloalkoxy,
$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, $C_1$-$C_2$alkoxy, $C_1$-$C_2$haloalkoxy, optionally substituted aryl or optionally substituted heteroaryl,
$R^4$ is hydrogen, methyl, ethyl, n-propyl, isopropyl, cyclopropyl, halomethyl, haloethyl, vinyl, propenyl, ethynyl, propynyl, halogen, $C_1$-$C_2$alkoxy or $C_1$-$C_2$haloalkoxy,
$R^5$, $R^6$, $R^7$, $R^8$ and $R^9$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$ haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$ cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or
$R^6$ and $R^7$ or $R^8$ and $R^9$ together with the carbon atoms to which they are attached form an optionally substituted carbocyclic ring or an optionally substituted heterocyclyl, or $R^5$ and $R^6$ together form a bond, and
HetAr is an heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

In the substituent definitions of the compounds of the formula I, each alkyl moiety either alone or as part of a larger group (such as alkoxy, alkylthio, alkylsulfinyl and alkylsulfonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxy-carbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio (where the aryl group is optionally substituted), $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio (where the aryl group is optionally substituted), $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl (where the aryl group is optionally substituted), tri($C_1$-$C_4$)alkylsilyl, aryldi($C_1$-$C_4$)alkylsilyl, ($C_1$-$C_4$)alkyldiarylsilyl, triarylsilyl, aryl($C_1$-$C_4$)alkylthio($C_1$-$C_4$)alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di(C1-C6 alkyl)aminocarbonyl, N-($C_1$-$C_3$alkyl)-N-($C_1$-$C_3$alkyl)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N-($C_1$-$C_6$)alkylcarbonyl-N-($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono-, bi- or tricyclic. Examples of such rings include phenyl, naphthyl, anthracenyl, indenyl or phenanthrenyl. A preferred aryl group is phenyl.

The term "heteroaryl" or "HetAr" preferably refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

Preferred examples of heteroaryls include 5-membered rings which are optionally benzannellated, such as thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl and benzisoxazolyl. These rings are optionally substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

Another group of preferred heteroaryls includes 6-membered rings which are optionally benzannellated, such as pyridyl, pyrimidinyl, pyridazinyl, quinolinyl, isoquinolinyl, cinnolinyl, phthalazinyl, quinazolinyl and quinoxalinyl. These rings are optionally substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, morpholine, thiomorpholin and piperazine. When present, the optional substituents on heterocyclyl include $C_1$-$C_6$alkyl and $C_1$-$C_6$haloalkyl as well as those optional substituents given above for an alkyl moiety.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl. When present, the optional substituents on cycloalkyl or cycloalkenyl include $C_1$-$C_3$alkyl as well as those optional substituents given above for an alkyl moiety.

Carbocyclic rings include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$) alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$) alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N-($C_1$-$C_3$alkyl)-N-($C_1$-$C_3$alkoxy)aminocarbonyl, $C_1$-$C_6$alkylcarbonyloxy, arylcarbonyloxy, di($C_1$-$C_6$) alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N-($C_1$-$C_6$)alkylcarbonyl-N-($C_1$-$C_6$)alkylamino, arylcarbonyl, (where the aryl group is itself optionally substituted with halogen or $C_1$-$C_6$alkyl) or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N-($C_1$-$C_6$)alkylamino, aryloxycarbonylamino (where the aryl group is substituted by $C_1$-$C_6$alkyl or halogen), aryloxycarbonyl-N-($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N-($C_1$-$C_6$)alkylamino (where the aryl group is substituted by $C_1$-$C_6$alkyl or halogen), aryl-N-($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino where the aryl group is substituted by $C_1$-$C_6$alkyl or halogen), aryl-N-($C_1$-$C_6$)alkylaminocarbonylamino where the aryl group is substituted by $C_1$-$C_6$alkyl or halogen), $C_1$-$C_6$alkylaminocarbonyl-N-$C_1$-$C_6$)alkylamino, di($C_1$-$C_6$) alkylaminocarbonyl-N-$C_1$-$C_6$)alkylamino, arylaminocarbonyl-N-($C_1$-$C_6$)alkylamino where the aryl group is substituted by $C_1$-$C_6$alkyl or halogen) and aryl-N-$C_1$-$C_6$)alkylaminocarbonyl-N-$C_1$-$C_6$)alkylamino where the aryl group is substituted by $C_1$-$C_6$alkyl or halogen).

For substituted heterocyclyl groups it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexyl-amine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a$$R_b$$R_c$$R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e$$R_f$$R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl $C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl $C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N($R^c$)—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-($C_1$-$C_5$)oxyalkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl ($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkyl-carbonyl-N-($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio ($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl ($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkyl-carbonyl-N-($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl $C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio ($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl ($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkyl-carbonyl-N-($C_2$-$C_5$)alkylaminoalkyl, $C_3$-$C_6$-trialkylsilyl ($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio ($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl ($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkyl-carbonyl-N-($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio ($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl ($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkyl-carbonyl-N-($C_2$-$C_5$)alkylaminoalkyl, $C_3$-$C_6$-trialkylsilyl ($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N-($C_1$-$C_5$)alkylcarbonyl-N-($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy ($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula I may exist in different isomeric forms. When G is hydrogen, for example, compounds of formula I may exist in different tautomeric forms:

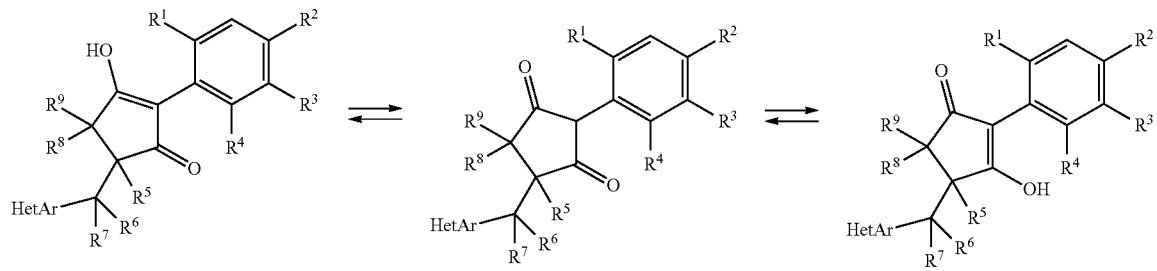

This invention covers all such isomers and tautomers and mixtures thereof in all proportions. Also, when substituents contain double bonds, cis- and trans-isomers can exist. These isomers, too, are within the scope of the claimed compounds of the formula I.

For the purpose of clarity, a compound of formula I, wherein G is H, is represented as a single tautomer, even if it is present in a different tautomeric form or as a mixture of tautomeric forms.

Preferably, in the compounds of the formula I, $R^1$ is methyl, ethyl, n-propyl, vinyl, ethynyl, halogen, $C_1$-$C_2$alkoxy or $C_1$-$C_2$haloalkoxy, especially methyl, $R^2$ is methyl, halogen, $C_1$-$C_2$alkoxy or $C_1$-$C_2$haloalkoxy, or optionally substituted phenyl, especially methyl, $R^3$ is hydrogen, and $R^4$ is methyl, ethyl, n-propyl, vinyl, ethynyl or methoxy, $R^5$, $R^6$, $R^7$, $R^8$ and $R^9$ are independently hydrogen, halogen, $C_1$-$C_4$alkyl, $C_1$-$C_4$haloalkyl, $C_1$-$C_4$alkoxy, $C_1$-$C_4$haloalkoxy, $C_2$-$C_4$alkenyl, $C_2$-$C_4$haloalkenyl, $C_2$-$C_4$alkynyl, $R^6$ and $R^7$ or $R^8$ and $R^9$ together with the carbon atoms to which they are attached form an optionally substituted carbocyclic ring or an optionally substituted heterocyclyl, or $R^5$ and $R^6$ together form a bond, and HetAr is heteroaryl or heteroaryl substituted one to three times by fluoro, chloro, bromo, methyl, methoxy, cyano or trifluoromethyl.

More preferably,
R¹ is methyl or ethyl, R² is methyl or chloro, R³ is hydrogen, R⁴ is methyl, ethyl or methoxy, R⁵,
R⁶, R⁷, R⁸ and R⁹ are hydrogen, or
R⁵ and R⁶ together form a bond, and HetAr is a 5- or 6-membered heteroaryl or is a 5-or 6-membered heteroaryl which is substituted one to three times by fluoro, chloro, bromo, methyl, methoxy, cyano or trifluoromethyl.

Preferably, the heteroatoms in these HetAr moieties are selected from 1 or 2 nitrogen, oxygen or sulphur atoms.

In particular, HetAr is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl and benzisoxazolyl, where these rings are optionally substituted one or two times by fluoro, chloro, bromo, methyl, methoxy, cyano or trifluoromethyl.

In particular, HetAr is pyridyl, pyrimidinyl, pyridazinyl, quinolinyl, isoquinolinyl, cinnolinyl, phthalazinyl, quinazolinyl and quinoxalinyl, where these rings are optionally substituted one or two times by fluoro, chloro, bromo, methyl, methoxy, cyano or trifluoromethyl.

In another group of preferred compounds of the formula I, R¹ is methyl, ethyl, n-propyl, yclopropyl, halogen or $C_1$-$C_2$haloalkoxy, especially ethyl, R² is hydrogen, R³ is phenyl or pyridyl, where these rings are optionally substituted one to three times by fluoro, chloro, bromo, methyl, methoxy, cyano or trifluoromethyl, and R⁴ is hydrogen.

Certain compounds of formula (I) are alkenes, and as such undergo further reactions typical of alkenes to give additional compounds of formula (I) according to known procedures. Example of such reaction include, but are not restricted to, halogenation or hydrogenation Compounds of formula (I) wherein R⁵ and R⁶ form a bond and R⁷ is halogen, preferably chloride or bromide, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

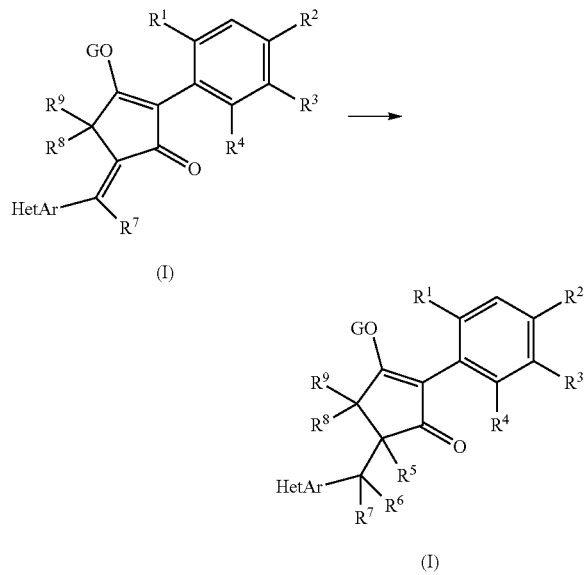

(I)

wherein R⁵ and R⁶ form a bond

Those skilled in the art will appreciate that compounds of formula (I) may contain a aromatic moiety bearing one or more substituents capable of being transformed into alternative substituents under known conditions, and that these compounds may themselves serve as intermediates in the preparation of additional compounds of formula (I).

For example, compounds of formula (I) wherein R¹, R², R³ or R⁴ is alkenyl or alkynyl, may be reduced to compounds of formula (I) wherein R¹, R², R³ or R⁴ is alkyl under known conditions and compounds of formula (I) wherein R¹, R², R³ or R⁴ is halogen, preferably bromide or iodine, may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

Compounds of formula (I) wherein G is $C_1$-$C_8$alkyl, $C_2$-$C_8$haloalkyl, phenyl $C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl $C_1$-$C_8$ alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating compounds of formula (A), which are compounds of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$ alkyl sulfate, or with a $C_3$-$C_8$ alkenyl halide, or with a $C_3$-$C_8$ alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$C(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base.

Isomeric compounds of formula (I) may be formed. For example, compounds of formula (A) may give rise to two isomeric compounds of formula (I), or to isomeric mixtures of compounds of formula (I). This invention covers both isomeric compounds of formula (I), together with mixtures of these compounds in any ratio.

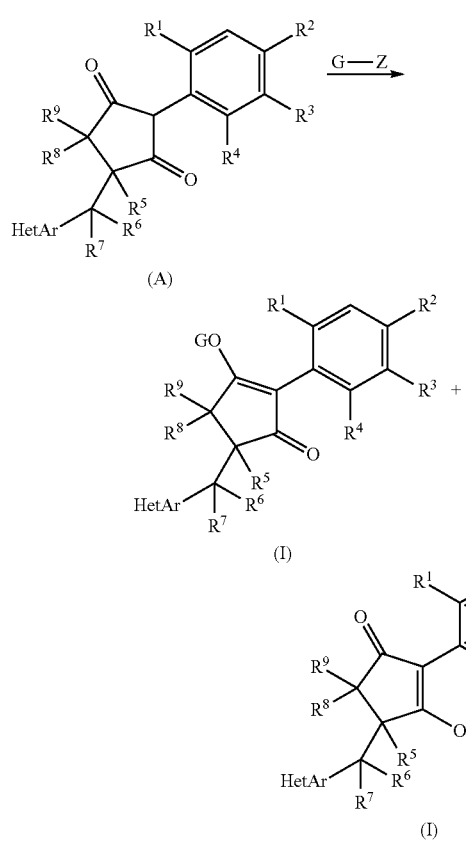

The O-alkylation of cyclic 1,3-diones is known; suitable methods are described, for example, in U.S. Pat. No. 4,436,666. Alternative procedures have been reported by Pizzorno, M. T. and Albonico, S. M. Chem. Ind. (London) (1972), 425; Born, H. et al. J. Chem. Soc. (1953), 1779; Constantino, M. G. et al. Synth. Commun. (1992), 22 (19), 2859; Tian, Y. et al. Synth. Commun. (1997), 27 (9), 1577; Chandra Roy, S. et al., Chem. Lett. (2006), 35 (1), 16; Zubaidha, P. K. et al. Tetrahedron Lett. (2004), 45, 7187 and by Zwanenburg, B. et al. Tetrahedron (2005), 45 (22), 7109.

The acylation of cyclic 1,3-diones may be effected by procedures similar to those described, for example, in U.S. Pat. Nos. 4,551,547, 4,175,135, 4,422,870, 4,659,372 and 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by Zhang, W. and Pugh, G. Tetrahedron Lett. (1999), 40 (43), 7595 and Isobe, T. and Ishikawa, T. J. Org. Chem. (1999), 64 (19) 6984.

Phosphorylation of cyclc-1,3-diones may be effected using a phosphoryl halide or thiophosphoryl halide and a base by procedures analogous to those described in U.S. Pat. No. 4,409,153.

Sulfonylation of compounds of formula (A) may be achieved using an alkyl or aryl sulfonyl halide, preferably in the presence of at least one equivalent of base, for example by the procedure of Kowalski, C. J. and Fields, K. W. J. Org. Chem. (1981), 46, 197.

Compounds of formula (A) may be prepared from a compounds of formula (I) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

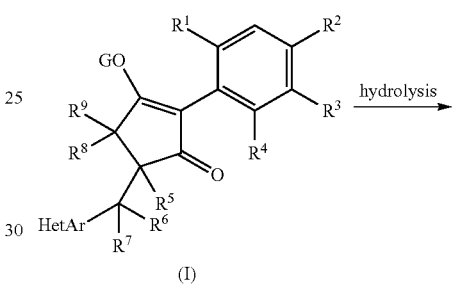

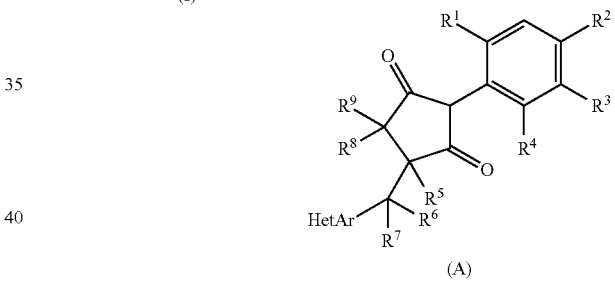

In a further approach, compounds of formula (A) may be prepared by the cyclisation of a compound of formula (B) or compounds of formula (C), wherein R''' is hydrogen or an alkyl group, preferably in the presence of an acid or base, and optionally in the presence of a suitable solvent, by analogous methods to those described by T. N. Wheeler, U.S. Pat. No. 4,209,532. The compounds of formula (B) and formula (C) have been particularly designed as intermediates in the synthesis of the compounds of the formula (I). Compounds of formula (B) or compounds of formula (C) wherein R''' is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

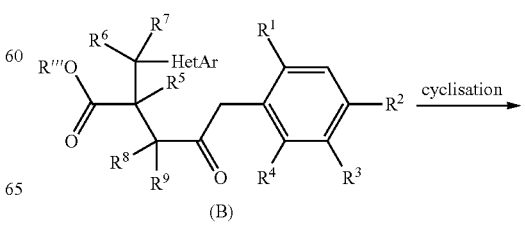

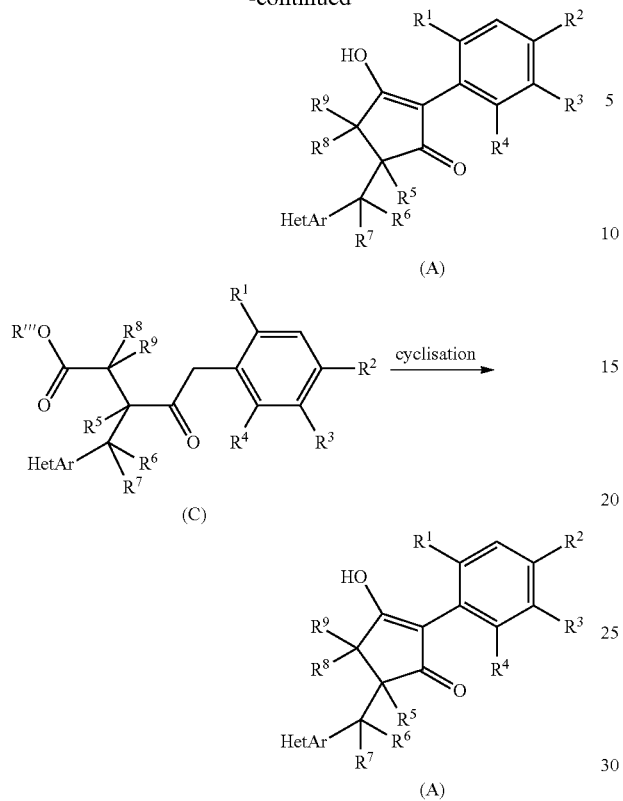

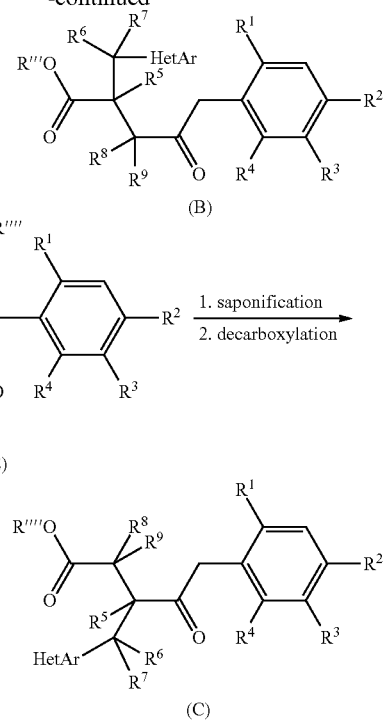

Compounds of formula (B) or compounds of formula (C) wherein R''' is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

Compounds of formula (B) and compounds of formula (C), wherein R''' is H, may be esterified to, respectively, compounds of formula (B) and compounds of formula (C), wherein R''' is alkyl, under standard conditions, for example by heating with an alkyl alcohol, ROH, in the presence of an acid catalyst.

Compounds of formula (B) and compounds of formula (C), wherein R''' is H, may be prepared, respectively, by saponification of a compounds of formula (D) and compounds of formula (E) wherein R'''' is alkyl (preferably methyl or ethyl), under standard conditions, followed by acidification of the reaction mixture to effect decarboxylation, by similar processes to those described, for example, by T. N. Wheeler, U.S. Pat. No. 4,209,532.

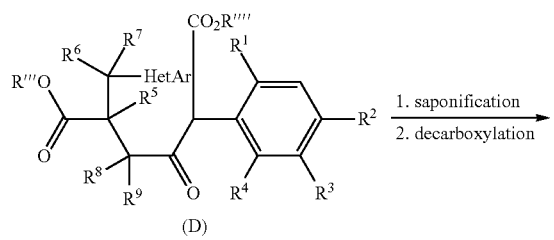

Compounds of formula (D) and compounds of formula (E), wherein R'''' is alkyl, may be prepared by treating, respectively, compounds of formula (F) with suitable carboxylic acid chlorides of formula (G) or suitable carboxylic acid chlorides of formula (H) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, compounds of formula (D) and compounds of formula (E), wherein R'''' is H, may be prepared by treating a compound of formula (F) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (J):

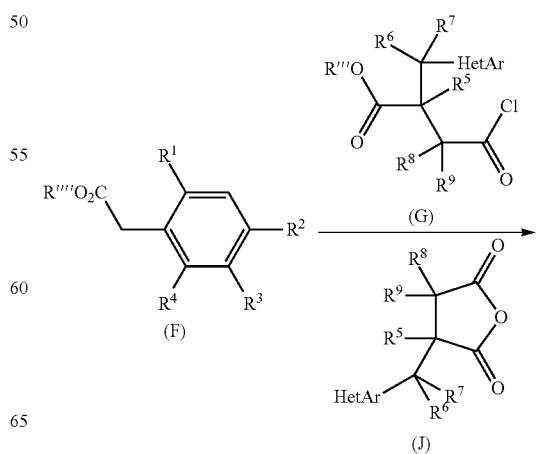

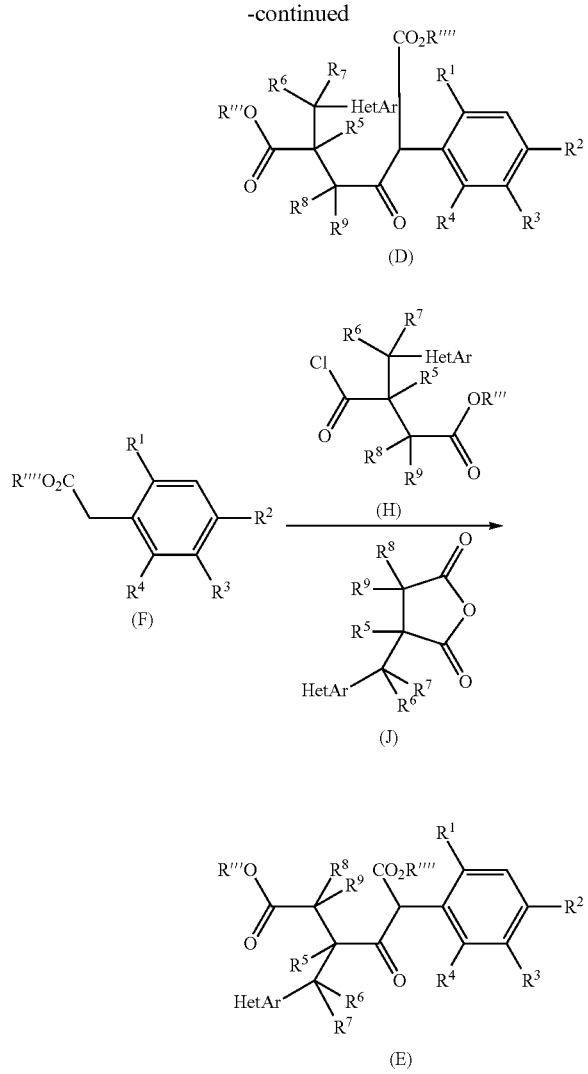

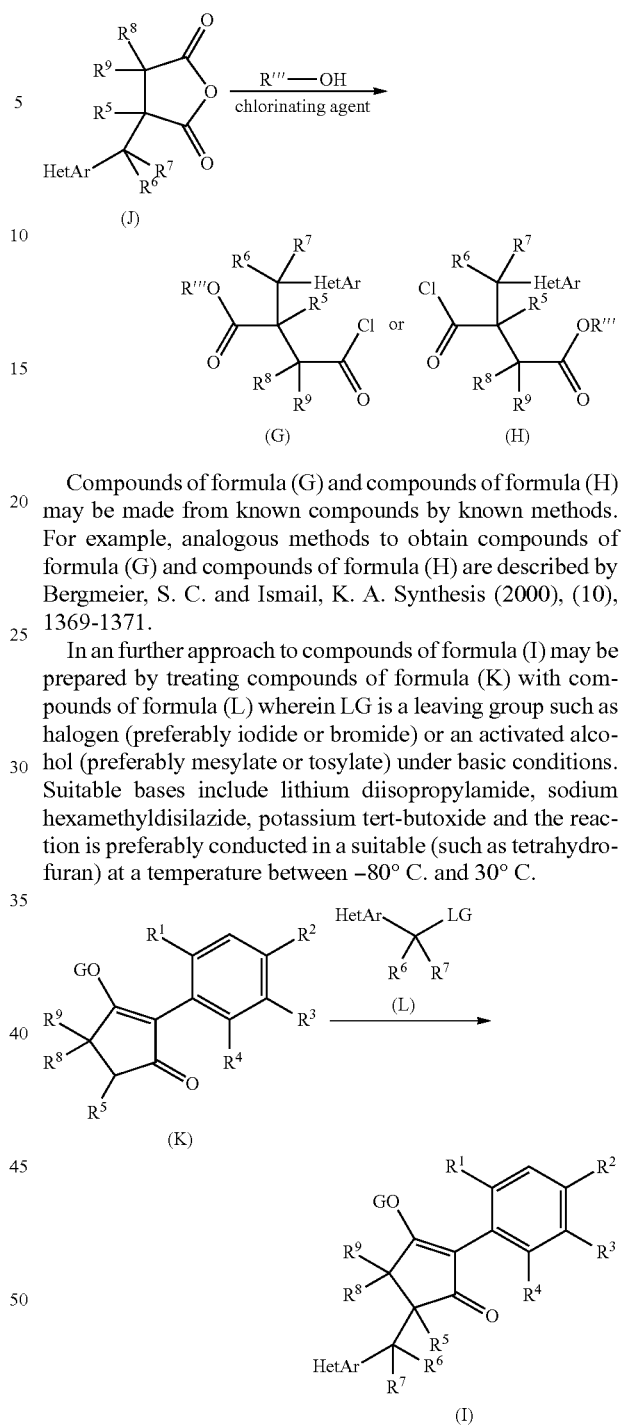

Compounds of formula (F) are known compounds, or may be prepared from known compounds by known methods.

Compounds of formula (J) may be prepared, for example, by analogous methods to those described by Ballini, R. et al. Synthesis (2002), (5), 681-685; Bergmeier, S. C. and Ismail, K. A. Synthesis (2000), (10), 1369-1371; Groutas, W. C. et al. J. Med. Chem. (1989), 32 (7), 1607-11 and Bernhard, K. and Lincke, H. Helv. Chim. Acta (1946), 29, 1457-1466.

Compounds of formula (G) or compounds of formula (H) may be prepared from a compound of formula (J) by treatment with an alkyl alcohol, R'''—OH, in the presence of a base, such as dimethylaminopyridine or an alkaline metal alkoxide (see, for example, Buser, S, and Vasella, A. Helv. Chim. Acta, (2005), 88, 3151 and M. Hart et al. Bioorg. Med. Chem. Letters, (2004), 14, 1969), followed by treatment of the resulting acid with a chlorinating reagent such as oxalyl chloride or thionyl chloride under known conditions (see, for example, Santelli-Rouvier. C. Tetrahedron Lett. (1984), 25 (39), 4371; Walba D. and Wand, M. Tetrahedron Lett. (1982), 23 (48), 4995; Cason, J. Org. Synth. Coll. Vol. III, (169), 1955).

Compounds of formula (G) and compounds of formula (H) may be made from known compounds by known methods. For example, analogous methods to obtain compounds of formula (G) and compounds of formula (H) are described by Bergmeier, S. C. and Ismail, K. A. Synthesis (2000), (10), 1369-1371.

In an further approach to compounds of formula (I) may be prepared by treating compounds of formula (K) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C.

Compounds of formula (L) are known, or may be made known compounds by known methods Compounds of formula (K) are known compounds or may be made from known compounds by known methods (see, for example, Song, Y. S. S. et al. Tetrahedron Lett. (2005), 46 (46), 5987-5990; Kuethe, J. T. et al. J. Org. Chem. (2002), 67(17), 5993-6000).

Alternatively, compounds of formula (K) wherein G is $C_1$-$C_6$alkyl may be prepared by alkylation of compounds of formula (K), wherein G is hydrogen under known conditions or by known methods (see, for example, Eberhardt, U. et al. Chem. Ber. (1983), 116 (1), 119-135).

Compounds of formula (K), wherein G is hydrogen, are known, or may be prepared from known compounds by known methods (see, for example, Nguyen, H. N. et al. J. Am. Chem. Soc. (2003), 125 (39), 11818-11819; Bonjoch, J. et al. Tetrahedron (2001), 57(28), 6011-6017; Fox, J. M. et al. J. Am. Chem. Soc. (2000), 122(7), 1360-1370; U.S. Pat. Nos. 4,338,122; 4,283,348).

Alternatively, compounds of formula (I) where $R^5$ and $R^6$ from a bond can be prepared from compounds of formula (M) by known methods (see, for example, Habib-Zahmani, H. et al. Synlett (2007), (7), 1037-1042; Nagaoka, H. et al. Tetrahedron Letters (1985), 26 (41), 5053-5056; Nagaoka, H. et al. J. Am. Chem. Soc. (1986), 108 (16), 5019-5021; Zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295).

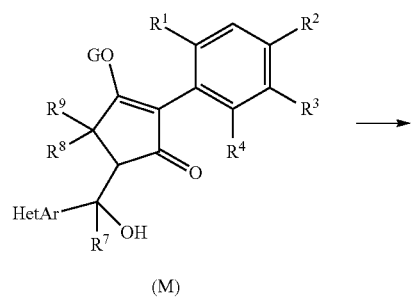

(M)

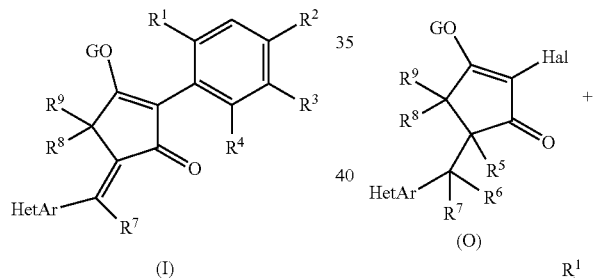

(I)

wherein $R^5$ and $R^6$ form a bond

Compounds of formula (M) may be prepared by treating compounds of formula (K) with compounds of formula (N) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C.

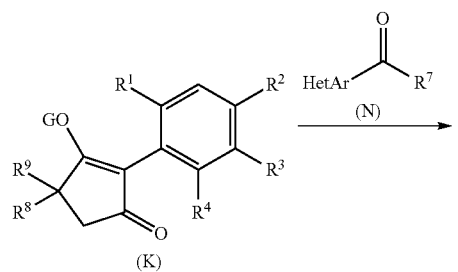

(K)

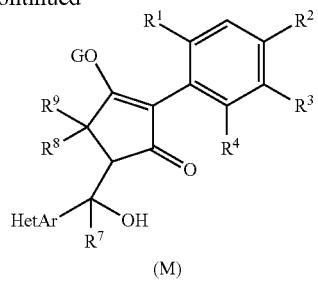

(M)

Compounds of formula (N) are known, or may be made from known compounds by known methods.

Compounds of formula (I) (wherein G is $C_1$-$C_4$alkyl) may be prepared by reacting a compounds of formula (O) (wherein G is $C_1$-$C_4$alkyl, and Hal is a halogen, preferably bromine or iodine), with aryl boronic acids, Ar—B(OH)$_2$, of formula (P) in the presence of a suitable palladium catalyst (for example 0.001-50% palladium(II) acetate with respect to compound (O)) and a base (for example 1 to 10 equivalents potassium phosphate with respect to compound (O)) and preferably in the presence of a suitable ligand (for example 0.001-50% (2-dicyclohexylphosphino)-2',6'-dimethoxybiphenyl with respect to compound (O)), and in a suitable solvent (for example toluene or 1,2-dimethoxyethane), preferably between 25° C. and 200° C. under conventional heating or under microwave irradiation (see, for example, Song, Y. S. S. et al. Tetrahedron Lett. (2005), 46 (46), 5987-5990; Kuethe, J. T. et al. J. Org. Chem. (2002), 67(17), 5993-6000).

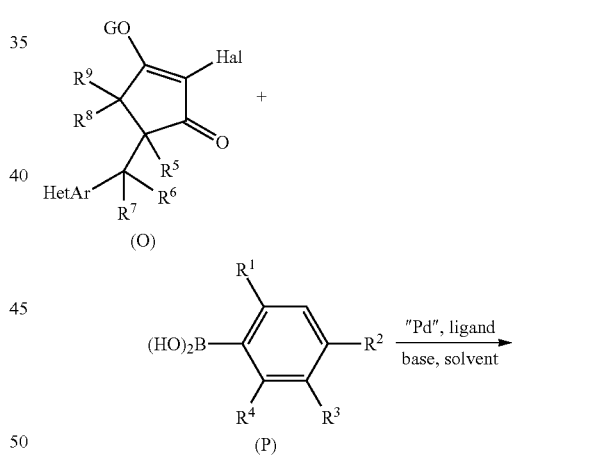

(I)

Compound of formula (O) may be prepared by halogenating a compound of formula (Q), followed by alkylation of the resulting halide of formula (R) with a $C_1$-$C_4$alkyl halide or tri-$C_1$-$C_4$alkylorthoformate under known conditions, for example by the procedures of Shepherd R. G. et al. J. Chem.

Soc. Perkin Trans. 1 (1987), 2153-2155 and Lin Y.-L. et al. Bioorg. Med. Chem. (2002), 10, 685-690. Alternatively, compounds of formula (O) may be prepared by alkylating a compound of formula (Q) with a $C_{1-4}$ alkyl halide or a tri-$C_{1-4}$-alkylorthoformate, and halogenating the resulting enone of formula (S) under known conditions (see for example Song, Y. S. et al. Tetrahedron Lett. (2005), 46 (36), 5987-5990; Kuethe, J. T. et al. J. Org. Chem. (2002), 67(17), 5993-6000; Belmont, D. T. et al. J. Org. Chem. 1985, 50 (21), 4102-4107).

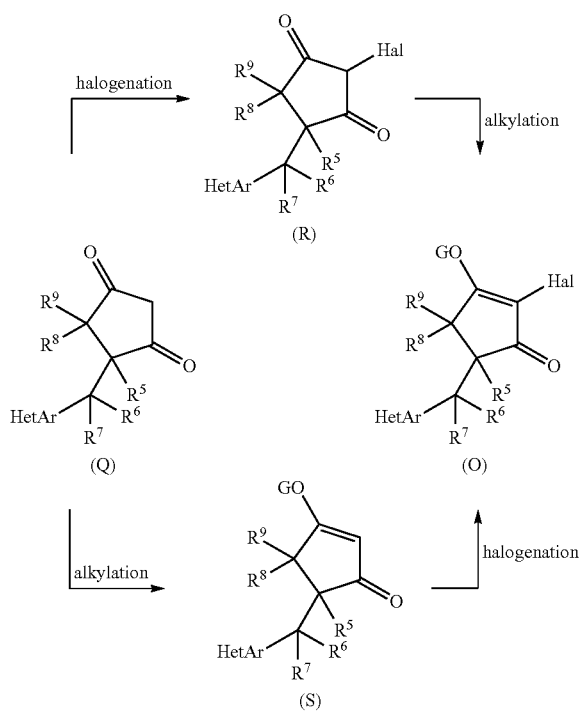

Compounds of formula (S) may be prepared by treating compounds of formula (T) with compounds of formula (L) wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C. (see, for example, Gulias, M. et al. Org. Lett. (2003), 5(11), 1975-1977; Altenbach, R. J. et al. J. Med. Chem. (2006), 49 (23), 6869-6887; Snowden, R. L. Tetrahedron (1986), 42 (12), 3277-90; Oppolzer, W. et al. Helv. Chim. Acta (1980), 63 (4), 788-92; Mellor, M. et al. Synth. Commun. 1979, 9 (1), 1-4).

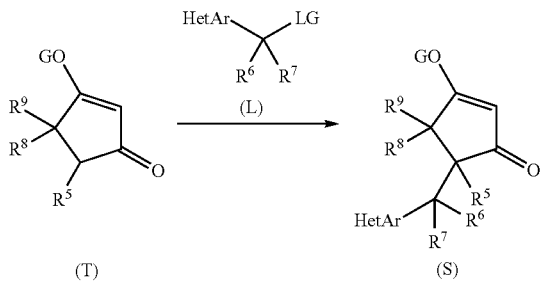

Compounds of formula (T) are known, or may be made known compounds by known methods.

Alternatively compounds of formula (S) where $R^5$ and $R^6$ from a bond can be prepared from compounds of formula (U) by known methods (see, for example, Nagaoka, H. et al. Tetrahedron Letters (1985), 26 (41), 5053-5056; Nagaoka, H. et al. J. Am. Chem. Soc. (1986), 108 (16), 5019-5021; zuki, M. et al. Bull. Chem. Soc. Japan (1988), 61(4), 1299-1312; Enholm, E. J. et al. J. Org. Chem. (1996), 61 (16), 5384-5390; Clive, D. L. J. et al. Tetrahedron (2001), 57 (18), 3845-3858; Bartoli, G. et al. J. Org. Chem. (2002), 67 (25), 9111-9114. Jung, M. E. et al. Chem. Comm. (2003), (2), 196-197; EP1433772; JP2004203844; IN194295).

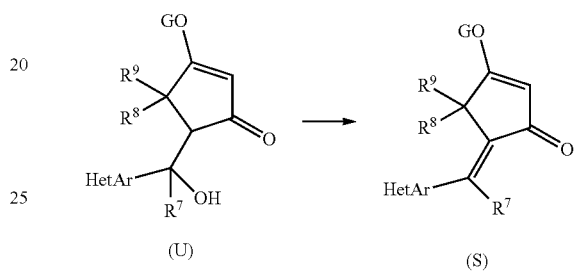

wherein $R^5$ and $R^6$ form a bond

Compounds of formula (U) may be prepared by treating compounds of formula (T) with compounds of formula (N) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C. (see, for example, Aleman, J. et al. Chem. Comm. (2007), (38), 3921-3923).

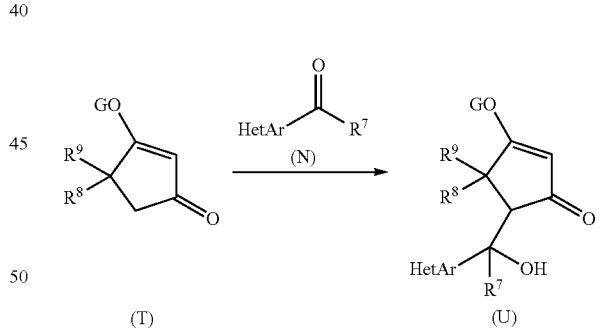

Compounds of formula (P) may be prepared from an aryl halide of formula (V), wherein Hal is bromine or iodine, by known methods (see, for example, Thompson W. et al. J. Org. Chem. (1984), 49, 5237 and R. Hawkins et al. J. Am. Chem. Soc. (1960), 82, 3053). For example, an aryl halide of formula (V) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkyl borate (preferably trimethylborate) to give an aryl dialkylboronate which may be hydrolysed to provide a boronic acid of formula (P) under acidic conditions.

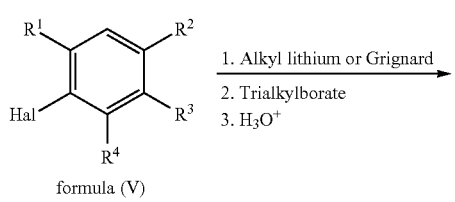

formula (V)

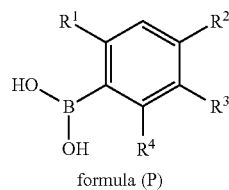

formula (P)

Alternatively a compound of formula (V) may be reacted with a cyclic boronate ester derived from a 1,2- or a 1,3-alkanediol such as pinacol, 2,2-dimethyl-1,3-propanediol and 2-methyl-2,4-pentanediol) under known conditions (see, for example, Miyaura N. et al. J. Org. Chem. (1995), 60, 7508, and Zhu W. et al. Org. Lett. (2006), 8 (2), 261), and the resulting boronate ester may be hydrolysed under acidic conditions to give a boronic acid of formula (P).

Aryl halides of formula (V) may be prepared from anilines of formula (W) by known methods, for example: the Sandmeyer reaction, via the corresponding diazonium salts.

Anilines of formula (W) are known compounds, or may be made from known compounds, by known methods.

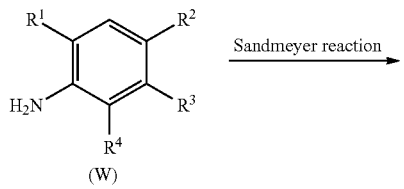

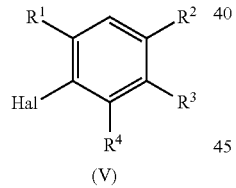

Compounds of formula (Q) may be prepared from compounds of formula (S) by hydrolysis, preferably in the presence of an acid catalyst such as hydrochloric acid and optionally in the presence of a suitable solvent such as tetrahydrofuran or acetone preferably between 25° C. and 150° C. under conventional heating or under microwave irradiation.

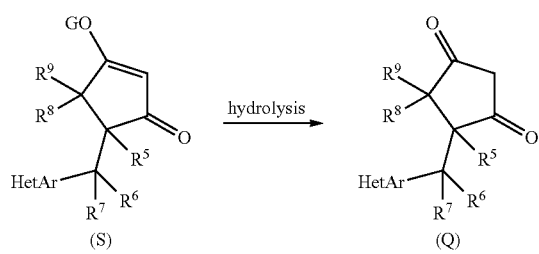

Alternatively, compounds of formula (Q) can be made from known compounds by known methods (see for example Manukina, T. A. et al. Zhurnal Organicheskoi Khimii (1986), 22(4), 873-4; Mellor, M. et al. Synth. Commun. 1979, 9 (1), 1-4).

In a further approach, compounds of formula (A) may be prepared by reacting compounds of formula (Q) with suitable aryl halides (such as aryl-iodides, aryl-bromides or aryl-chlorides), Ar—Hal, in the presence of a suitable palladium catalyst (for example 0.001-50% palladium(II) acetate with respect to compounds of formula (Q)) and a base (for example 1 to 10 equivalents potassium phosphate with respect to compounds of formula (Q)) and preferably in the presence of a suitable ligand (for example 0.001-50% (2-dicyclohexylphosphino)-2',4',6'-triisopropylbiphenyl with respect to compounds of formula (Q)), and in a suitable solvent (for example dioxane or 1,2-dimethoxyethane), preferably between 25° C. and 200° C. Similar couplings are known in the literature (see for example, Belmont, D. T. et al. J. Org. Chem. 1985, 50 (21), 4102-4107; Fox, J. M. et al. J. Am. Chem. Soc. (2000), 122 (7), 1360-1370; B. Hong et al. WO 2005/000233). Alternatively, compounds of formula (A) may be prepared by reacting compounds of formula (Q) with suitable aryl halides (such as an aryl-iodides), Ar—Hal, in the presence of a suitable copper catalyst (for example 0.001-50% copper(I) iodide with respect to compounds of formula (Q)) and a base (for example 1 to 10 equivalents potassium carbonate with respect to compounds of formula (Q)) and preferably in the presence of a suitable ligand (for example 0.001-50% L-proline with respect to compounds of formula (Q)), and in a suitable solvent (for example dimethylsulfoxide), preferably between 25° C. and 200° C. Similar couplings are known in the literature for aryl halides (see, for example, Jiang, Y. et al. Synlett (2005), 18, 2731-2734).

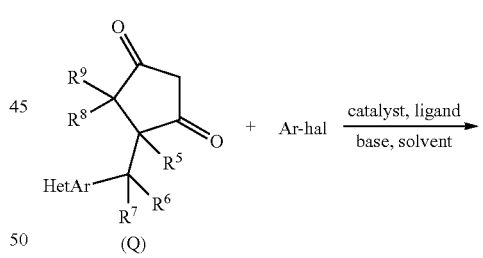

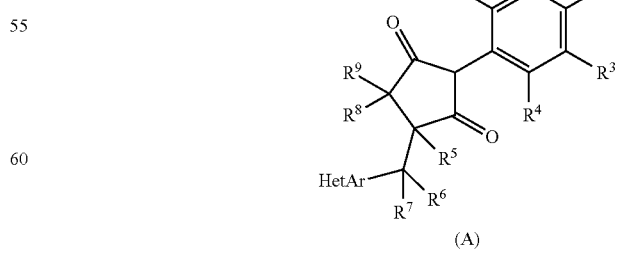

Additional compounds of formula (A) may be prepared by reacting compounds of formula (Q) with organolead reagents of formula (X) under conditions described, for example, by Pinhey, J. Pure and Appl. Chem. (1996), 68 (4), 819 and by Moloney M. et al. Tetrahedron Lett. (2002), 43, 3407.

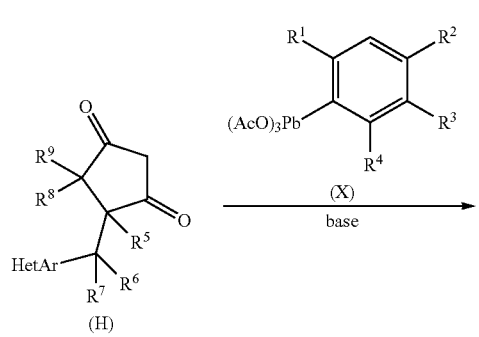

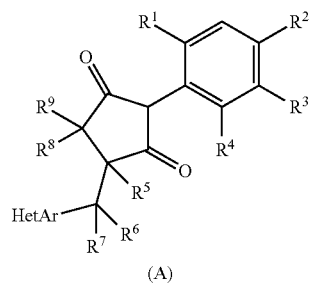

The organolead reagent of formula (X) may be prepared from a boronic acid of formula (P), a stannane of formula (Y), wherein R'''' is $C_1$-$C_4$ alkyl or by direct plumbation of a compound of formula (Z) with lead tetraacetate according to known procedures.

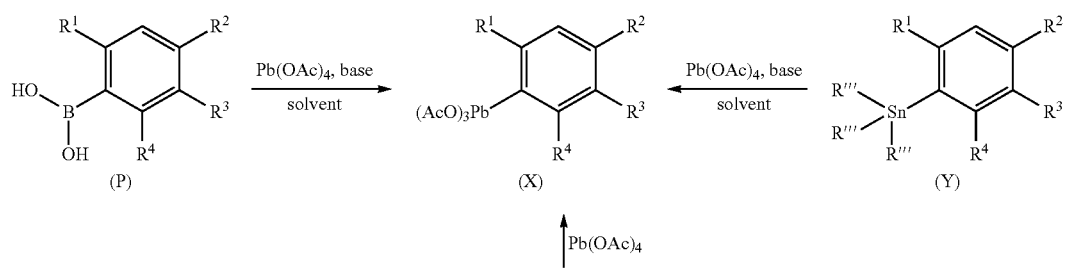

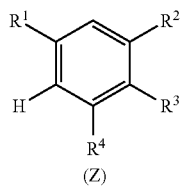

Further compounds of formula (A) may be prepared by reacting compounds of formula (Q) with suitable triarylbismuth compounds under conditions described, for example, by Fedorov, A. U. et al. Russ. Chem. Bull. Int. Ed. (2005), 54 (11), 2602 and by Koech P. et al. J. Am. Chem. Soc. (2004), 126 (17), 5350 and references therein.

Additional compounds of formula (A) may be prepared by reacting an iodonium ylide of formula (AA), wherein Ar is an optionally substituted phenyl group, and an aryl boronic acid of formula (P), in the presence of a suitable palladium catalyst, a base and in a suitable solvent.

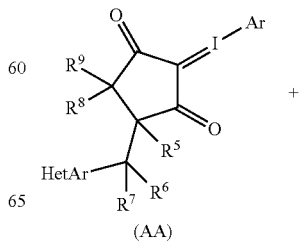

-continued

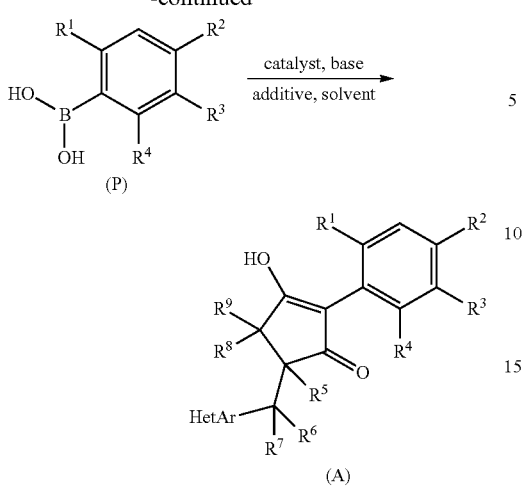

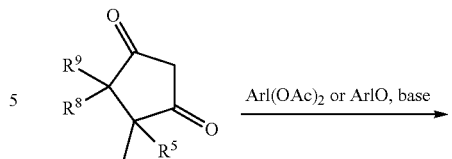

Suitable palladium catalysts are generally palladium(II) or palladium(0) complexes, for example palladium(II) dihalides, palladium(II) acetate, palladium(II) sulfate, bis(triphenylphosphine)-palladium(II) dichloride, bis(tricyclopentylphosphine)palladium(II) dichloride, bis(tricyclohexylphosphine)palladium(II) dichloride, bis(dibenzylideneacetone)palladium(0) or tetrakis-(triphenylphosphine)palladium(0). The palladium catalyst can also be prepared in situ from palladium(II) or palladium (0) compounds by complexing with the desired ligands, by, for example, combining the palladium(II) salt to be complexed, for example palladium(II) dichloride ($PdCl_2$) or palladium(II) acetate($Pd(OAc)_2$), together with the desired ligand, for example triphenylphosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (AA), the arylboronic acid of formula (P), and a base. Also suitable are bidendate ligands, for example 1, 1'-bis(diphenylphosphino)ferrocene or 1,2-bis(diphenylphosphino)ethane. By heating the reaction medium, the palladium(II) complex or palladium(0) complex desired for the C—C coupling reaction is thus formed in situ, and then initiates the C—C coupling reaction.

The palladium catalysts are used in an amount of from 0.001 to 50 mol %, preferably in an amount of from 0.1 to 15 mol %, based on the compound of formula (AA). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (AA) may be prepared from a compound of formula (Q) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of Schank K. et al. Synthesis (1983), 392, Moriarty R. M. et al. J. Am. Chem. Soc. (1985), 107, 1375 or of Yang Z. et al. Org. Lett. (2002), 4 (19), 3333.

Alternatively, compounds of formula (I) can be prepared by reaction heteroaromatic compounds (preferably thiophene, pyrrole or furan) with compounds of formula (AB)

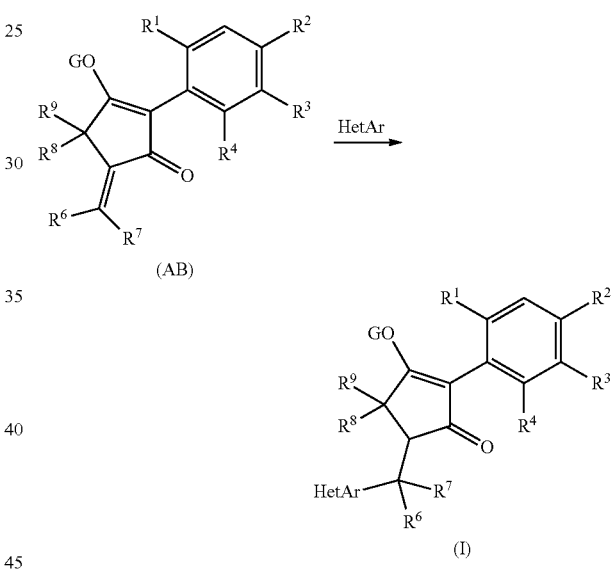

wherein $R^5$ and $R^6$ form a bond

Compounds of formula (AB) can be prepared from compounds of formula (AH) where LG is a leaving group such as halogen (preferably iodide or bromide), an activated alcohol (preferably mesylate or tosylate) under basic conditions by known methods (see, for example, Drege, E. et al. Tetrahedron Letters (2005), 46(42), 7263-7266 and Drege, E. et al. Eur. J. Org. Chem. (2006), (21), 4825-4840).

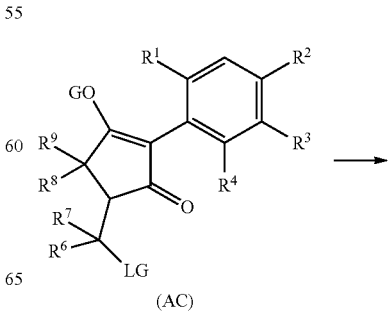

-continued

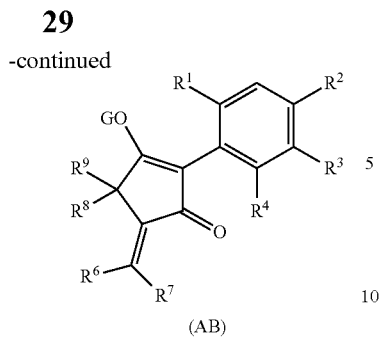

(AB)

wherein $R^5$ and $R^6$ form a bond

Compounds of formula (AC) can be prepared, for example, from compounds of formula (K) with compounds of formula (AE) under basic conditions followed by an activation of the hydroxyl group of the compounds (AD). Suitable bases include lithium diisopropylamide, sodium hexamethyldisilazide, potassium tert-butoxide and the reaction is preferably conducted in a suitable (such as tetrahydrofuran) at a temperature between −80° C. and 30° C. (see, for example, Drege, E. et al. Tetrahedron Letters (2005), 46(42), 7263-7266 and Drege, E. et al. Eur. J. Org. Chem. (2006), (21), 4825-4840).

-continued

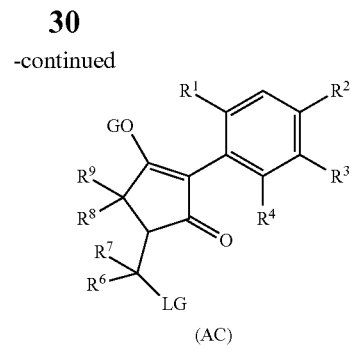

(AC)

Compounds of formula (AB) can be prepared from compounds of formula (AF) where R'''' is an alkyl group (preferably methyl or ethyl) under acidic conditions by known methods.

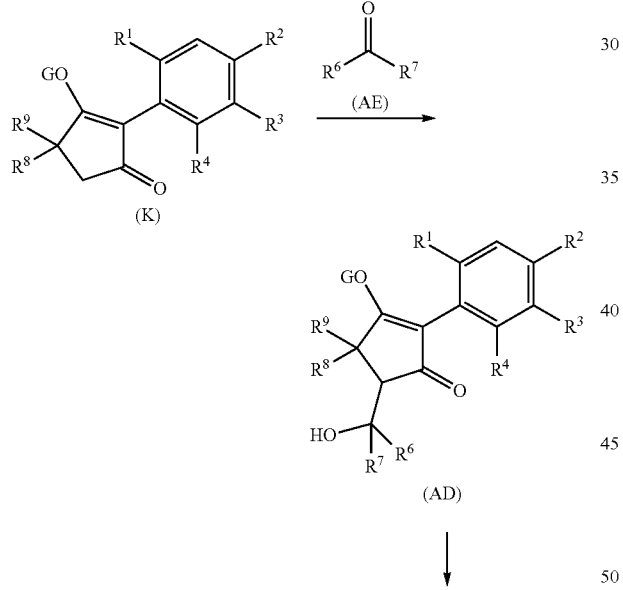

(K)

(AE)

(AD)

(AF)

(AB)

wherein $R^5$ and $R^6$ form a bond

Compounds of formula (AF) can be prepared from compounds of formula (AD) by alkylation of the free hydroxyl group under known conditions or by reaction compounds of formula (K) with compounds of formula (AG) under known conditions (see, for example, Imanishi, T. et al. J. Chem. Soc., Chem. Comm. (1987), (23), 1802-1804).

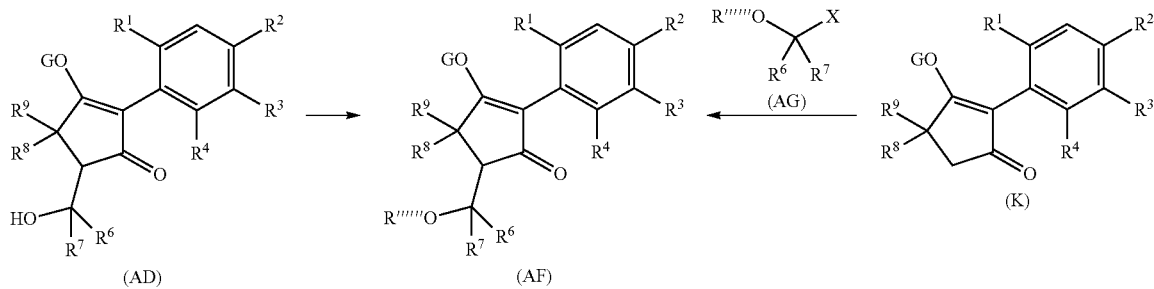

(AD)

(AF)

(AG)

(K)

Additional compounds of formula (A) may be prepared by the pinacol rearrangement of compounds of formula (AH) or compounds of formula (AJ) wherein R'''''' is $C_1$-$C_4$ alkyl (preferably methyl) under acidic conditions (see, for example, Eberhardt, U. et. al. Chem. Ber. (1983), 116(1), 119-35 and Wheeler, T. N. U.S. Pat. No. 4,283,348)

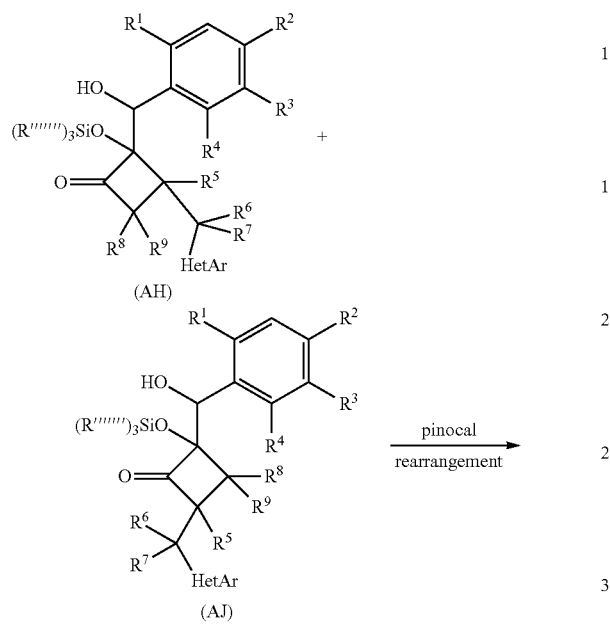

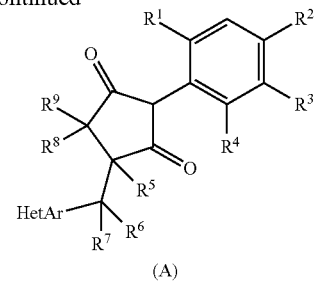

Compounds of formula (AH) and compounds of formula (AJ) may be prepared by treating compounds of formula (AK) with compounds of formula (AL) in the presence of an acid (such as titanium chloride or magnesium iodide) optionally in a suitable solvent (such as dichloromethane) at a temperature between −80° C. and 30° C. (see, for example, Li, W.-D. Z. and Zhang, X.-X. Org. Lett. (2002), 4(20), 3485-3488; Shimada, J. et al. J. Am. Chem. Soc. (1984), 106(6), 1759-73; Eberhardt, U. et. al. Chem. Ber. (1983), 116(1), 119-35 and Wheeler, T. N. U.S. Pat. No. 4,283,348).

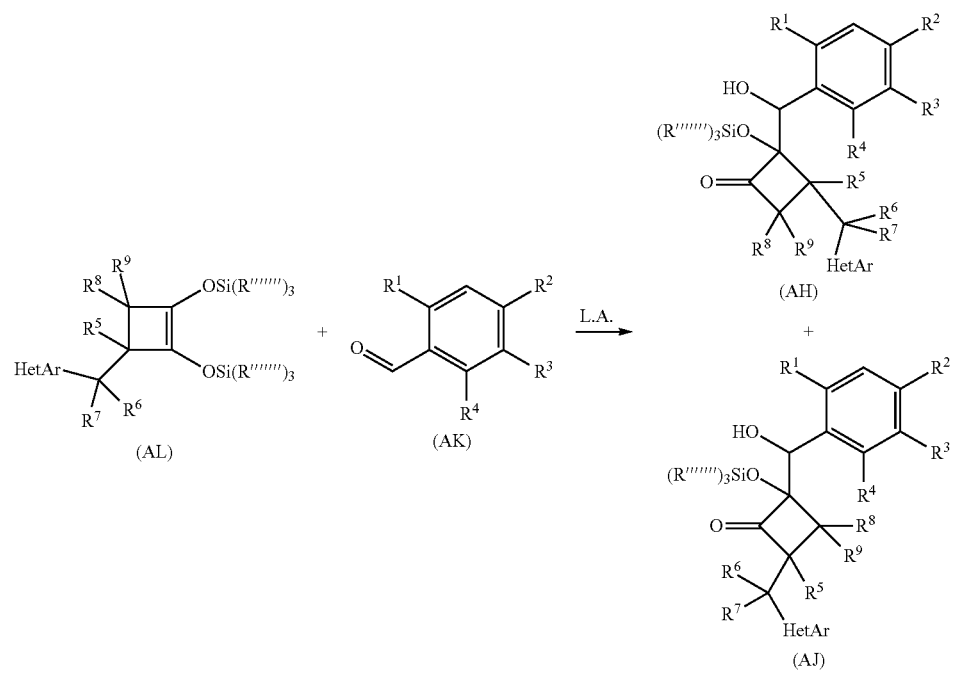

Compounds of formula (AK) are known or may be made by known methods from compounds of formula (V).

Compounds of formula (AL) may be prepared from compounds of formula (AM) where in R''' is an alkyl group (preferably methyl) in the presence of chloro tri-$C_1$-$C_4$alkyl silyl and a metal (preferably sodium) in a suitable solvent (such as toluene or diethyl ether) at a temperature between 20° C. and 150° C. (see, for example, Blanchard, A. N. and Burnell, D. J. Tetrahedron Lett. (2001), 42(29), 4779-4781 and Salaun, J. et al. Tetrahedron (1989), 45(10), 3151-62).

wherein LG is a leaving group such as halogen (preferably iodide or bromide) or an activated alcohol (preferably mesylate or tosylate) under basic conditions. Suitable bases include lithium diisopropylamide, sodium hexamethyldisilazide, potassium tert-butoxide and the reaction is preferably conducted in a suitable (such as tetrahydrofuran) at a temperature between −80° C. and 30° C. Similar reactions are described by Gulias, M. et al. Org. Lett. (2003), 5(11), 1975-1977.

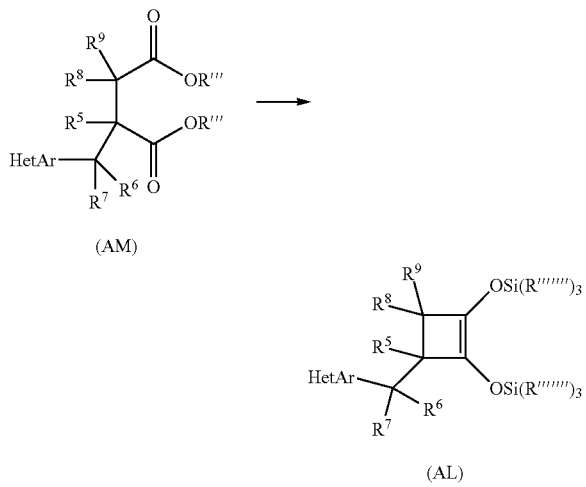

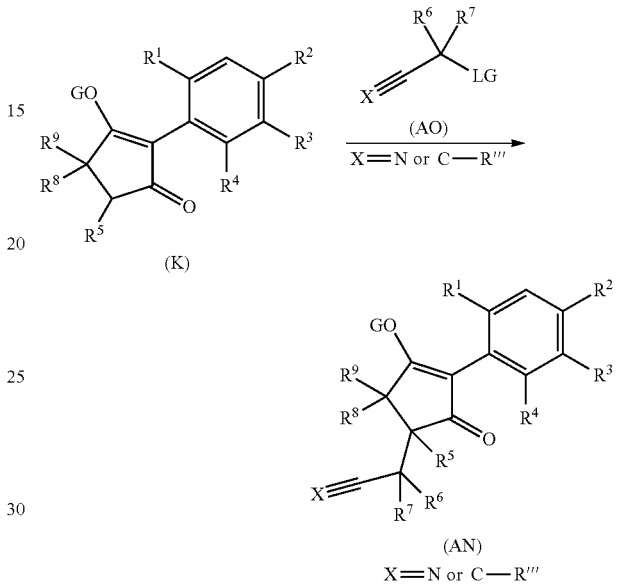

Compounds of formula (AM) are analogous to compounds of formula (H) and compounds of formula (G) and may be prepared by analogous methods to those describe for compounds of formula (H) and compounds of formula (G).

Additional compounds of formula (A) may be prepared by reacting a compounds of formula (AN) wherein X is either N or C—R''' wherein R''' is an alkyl group (preferably methyl) with a 1,3-dipole in analogous methods to the ones described by Huisgen, R. Angew. Chem. Int. Ed. (1963), 565-632.

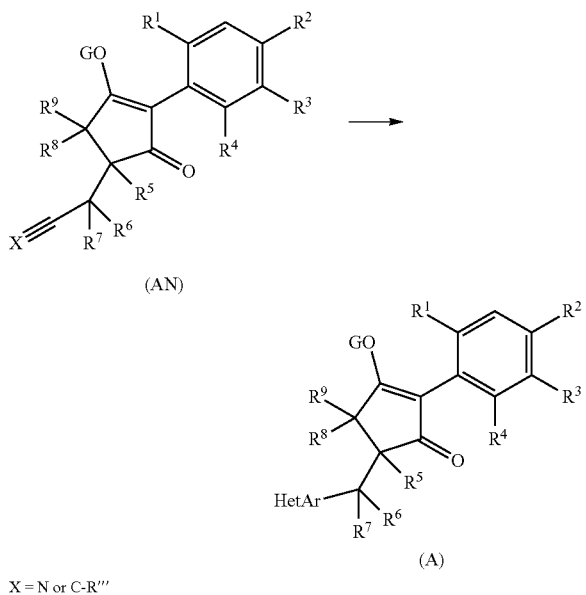

Compounds of formula (AN) can be obtained by reacting compounds of forluma (K) with compounds of formula (AO)

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means.

Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethyl-formamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alcohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulphate; Sodium lauryl sulphate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscositymodifying substances, suspending agents, dyes, anti-oxidants, foaming agents, light absorbers, mixing aids, antifoams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO(O)(Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRIDEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following representative compositions:
(%=percent by weight):
Emulsifiable concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension concentrates:
active ingredient: 5 to 75%, preferably 10 to 50%
water: 94 to 24%, preferably 88 to 30%
surface-active agents: 1 to 40%, preferably 2 to 30%
Wettable powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | |
| Sodium sulphate | | 4% | 5% | |
| kaolin | 48% | 30% | 30% | |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 58 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIN-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, 2,4-D, compound of formula (I)+dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

The compounds of formula I according to the invention can also be used in combination with safeners. Preferably, in these mixtures, the compound of the formula I is one of those compounds listed in Tables 1 to 58 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Example 1

Preparation of 4-(5-methyl-isoxazol-3-ylmethyl)-2-(2,4,6-trimethyl-phenyl)-cyclopentane-1,3-dione

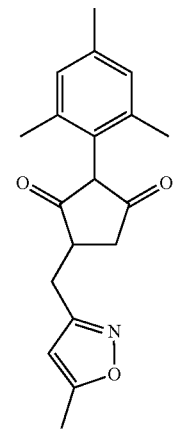

Step 1

Preparation of 2-bromo-3-methoxy-cyclopent-2-enone

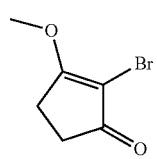

To a stirred solution of 3-methoxy-cyclopent-2-enone (14.95 g, 0.133 mmol) in 1,2-dichloroethane (300 ml) at 0° C. in an amber flask is added portionwise over one hour N-bromosuccinimide (24.92 g, 140 mmol). The reaction is stirred at 0° C. for a further 90 minutes and then any remaining solid is removed by filtration. The filtrate is evaporated to dryness under reduced pressure, the resultant solid dissolved in warm toluene (600 ml) and washed quickly with water (2×100 ml). The organic phase is evaporated under reduced pressure until a precipitate appears. The residue is cooled overnight in a fridge. The resultant solid is removed by filtration, washed with hexane (50 ml) and air-dried to give 15.2 g of 2-bromo-3-methoxy-cyclopent-2-enone as a white crystalline solid.

Step 2

Preparation of 3-methoxy-2-(2,4,6-trimethyl-phenyl)-cyclopent-2-enone

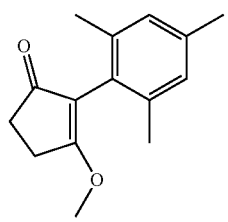 [SMILES: COC1=C(c2c(C)cc(C)cc2C)C(=O)CC1]

To a suspension of 2-bromo-3-methoxy-cyclopent-2-enone (32.3 g 169 mmol), 2,4,6-trimethylphenyl boronic acid (29.5 g, 180 mmol) and freshly ground potassium phosphate (63.7 g) in degassed toluene (800 ml) under $N_2$ is added Pd(OAc)$_2$ (896 mg, 8 mmol) and S-Phos (1.64 g, 4 mmol), and the reaction heated to 90° C. with stirring under $N_2$ overnight. The reaction is partitioned between ethyl acetate (500 ml) and water (500 ml), and the organic layer is removed and the aqueous phase is extracted with ethyl acetate (2×300 ml). The combined organic extracts are evaporated under reduced pressure and the residue is purified to give 3-methoxy-2-(2,4,6-trimethyl-phenyl)-cyclopent-2-enone (30.7 g).

Step 3

Preparation of 3-Methoxy-5-(5-methyl-isoxazol-3-ylmethyl)-2-(2,4,6-trimethyl-phenyl)-cyclopent-2-enone

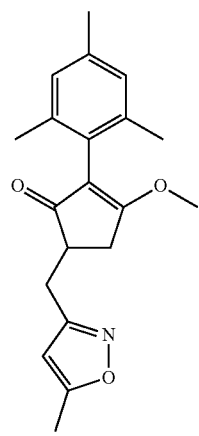

A flask is charged with 3-methoxy-2-(2,4,6-trimethyl-phenyl)-cyclopent-2-enone (230 mg, 1 mmol), purged with nitrogen and anhydrous THF (5 ml) added. The resulting solution is cooled to −78° C. and lithium diisopropylamide (1.8M solution in hexane/THF/ethyl benzene) (0.61 ml, 1.1 mmol) is added dropwise and the reaction stirred at −78° C. for a further 30 minutes. A solution of 3-chloromethyl-5-methyl isoxazole in THF (1 ml) is then added in one portion, and the reaction is allowed to warm to ambient temperature and stirred for a further 2 hours. The reaction is quenched by the addition of saturated ammonium chloride solution (20 ml), and extracted with ethyl acetate (2×20 ml). The combined organics are evaporated under reduced pressure and the residue is purified by flash chromatography to give 3-methoxy-5-(5-methyl-isoxazol-3-ylmethyl)-2-(2,4,6-trimethyl-phenyl)-cyclopent-2-enone (132 mg)

Preparation of 4-(5-methyl-isoxazol-3-ylmethyl)-2-(2,4,6-trimethyl-phenyl)-cyclopentane-1,3-dione

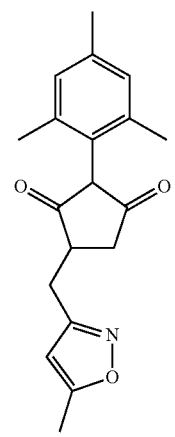

To a solution of 3-methoxy-5-(5-methyl-isoxazol-3-ylmethyl)-2-(2,4,6-trimethyl-phenyl)-cyclopent-2-enone (120 mg) in acetone (1 ml) in a microwave vial is added 2N HCl (0.6 ml) and the resultant solution is heated to 130° C. by microwave irradiation, with stirring, for 30 minutes. The solvent is removed under reduced pressure, and the residue triturated with hexane to give a white solid, which is filtered and washed well with hexane to give 4-(5-methyl-isoxazol-3-ylmethyl)-2-(2,4,6-trimethyl-phenyl)-cyclopentane-1,3-dione.

Example 2

Preparation of 2,2-Dimethyl-propionic acid 4-[1-furan-3-yl-meth-(E)-ylidene]-3-oxo-2-(2,4,6-trimethyl-phenyl)-cyclopent-1-enyl ester

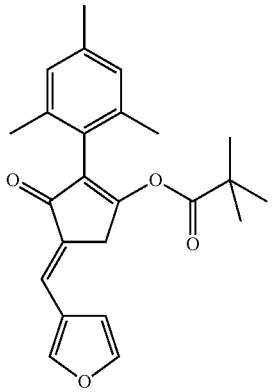 [SMILES: Cc1cc(C)c(C2=C(OC(=O)C(C)(C)C)C/C(=C\c3ccoc3)C2=O)c(C)c1]

Step 1

Preparation of 5-(furan-3-yl-hydroxy-methyl)-3-methoxy-2-(2,4,6-trimethyl-phenyl)-cyclopent-2-enone

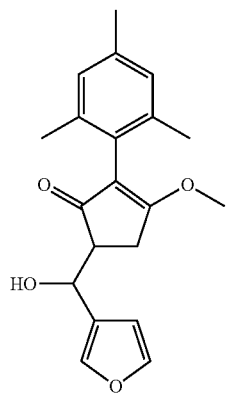 [SMILES: COC1=C(c2c(C)cc(C)cc2C)C(=O)C(C(O)c2ccoc2)C1]

To a solution of diisopropylamine (527 μl) in THF (5 ml) under nitrogen at −78° C. is added, dropwise, butyl lithium, 2.5M solution in hexane (1.32 ml) and the reaction allowed to stir at −78° C. for 20 minutes. This solution is then added dropwise to a solution of 3-methoxy-2-(2,4,6-trimethyl-phenyl)-cyclopent-2-enone (691 mg) in THF (5 ml) under nitrogen at −78° C. and the resulting solution allowed to stir for a further 30 minutes. A solution of 3-furaldehyde (377 mg) in THF (1 ml) is then added in one portion and the reaction is allowed to warm to room temperature and stirred for a further 30 minutes. The reaction is quenched by the addition of saturated ammonium chloride (50 ml) and extracted with ethyl acetate (50 ml). The organic layer is removed and purified by automated flash chromatography to give 5-(furan-3-yl-hydroxy-methyl)-3-methoxy-2-(2,4,6-trimethyl-phenyl)-cyclopent-2-enone (784 mg)

Step 2

Preparation of 4-[1-Furan-3-yl-meth-(E)-ylidene]-2-(2,4,6-trimethyl-phenyl)-cyclopentane-1,3-dione

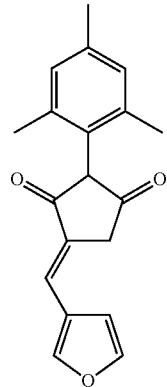

To a solution of 5-(furan-3-yl-hydroxy-methyl)-3-methoxy-2-(2,4,6-trimethyl-phenyl)-cyclopent-2-enone (770 mg) in acetone (2 ml) is added 2N hydrochloric acid (2 ml) and the resulting suspension heated to 120° C. for 30 minutes. The crude reaction mixture is concentrated in vacuuo and purified by flash chromatography to give 4-[1-furan-3-yl-meth-(E)-ylidene]-2-(2,4,6-trimethyl-phenyl)-cyclopentane-1,3-dione.

Step 3

Preparation of 2,2-dimethyl-propionic acid 4-[1-furan-3-yl-meth-(E)-ylidene]-3-oxo-2-(2,4,6-trimethyl-phenyl)-cyclopent-1-enyl ester

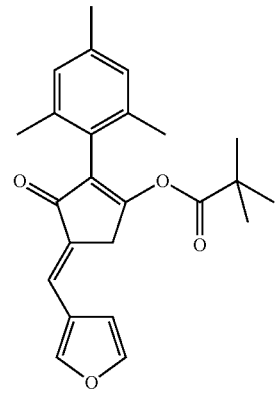 [SMILES: Cc1cc(C)c(C2=C(OC(=O)C(C)(C)C)C/C(=C\c3ccoc3)C2=O)c(C)c1]

To a solution of 4-[1-furan-3-yl-meth-(E)-ylidene]-2-(2,4,6-trimethyl-phenyl)-cyclopentane-1,3-dione (50 mg) in dichloromethane (2 ml) is added triethylamine (118 μl), followed by trimethylacetyl chloride (105 μl) and the resulting suspension allowed to stir at room temperature for 3 hours. The crude reaction mixture is then purified by automated flash chromatography to give 2,2-dimethyl-propionic acid 4-[1-furan-3-yl-meth-(E)-ylidene]-3-oxo-2-(2,4,6-trimethyl-phenyl)-cyclopent-1-enyl ester.

Example 3

Preparation of 4-Furan-3-ylmethyl-2-(2,4,6-trimethyl-phenyl)-cyclopentane-1,3-dione

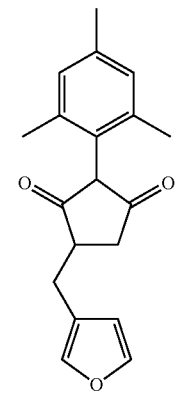

Step 1

Preparation of 4-Furan-3-ylmethyl-2-(2,4,6-trimethyl-phenyl)-cyclopentane-1,3-dione To a solution of 4-[1-Furan-3-yl-meth-(E)-ylidene]-2-(2,4,6-trimethyl-phenyl)-cyclopentane-1,3-dione (167 mg) in ethanol (5 ml) is added 5% palladium on charcoal (15 mg) and the resulting suspension stirred under an atmosphere of hydrogen (3 bar) for 5 hours. The reaction is filtered through a pad of Celite, washed with methanol and the filtrate purified by automated flash chromatography to give 4-furan-3-ylmethyl-2-(2,4,6-trimethyl-phenyl)-cyclopentane-1,3-dione.

Example 4

Preparation of 4-Benzofuran-2-ylmethyl-2-(2,4,6-trimethyl-phenyl)-cyclopentane-1,3-dione

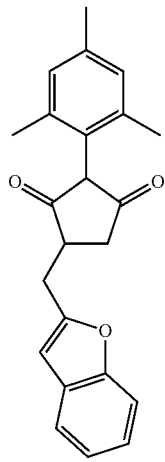

Step 1

Preparation of 5-(benzofuran-2-yl-hydroxy-methyl)-3-methoxy-2-(2,4,6-trimethyl-phenyl)-cyclopent-2-enone

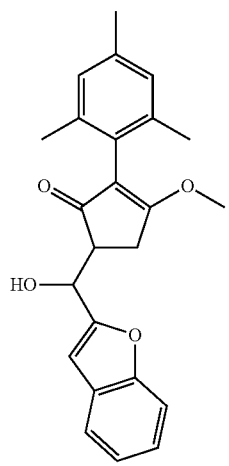 [SMILES: COC1=C(c2c(C)cc(C)cc2C)C(=O)C(C(O)c2cc3ccccc3o2)C1]

A flask is charged with 3-methoxy-2-(2,4,6-trimethyl-phenyl)-cyclopent-2-enone (691 mg, 3 mmol), purged with nitrogen and anhydrous THF (10 ml) added. The resulting solution is cooled to −78° C. and lithium diisopropylamide (1.8M solution in hexane/THF/ethyl benzene) (1.83 ml, 3.3 mmol) is added dropwise and the reaction stirred at −78° C. for a further 30 minutes. A solution of 2-benzofuraldehyde (400 μl, 3.3 mmol) in THF (1 ml) is then added in one portion, and the reaction is allowed to warm to ambient temperature and stirred for a further 2 hours. The reaction is quenched by the addition of saturated ammonium chloride solution (60 ml), and extracted with ethyl acetate (2×60 ml). The combined organics are evaporated under reduced pressure and the residue is purified by flash chromatography to give 5-(benzofuran-2-yl-hydroxy-methyl)-3-methoxy-2-(2,4,6-trimethyl-phenyl)-cyclopent-2-enone (1.11 g)

Step 2

Preparation of 5-[1-benzofuran-2-yl-meth-(E)-ylidene]-3-methoxy-2-(2,4,6-trimethyl-phenyl)-cyclopent-2-enone

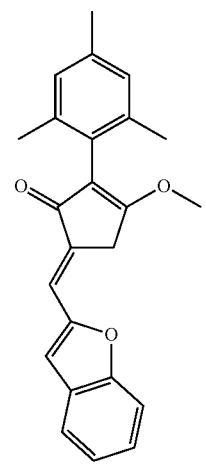

To a solution of 5-(benzofuran-2-yl-hydroxy-methyl)-3-methoxy-2-(2,4,6-trimethyl-phenyl)-cyclopent-2-enone (1.11 g) in methanol (10 ml) is added potassium carbonate (476 mg), followed by methyl iodide (214 μl) and the resulting suspension heated to reflux for 17 hours. The crude reaction mixture is then concentrated in vacuuo and partitioned between ethyl acetate (50 ml) and water (50 ml) and the organic layer purified by automated flash chromatography to give 5-[1-benzofuran-2-yl-meth-(E)-ylidene]-3-methoxy-2-(2,4,6-trimethyl-phenyl)-cyclopent-2-enone (337 mg).

Step 3

Preparation of 5-benzofuran-2-ylmethyl-3-methoxy-2-(2,4,6-trimethyl-phenyl)-cyclopent-2-enone

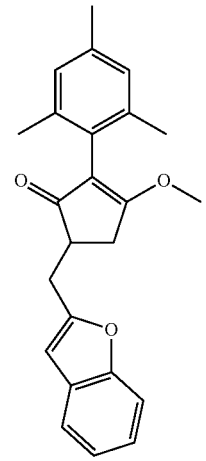

To a solution of 5-[1-benzofuran-2-yl-meth-(E)-ylidene]-3-methoxy-2-(2,4,6-trimethyl-phenyl)-cyclopent-2-enon (318 mg) in ethanol (10 ml) is added 10% palladium on charcoal (32 mg) and the resulting suspension stirred under an atmosphere of hydrogen (4 bar) for 5 hours. The reaction is filtered through a pad of Celite, washed with methanol and the filtrate concentrated in vacuuo to give 5-benzofuran-2-ylmethyl-3-methoxy-2-(2,4,6-trimethyl-phenyl)-cyclopent-2-enone (315 mg).

Step 4

Preparation of 4-benzofuran-2-ylmethyl-2-(2,4,6-trimethyl-phenyl)-cyclopentane-1,3-dione

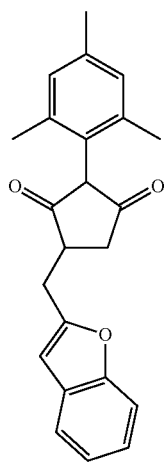

To a solution of 5-benzofuran-2-ylmethyl-3-methoxy-2-(2,4,6-trimethyl-phenyl)-cyclopent-2-enone (298 mg) in acetone (2 ml) is added 2N HCl and the resulting suspension heated to 50° C. for 5 hours. The reaction is then diluted with 2N HCl (50 ml) and extracted with ethyl acetate (50 ml) and the organic layer removed, dried over magnesium sulphate and concentrated in vacuuo to give 4-Benzofuran-2-ylmethyl-2-(2,4,6-trimethyl-phenyl)-cyclopentane-1,3-dione.

Example 5

Preparation of 4-(3-methylthiophen-2-ylmethyl)-2-(2,4,6-trimethylphenyl)cyclopentane-1,3-dione

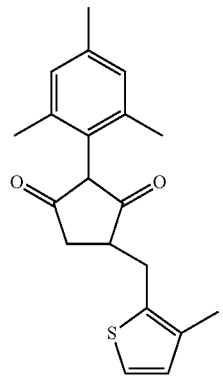

Step 1

Preparation of 4-[1-(3-methylthiophen-2-yl)-meth-(E)-ylidene]-2-(2,4,6-trimethylphenyl)cyclopentqane-1,3-dione

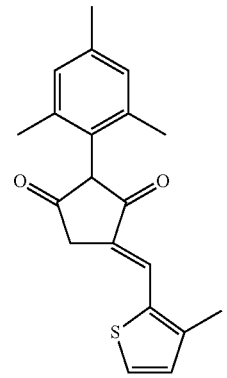

Potassium tertiary butoxide (0.53 g, 4.72 mmol) is added to a cold solution of mixture of 3-Methoxy-2-(2,4,6-trimethylphenyl)cyclopent-2-enone (0.5 g, 2.16 mmol) in tetrahydrofuran (5 ml). The reaction mixture is stirred for 30 minutes at 0° C. and to this mixture is added a solution of 3-methyl-2-thiophene carboxaldehyde (0.23 g, 1.82 mmol) in tetrahydrofuran (1 ml). The reaction mixture is stirred at 0° C. for 2 hours, acidified to pH 1 with 2N aqueous hydrochloric acid and the aqueous phase is extracted with ethyl acetate (3×25 ml), the organic phases are combined, washed with water, and dried over anhydrous sodium sulphate. The mixture is filtered, and the filtrate is evaporated under reduced pressure to give a crude residue. The crude residue is dissolved in acetone (6 ml), added concentrated hydrochloric acid (3 ml) and the resulting solution is heated to 60° C. for 8 hrs. The reaction mixture is diluted with water and extracted with ethyl acetate (3×25 ml). The combined organics are washed with brine, dried over sodium sulphate, filtered and concentrated in vacuum to give a residue. This residue is then purified using silica gel column chromatography to give 4-[1-(3-methylthiophen-2-yl)-meth-(E)-ylidene]-2-(2,4,6-trimethylphenyl)cyclopentane-1,3-dione (100 mg).

Step 2

Preparation of 4-(3-methylthiophen-2-ylmethyl)-2-(2,4,6-trimethylphenyl)cyclopentane-1,3-dione

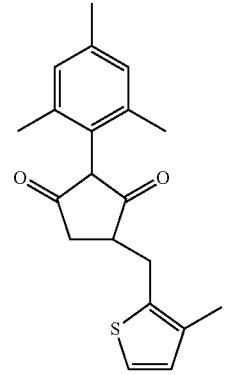

To a solution of 4-[1-(3-methylthiophen-2-yl)-meth-(E)-ylidene]-2-(2,4,6-trimethylphenyl)cyclopentane-1,3-dione (100 mg, 0.31 mmol) in methanol (10 ml) is hydrogenated in a H-Cube using 10% palladium on charcoal at 40° C. and 10 bar hydrogen pressure with a flow rate of 0.5 ml/min. The eluate collected is concentrated under vacuum to give a residue which is purified by silica gel column chromatography to give 4-(3-methylthiophen-2-ylmethyl)-2-(2,4,6-trimethylphenyl)cyclopentane-1,3-dione.

Additional compounds in Table T1 and P1 below were prepared by similar methods using appropriate starting materials.

Where more than one tautomer or rotational conformer is observed in the proton NMR spectrum, the data shown below are for the mixture of isomers and conformers.

Unless otherwise stated, proton NMR spectra were recorded at ambient temperature.

Compounds characterised by HPLC-MS were analysed using one of three methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 10.0 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: H$_2$O containing 0.1% HCOOH
Solvent B: CH$_3$CN containing 0.1% HCOOH Method B Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minutes run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.00 | 100 | 1.300 |
| 2.80 | 0.00 | 100 | 1.300 |
| 2.90 | 95.0 | 5 | 1.300 |

Solvent A: H$_2$O with 0.05% TFA
Solvent B: CH$_3$CN with 0.05% TFA

Method C:

Compounds characterised by HPLC-MS were analysed using a Thermo Finnigan Surveyor MSQ Plus equipped with a Waters Xterra column RP-18 (column length 50 mm, internal diameter of column 4.6 mm, particle size 3.5 micron, temperature 30° C.), Surveyor photodiode array Plus. The analysis was conducted using a six minutes run time, according to the following gradient table:

| Time (mins) | Solvent A (%) | Solvent B (%) | Flow (ml/mn) |
|---|---|---|---|
| 0.00 | 90.0 | 10.0 | 1.30 |
| 3.80 | 0.00 | 100 | 1.30 |
| 4.80 | 0.00 | 100 | 1.30 |
| 5.00 | 90.0 | 10.0 | 1.30 |
| 6.00 | 90.0 | 10.0 | 1.30 |

Solvent A: H$_2$O containing 0.05% HCOOH
Solvent B: CH$_3$CN containing 0.05% HCOOH

TABLE T1

| Compound Number | Structure | $^1$H nmr (CDCl$_3$ unless stated) or other physical data |
|---|---|---|
| T1 | (structure) | δ ppm 1.02-1.12 (m, 6H), 2.21-2.46 (m, 10H), 2.55-3.55 (m, 5H), 5.88-5.97 (m, 1H), 6.89-6.98 (m, 2H), 10.12 (s, 1H) |
| T2 | (structure) | δ ppm 1.94 (s, 3H) 2.09 (s, 3H) 2.27 (s, 3H) 2.45 (d, 1H) 2.71-2.85 (m, 3H) 2.99 (dd, 1H) 6.31 (s, 1H) 6.91 (d, 2H) 7.29 (s, 1H) 7.36 (s, 1H) |
| T3 | (structure) | δ ppm 1.84-2.15 (m, 6H) 2.22-2.42 (m, 7H) 2.91-3.19 (m, 3H) 3.13-3.49 (m, 1H) 5.82-6.6.98 (m, 1H) 6.82-6.91 (m, 2H) 10.22 (s, 1H) |

TABLE T1-continued

| Compound Number | Structure | ¹H nmr (CDCl₃ unless stated) or other physical data |
|---|---|---|
| T4 | 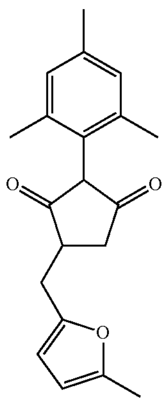 | δ ppm 1.98 (s, 3H) 2.07 (s, 3H) 2.24 (s, 3H) 2.27 (s, 3H) 2.52-2.63 (m, 1H) 2.73-2.89 (m, 2H) 3.05-3.12 (m, 1H) 3.16 (dd, 1H) 5.85 (d, 1H) 5.95 (d, 1H) 6.89 (d, 2H) |
| T5 | 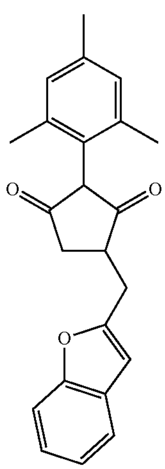 | δ ppm 1.92 (s, 3H) 2.08 (s, 3H) 2.26 (s, 3H) 2.61-2.67 (m, 1H) 2.84 (dd, 1H) 2.96-3.09 (m, 2H) 3.38 (dd, 1H) 6.48 (s, 1H) 6.89 (d, 2H) 7.16-7.26 (m, 2H) 7.39 (d, 1H) 7.49 (d, 1H) |
| T6 | 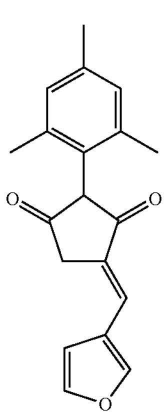 | δ ppm 2.11 (s, 3H) 2.15 (s, 6H) 3.37 (s, 2H) 6.60 (s, 1H) 6.92-6.98 (m, 3H) 7.47 (s, 1H) 7.64 (s, 1H) |
| T7 | 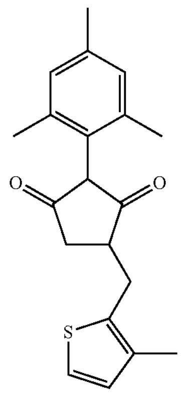 | δ ppm 1.9 (s, 3H), 2.19 (s, 3H), 2.2 (s, 3H), 2.5 (dd, 1H), 2.8 (dd, 2H), 3.03 (m, 2H), 3.3 (s, 3H), 6.78 (d, 1H), 6.83 (s, 1H), 6.85 (d, 2H), 7.10 (d, 1H) |
| T8 | 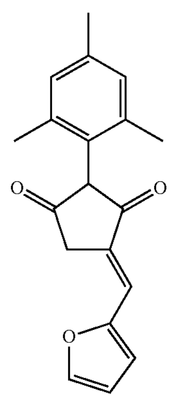 | δ ppm 2.12 (s, 6H) 2.30 (s, 3H) 3.50 (d, 2H) 6.85 (s, 1H) 6.95 (m, 3H) 7.37 (d, 1H), 7.53 (d, 1H) |
| T9 | 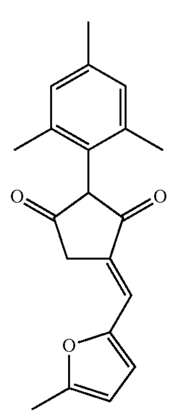 | δ ppm 2.12 (s, 6H) 2.29 (s, 3H) 2.36 (s, 3H) 3.49 (d, 2H) 6.09 (d, 1H) 6.43 (d, 1H) 6.78 (s, 1H) 6.94 (s, 2H) |

TABLE T1-continued
| Compound Number | Structure | ¹H nmr (CDCl₃ unless stated) or other physical data |
|---|---|---|
| T10 | 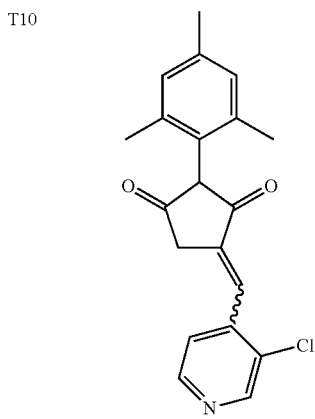 | LC-MS (Method C) ES⁻: 340, 338 (M − H)⁻. rt = 5.09 min |
| T11 | 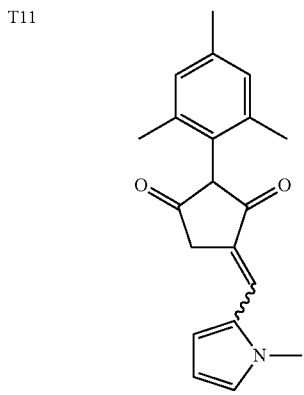 | LC-MS (Method C) ES⁻: (M − H)⁻ = 306. rt = 3.92 min |
| T12 | 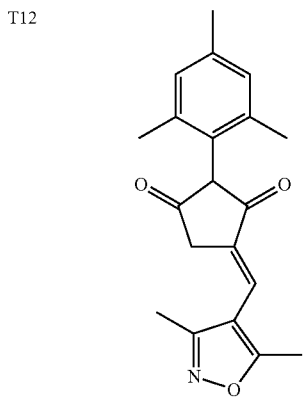 | LC-MS (Method C) ES⁺: MH⁺ = 326. rt = 3.53 min |
| T13 | 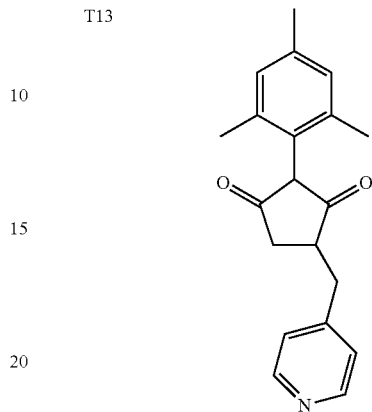 | LC-MS (Method C) ES⁺: MH⁺ = 308. rt = 2.42 min |
| T14 | 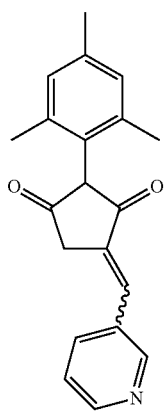 | LC-MS (Method C) ES⁺: MH⁺ = 306. rt = 2.94 min |
| T15 | 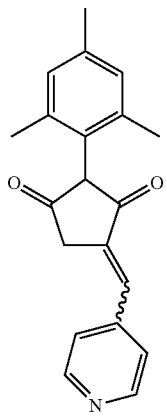 | LC-MS (Method C) ES⁺: MH⁺ = 306. rt = 2.56 min |

TABLE T1-continued
| Compound Number | Structure | ¹H nmr (CDCl₃ unless stated) or other physical data |
|---|---|---|
| T16 | 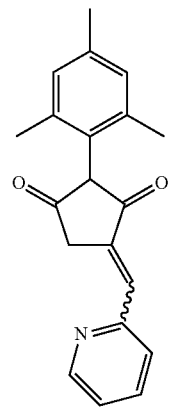 | LC-MS (Method C) ES⁺: MH⁺ = 306. rt = 3.24 min |
| T17 | 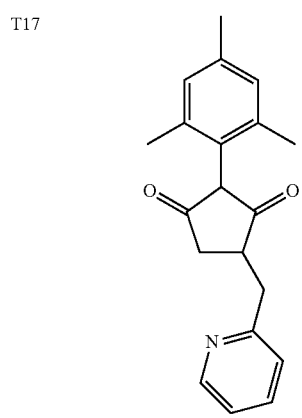 | LC-MS (Method C) ES⁺: MH⁺ = 308. rt = 2.96 min |
| T18 | 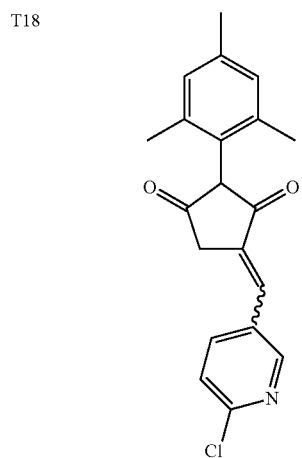 | LC-MS (Method C) ES⁻: 340, 338 (M − H)⁻. rt = 3.98 min |
| T19 | 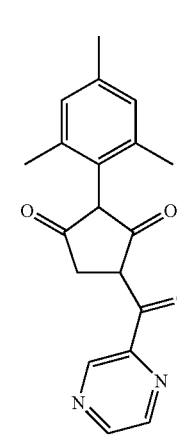 | LC-MS (Method C) ES⁻: (M − H)⁻ = 321. rt = 4.02 min |
| T20 | 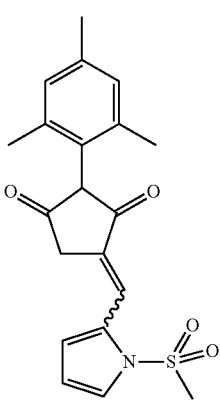 [SMILES: Cc1cc(C)c(C2C(=O)CC(=Cc3cccn3S(C)(=O)=O)C2=O)c(C)c1] | LC-MS (Method C) ES⁻: (M − H)⁻ = 371. rt = 3.86 min |
| T21 | 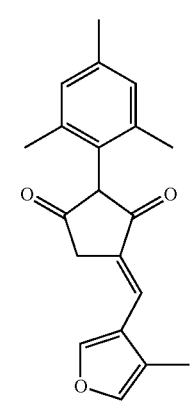 | LC-MS (Method A) ES⁺: MH⁺ = 309 r.t. = 1.63 m |

TABLE T1-continued

| Compound Number | Structure | ¹H nmr (CDCl₃ unless stated) or other physical data |
|---|---|---|
| T22 | 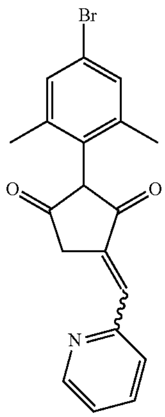 | LC-MS (Method C) ES⁺: 372, 370 (M + H)+ rt = 3.41 min |
| T23 | 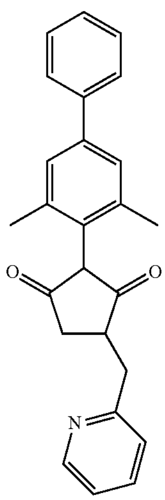 | LC-MS (Method C) ES⁺: MH⁺ = 370. rt = 3.59 min |
| T24 | 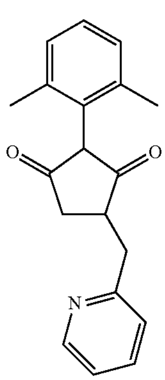 | LC-MS (Method C) ES⁺: MH⁺ = 294. rt = 2.58 min |
| T25 | | LC-MS (Method C) ES⁻: (M − H)⁻ = 320. rt = 2.81 min |
| T26 | | LC-MS (Method C) ES⁺: MH⁺ = 320. rt = 2.75 min |
| T27 | | LC-MS (Method C) ES⁻: 384, 382 (M − H)⁻. rt = 4.37 min |

| Compound Number | Structure | ¹H nmr (CDCl₃ unless stated) or other physical data |
|---|---|---|
| T28 | 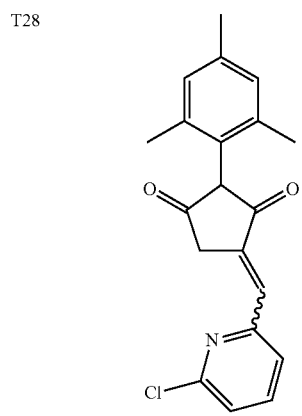 | LC-MS (Method C) ES⁻: 340, 338 (M − H)⁻. rt = 4.27 min |
| T29 | 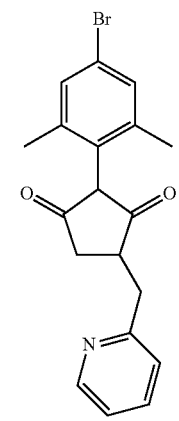 | LC-MS (Method C) ES⁺: 374, 372 (M + H)+ rt = 3.2 min |
| T30 | 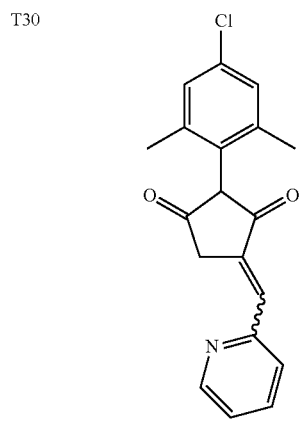 | LC-MS (Method C) ES⁻: 326, 324 (M − H)⁻. rt = 3.26 & 3.91 min |
| T31 | 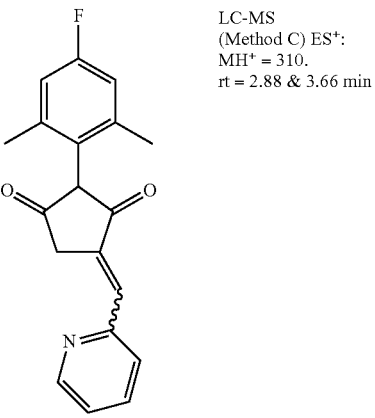 | LC-MS (Method C) ES⁺: MH⁺ = 310. rt = 2.88 & 3.66 min |
| T32 | 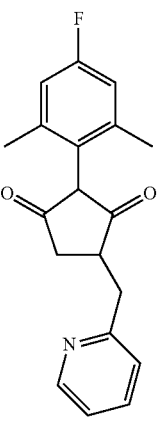 | LC-MS (Method C) ES⁺: MH⁺ = 312. rt = 2.72 min |
| T33 | 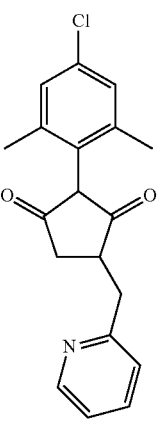 | LC-MS (Method C) ES⁻: 328, 326 (M − H)⁻. rt = 3.03 min |

TABLE T1-continued

| Compound Number | Structure | ¹H nmr (CDCl₃ unless stated) or other physical data |
|---|---|---|
| T34 | 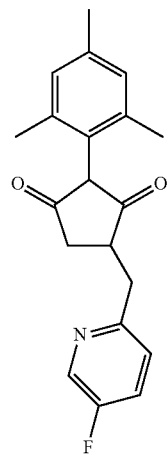 | LC-MS (Method C) ES⁺: MH⁺ = 326. rt = 3.71 min |
| T35 | 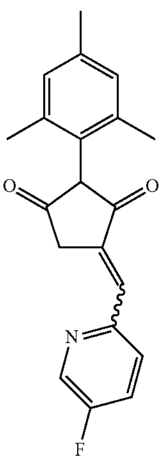 | LC-MS (Method C) ES⁺: MH⁺ = 324. rt = 4.01 min |
| T36 | 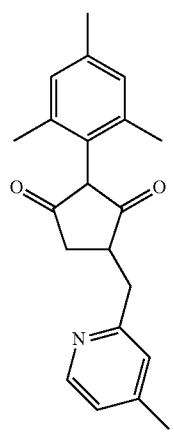 | LC-MS (Method C) ES⁺: MH⁺ = 322. rt = 2.78 min |

TABLE T1-continued

| Compound Number | Structure | ¹H nmr (CDCl₃ unless stated) or other physical data |
|---|---|---|
| T37 | 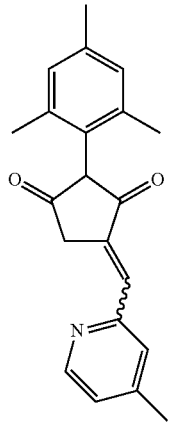 | LC-MS (Method C) ES⁺: MH⁺ = 320. rt = 2.84 & 3.91 min |
| T38 | 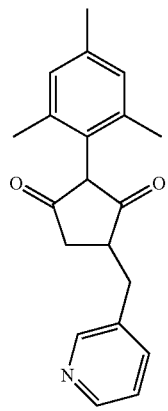 | δ ppm (CD₃OD) 1.92 (s, 3H), 2.04 (s, 3H), 2.24 (s, 3H), 2.45 (dd, 1H), 2.85 (dd, 1H), 3.10 (dd, 1H), 3.20 (m, 1H), 3.30 (dd, 1H), 6.85 (s, 1H), 6.87 (s, 1H), 7.92 (dd, 1H), 8.46 (d, 1H), 8.68 (d, 1H), 8.76 (s, 1H) |
| T39 | 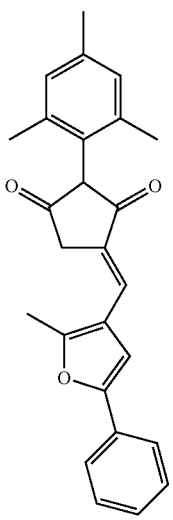 [SMILES: Cc1cc(C)c(C2C(=O)C/C(=C\c3cc(-c4ccccc4)oc3C)C2=O)c(C)c1] | LC-MS (Method A) ES⁺: MH⁺ = 385 r.t. = 1.91 m |

TABLE T1-continued

| Compound Number | Structure | ¹H nmr (CDCl₃ unless stated) or other physical data |
|---|---|---|
| T40 | 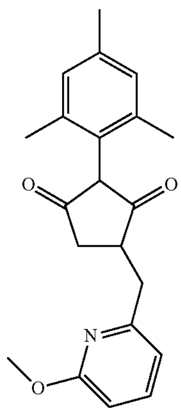 | LC-MS (Method C) ES⁻: (M − H)⁻ = 336. rt = 3.86 min |
| T41 | 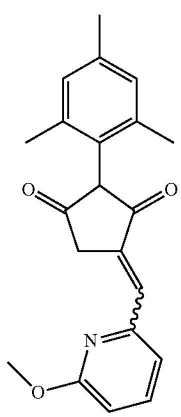 | LC-MS (Method C) ES⁺: MH⁺ = 336. rt = 4.12 & 4.24 min |
| T42 | 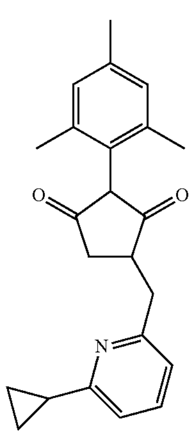 [SMILES: Cc1cc(C)c(C2C(=O)CC(Cc3cccc(C4CC4)n3)C2=O)c(C)c1] | LC-MS (Method C) ES⁻: (M − H)⁻ = 346. rt = 3.46 min |
| T43 | | LC-MS (Method C) ES⁺: MH⁺ = 382. rt = 4.33 min |
| T44 | | LC-MS (Method C) ES⁺: MH⁺ = 384. rt = 3.65 min |
| T45 | | LC-MS (Method C) ES⁺: 386, 384 (M + H)⁺ rt = 4.36 min |

TABLE T1-continued

| Compound Number | Structure | ¹H nmr (CDCl₃ unless stated) or other physical data |
|---|---|---|
| T46 | 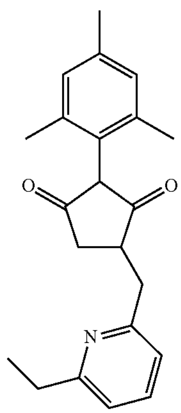 [SMILES: CCc1cccc(CC2CC(=O)C(c3c(C)cc(C)cc3C)C2=O)n1] | LC-MS (Method C) ES⁺: MH⁺ = 336. rt = 3.21 min |
| T47 | 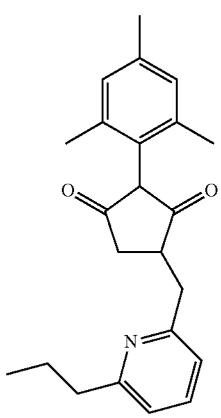 [SMILES: CCCc1cccc(CC2CC(=O)C(c3c(C)cc(C)cc3C)C2=O)n1] | LC-MS (Method C) ES⁺: MH⁺ = 350. rt = 3.43 min |
| T48 | 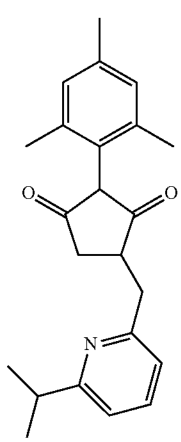 [SMILES: Cc1cc(C)c(C2C(=O)CC(Cc3cccc(C(C)C)n3)C2=O)c(C)c1] | LC-MS (Method C) ES⁺: MH⁺ = 350. rt = 3.51 min |
| T49 | 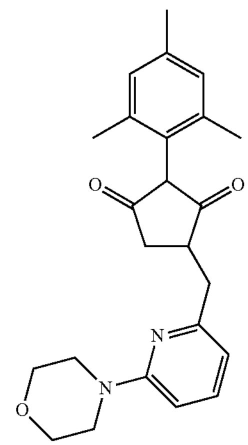 [SMILES: Cc1cc(C)c(C2C(=O)CC(Cc3cccc(N4CCOCC4)n3)C2=O)c(C)c1] | LC-MS (Method C) ES⁺: MH⁺ = 393. rt = 3.15 min |
| T50 | 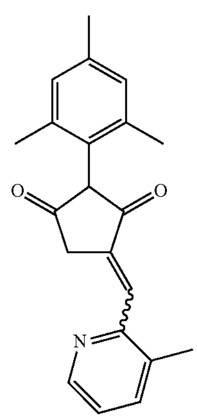 | LC-MS (Method C) ES⁺: MH⁺ = 320. rt = 3.46 min |
| T51 | 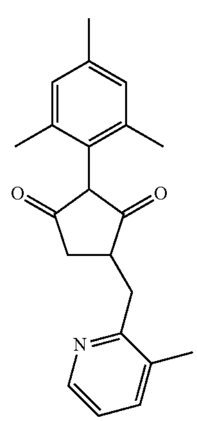 | LC-MS (Method C) ES⁺: MH⁺ = 322. rt = 3.05 min |

TABLE T1-continued
| Compound Number | Structure | ¹H nmr (CDCl₃ unless stated) or other physical data |
|---|---|---|
| T52 | 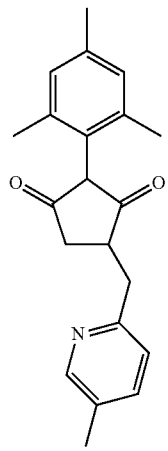 | LC-MS (Method C) ES⁺: MH⁺ = 322. rt = 2.94 min |
| T53 | 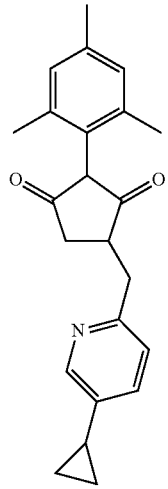 | LC-MS (Method C) ES⁺: MH⁺ = 348. rt = 3.34 min |
| T54 | 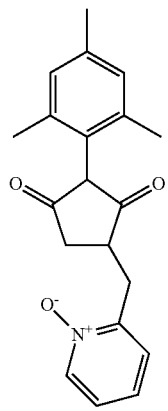 | LC-MS (Method C) ES⁺: MH⁺ = 324. rt = 2.99 min |
| T55 | 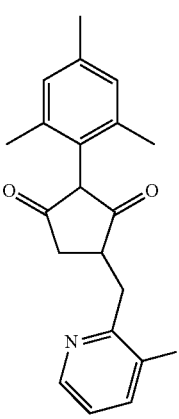 | LC-MS (Method C) ES⁺: MH⁺ = 326. rt = 3.68 min |
| T56 | 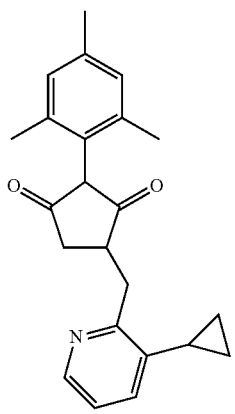 [SMILES: Cc1cc(C)c(C2C(=O)CC(Cc3ncccc3C3CC3)C2=O)c(C)c1] | LC-MS (Method C) ES⁺: MH⁺ = 348. rt = 3.33 min |
| T57 | 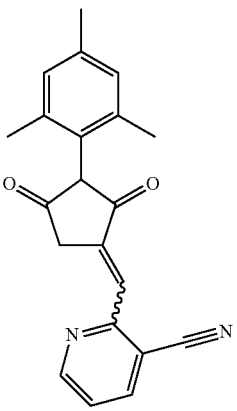 [SMILES: Cc1cc(C)c(C2C(=O)CC(=Cc3ncccc3C#N)C2=O)c(C)c1] | LC-MS (Method C) ES⁺: MH⁺ = 331. rt = 4.03 min |

TABLE T1-continued

| Compound Number | Structure | ¹H nmr (CDCl₃ unless stated) or other physical data |
|---|---|---|
| T58 | 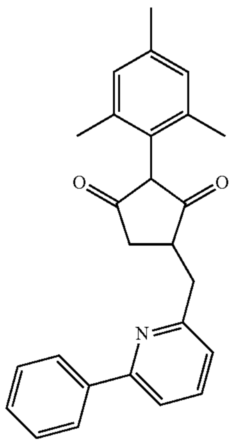 [SMILES: Cc1cc(C)c(C2C(=O)CC(Cc3cccc(-c4ccccc4)n3)C2=O)c(C)c1] | LC-MS (Method C) ES⁺: MH⁺ = 384. rt = 4.17 min |
| T59 | 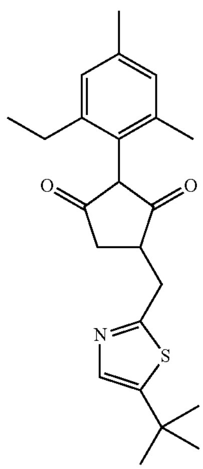 [SMILES: CCc1cc(C)cc(C)c1C1C(=O)CC(Cc2ncc(C(C)(C)C)s2)C1=O] | LC-MS (Method A) ES⁺: MH⁺ = 384. rt = 1.80 min |
| T60 | 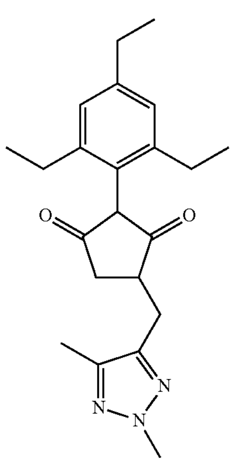 [SMILES: CCc1cc(CC)c(C2C(=O)CC(Cc3nn(C)nc3C)C2=O)c(CC)c1] | LC-MS (Method A) ES⁺: MH⁺ = 368. rt = 1.51 min |
| T61 | | LC-MS (Method A) ES⁺: MH⁺ = 416. rt = 1.61 min |
| T62 | | LC-MS (Method C) ES⁺: MH⁺ = 402. rt = 3.81 min |
| T63 | | LC-MS (Method C) ES⁺: MH⁺ = 400. rt = 4.48 min |

TABLE T1-continued
| Compound Number | Structure | ¹H nmr (CDCl₃ unless stated) or other physical data |
|---|---|---|
| T64 | 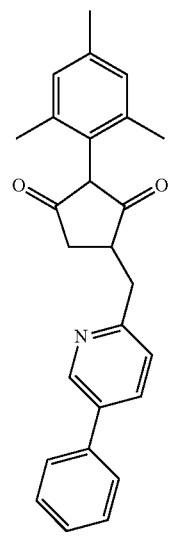 | LC-MS (Method C) ES⁺: MH⁺ = 384. rt = 3.99 min |
| T65 | 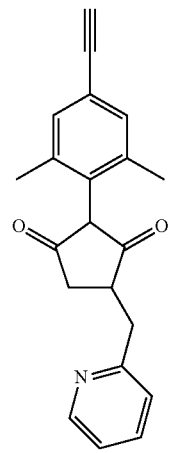 | LC-MS (Method C) ES⁺: MH⁺ = 318. rt = 2.98 min |
| T66 | 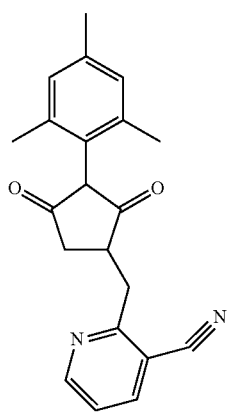 [SMILES: Cc1cc(C)c(C2C(=O)CC(Cc3ncccc3C#N)C2=O)c(C)c1] | LC-MS (Method C) ES⁺: MH⁺ = 333. rt = 3.56 min |
| T67 | 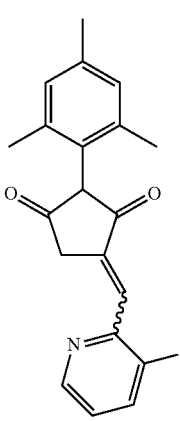 | LC-MS (Method C) ES⁺: 386, 384 (M + H)⁺ rt = 4.22 & 4.33 min |
| T68 | 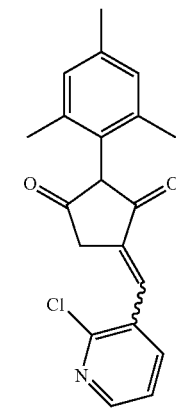 | LC-MS (Method C) ES⁻: 340, 338 (M − H)⁻. rt = 3.93 min |
| T69 | 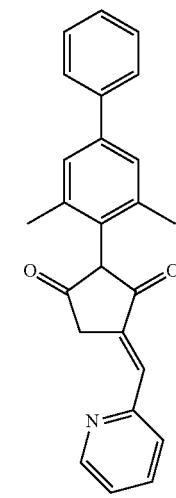 | LC-MS (Method C) ES⁺: MH⁺ = 368. rt = 3.87 min |

TABLE T1-continued
| Compound Number | Structure | ¹H nmr (CDCl₃ unless stated) or other physical data |
|---|---|---|
| T70 | 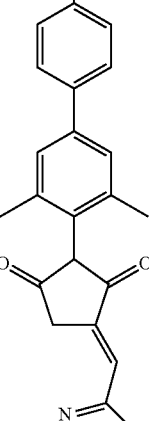 | LC-MS (Method C) ES⁺: MH⁺ = 386. rt = 3.86 min |
| T71 | 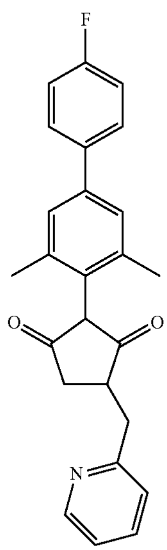 | LC-MS (Method C) ES⁺: MH⁺ = 388. rt = 3.59 min |
| T72 | 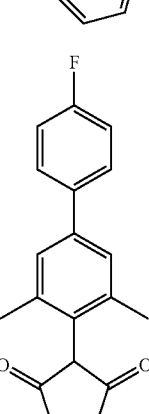 | LC-MS (Method C) ES⁺: MH⁺ = 334. rt = 3.39 min |
| T73 | | LC-MS (Method C) ES⁺: MH⁺ = 336. rt = 3.16 min |
| T74 | | LC-MS (Method C) ES⁺: MH⁺ = 336. rt = 3.37 min |
| T75 | 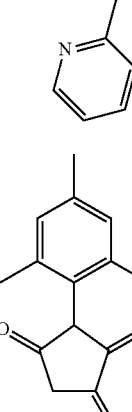 | LC-MS (Method C) ES⁺: MH⁺ = 319. rt = 2.49 min |

TABLE T1-continued
| Compound Number | Structure | $^1$H nmr (CDCl$_3$ unless stated) or other physical data |
|---|---|---|
| T76 | 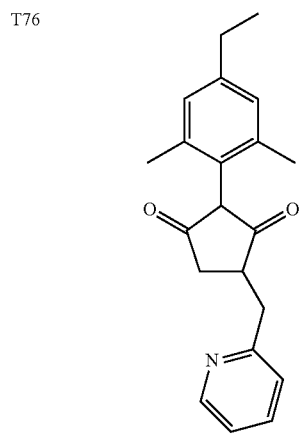 | LC-MS (Method C) ES$^+$: MH$^+$ = 322. rt = 3.08 min |
| T77 | 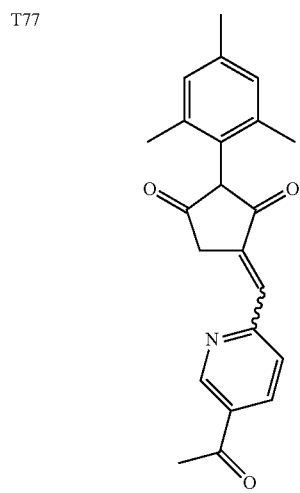 | LC-MS (Method C) ES$^-$: (M − H)$^-$ = 346. rt = 3.78 min |
| T78 | 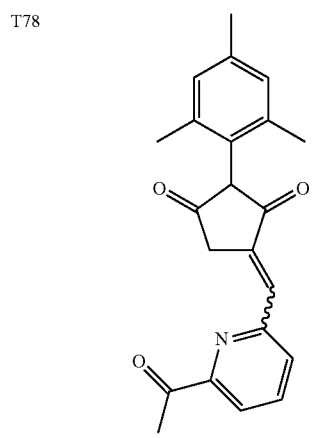 | LC-MS (Method C) ES$^+$: MH$^+$ = 348. rt = 3.83 min |
| T79 | 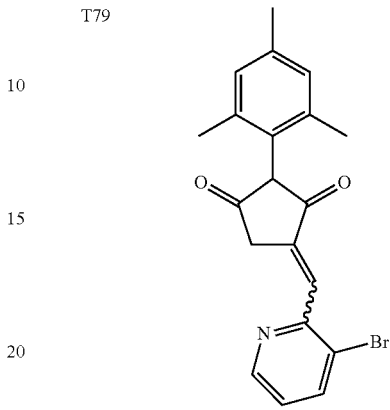 | LC-MS (Method C) ES$^+$: MH$^+$ = 386. rt = 4.22 & 4.33 min |
| T80 | 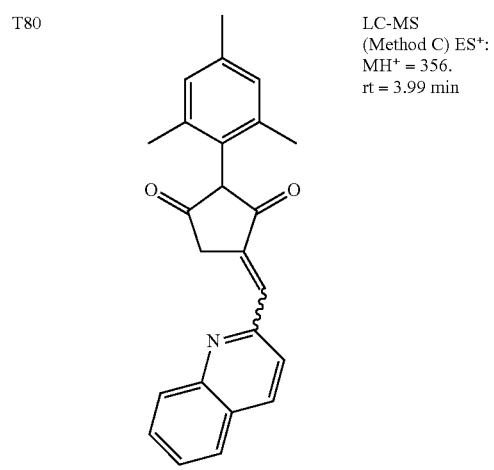 | LC-MS (Method C) ES$^+$: MH$^+$ = 356. rt = 3.99 min |
| T81 | 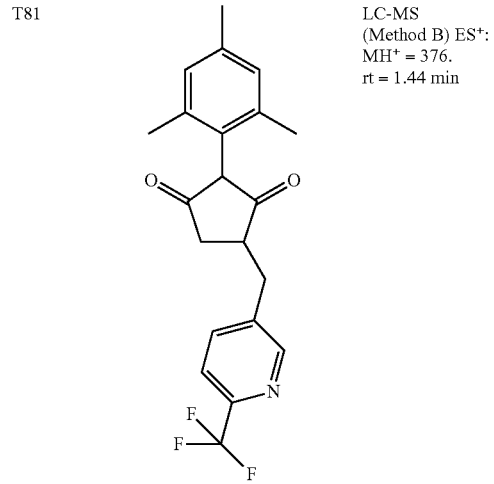 | LC-MS (Method B) ES$^+$: MH$^+$ = 376. rt = 1.44 min |

TABLE T1-continued
| Compound Number | Structure | ¹H nmr (CDCl₃ unless stated) or other physical data |
|---|---|---|
| T82 | 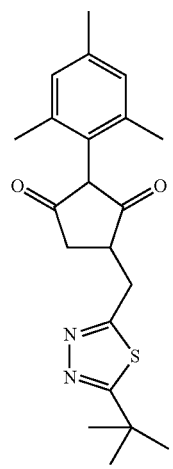 [SMILES: Cc1cc(C)c(C2C(=O)CC(Cc3nnc(C(C)(C)C)s3)C2=O)c(C)c1] | LC-MS (Method B) ES⁺: MH⁺ = 371. rt = 1.41 min |
| T83 | 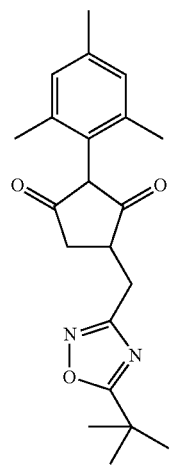 [SMILES: Cc1cc(C)c(C2C(=O)CC(Cc3noc(C(C)(C)C)n3)C2=O)c(C)c1] | LC-MS (Method B) ES⁺: MH⁺ = 355. rt = 1.46 min |
| T84 | 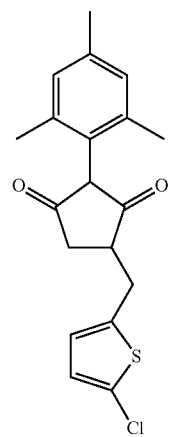 | LC-MS (Method B) ES⁺: MH⁺ = 347, 349. rt = 1.58 min |
| T85 | 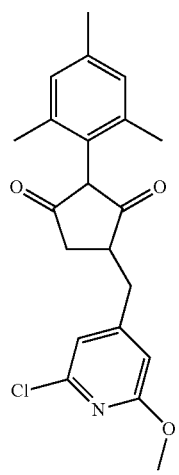 [SMILES: COc1cc(CC2CC(=O)C(c3c(C)cc(C)cc3C)C2=O)cc(Cl)n1] | LC-MS (Method B) ES⁺: MH⁺ = 372, 374. rt = 1.54 min |
| T86 | 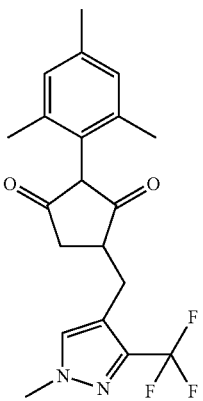 [SMILES: Cc1cc(C)c(C2C(=O)CC(Cc3cn(C)nc3C(F)(F)F)C2=O)c(C)c1] | LC-MS (Method B) ES⁺: MH⁺ = 379. rt = 1.42 min |
| T87 | 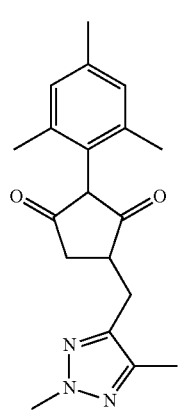 | LC-MS (Method B) ES⁺: MH⁺ = 326. rt = 1.19 min |

TABLE T1-continued
| Compound Number | Structure | $^1$H nmr (CDCl$_3$ unless stated) or other physical data |
|---|---|---|
| T88 | 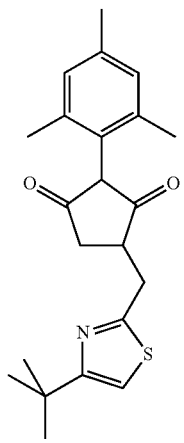 [SMILES: Cc1cc(C)c(C2C(=O)CC(Cc3nc(C(C)(C)C)cs3)C2=O)c(C)c1] | LC-MS (Method B) ES$^+$: MH$^+$ = 370. rt = 1.65 min |
| T89 | 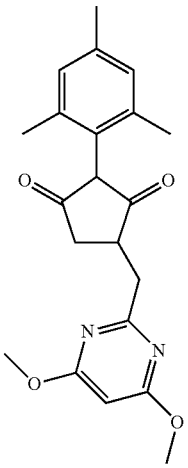 [SMILES: COc1cc(OC)nc(CC2CC(=O)C(c3c(C)cc(C)cc3C)C2=O)n1] | LC-MS (Method B) ES$^+$: MH$^+$ = 369. rt = 1.52 min |
| T90 | 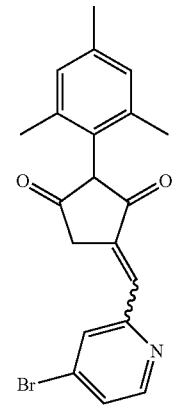 | LC-MS (Method C) ES$^+$: 386, 384 (M + H)+ rt = 4.24 min |
| T91 | 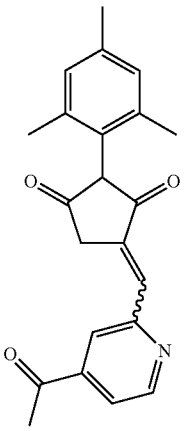 [SMILES: CC(=O)c1ccnc(C=C2CC(=O)C(c3c(C)cc(C)cc3C)C2=O)c1] | LC-MS (Method C) ES$^+$: MH$^+$ = 348. rt = 3.83 min |
| T92 | 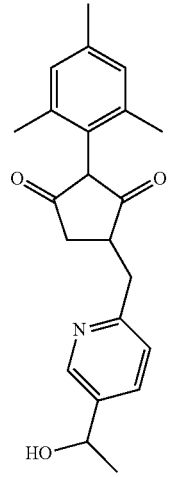 | LC-MS (Method C) ES$^+$: MH$^+$ = 352. rt = 2.8 min |
| T93 | 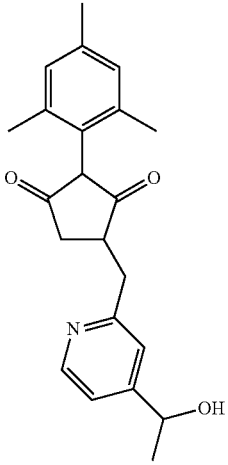 [SMILES: Cc1cc(C)c(C2C(=O)CC(Cc3cc(C(C)O)ccn3)C2=O)c(C)c1] | LC-MS (Method C) ES$^+$: MH$^+$ = 352. rt = 2.69 min |

TABLE T1-continued
| Compound Number | Structure | ¹H nmr (CDCl₃ unless stated) or other physical data |
|---|---|---|
| T94 | 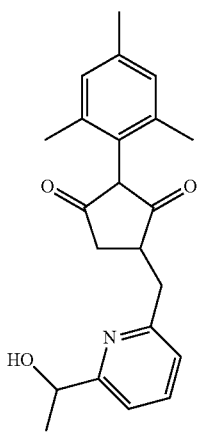 | LC-MS (Method C) ES⁺: MH⁺ = 352. rt = 3.02 min |
| T95 | 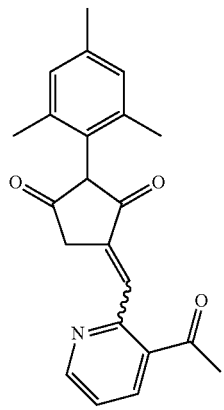 [SMILES: CC(=O)c1cccnc1C=C1CC(=O)C(c2c(C)cc(C)cc2C)C1=O] | LC-MS (Method C) ES⁺: MH⁺ = 348. rt = 3.8 min |
| T96 | 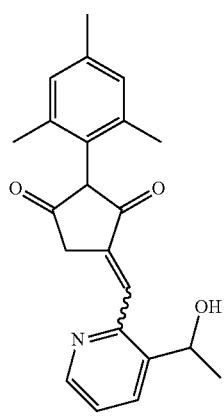 [SMILES: Cc1cc(C)c(C2C(=O)CC(=Cc3ncccc3C(C)O)C2=O)c(C)c1] | LC-MS (Method C) ES⁺: MH⁺ = 350. rt = 3.13 & 3.59 min |
| T97 | 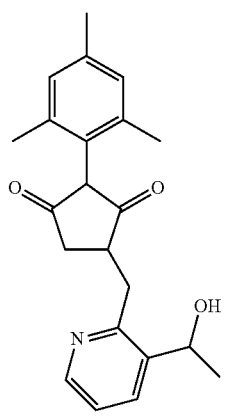 [SMILES: Cc1cc(C)c(C2C(=O)CC(Cc3ncccc3C(C)O)C2=O)c(C)c1] | LC-MS (Method C) ES⁺: MH⁺ = 352. rt = 2.89 & 3.00 min |
| T98 | 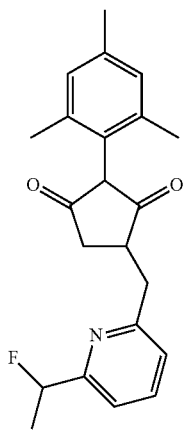 | LC-MS (Method C) ES⁺: MH⁺ = 354. rt = 3.83 min |
| T99 | 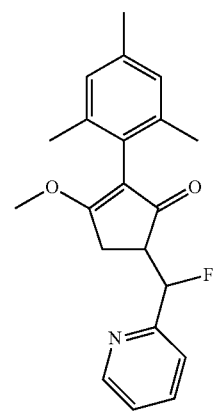 [SMILES: COC1=C(c2c(C)cc(C)cc2C)C(=O)C(C(F)c2ccccn2)C1] | LC-MS (Method C) ES⁺: MH⁺ = 340. rt = 3.9 min |

TABLE T1-continued

| Compound Number | Structure | ¹H nmr (CDCl₃ unless stated) or other physical data |
|---|---|---|
| T100 | 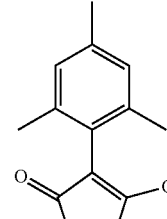 | LC-MS (Method C) ES⁺: MH⁺ = 338. rt = 2.14 min |
| T101 | 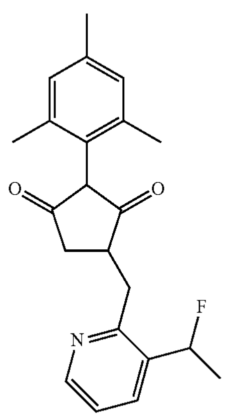 [SMILES: Cc1cc(C)c(C2C(=O)CC(Cc3ncccc3C(C)F)C2=O)c(C)c1] | LC-MS (Method C) ES⁺: MH⁺ = 354. rt = 3.74 min |
| T102 | 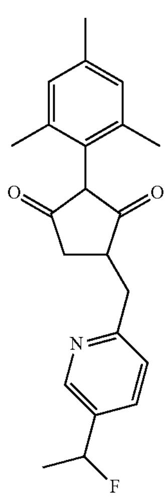 | LC-MS (Method C) ES⁺: MH⁺ = 354. rt = 3.64 min |
| T103 | 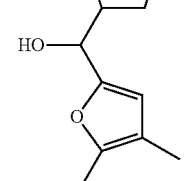 | LC-MS (Method C) ES⁺: MH⁺ = 354. rt = 3.49 min |

TABLE P1

| Compound Number | Structure | ¹H nmr (CDCl₃ unless stated) or other physical data |
|---|---|---|
| P1 | 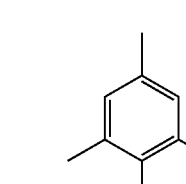 | δ ppm 1.92 (s, 3H) 2.05 (s, 3H) 2.10 (s, 3H) 2.20 (s, 3H) 2.26 (s, 3H) 2.45 (dd, 1H) 2.82 (dd, 1H) 3.17 (ddd, 1H) 4.71 (d, 1H) 4.95 (s, 1H) 6.12 (s, 1H) 6.87 (s, 2H) |
| P2 | 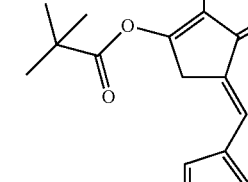 | δ ppm 1.12 (s, 9H), 2.09 (s, 6H) 2.26 (s, 3H) 3.81 (s, 2H) 6.62 (s, 1H) 6.83 (s, 2H) 7.41 (s, 1H) 7.52 (s, 1H) 7.78 (s, 1H) |

TABLE P1-continued

| Compound Number | Structure | ¹H nmr (CDCl₃ unless stated) or other physical data |
|---|---|---|
| P3 | 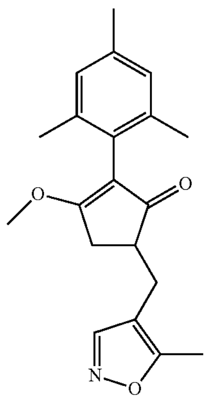 | LC-MS (Method A) ES⁺: MH⁺ = 326 r.t. = 1.54 m |
| P4 | 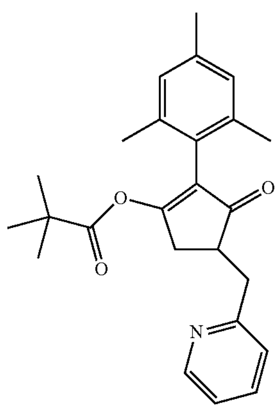 [SMILES: Cc1cc(C)c(C2=C(OC(=O)C(C)(C)C)CC(Cc3ccccn3)C2=O)c(C)c1] | LC-MS (Method C) ES⁺: MH⁺ = 392. rt = 3.71 min |
| P5 | 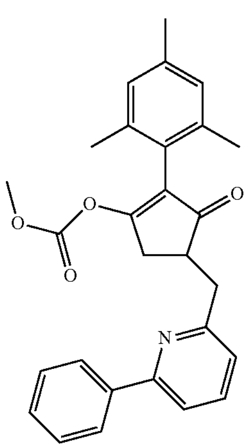 | LC-MS (Method C) ES⁺: MH⁺ = 442. rt = 4.54 min |
| P6 | | LC-MS (Method A) ES⁺: MH⁺ = 488. rt = 2.23 min |
| P7 | | LC-MS (Method C) ES⁺: MH⁺ = 339. rt = 3.24 min |
| P8 | | LC-MS (Method C) ES⁺: MH⁺ = 406. rt = 3.64 min |

TABLE P1-continued
| Compound Number | Structure | $^1$H nmr (CDCl$_3$ unless stated) or other physical data |
|---|---|---|
| P9 | 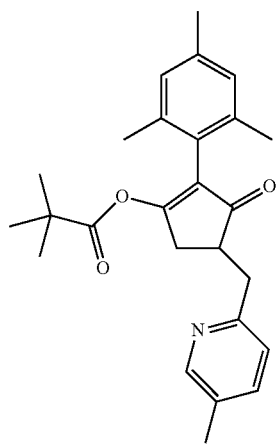 [SMILES: Cc1ccc(CC2CC(OC(=O)C(C)(C)C)=C(c3c(C)cc(C)cc3C)C2=O)nc1] | LC-MS (Method C) ES$^+$: MH$^+$ = 406. rt = 3.61 min |
| P10 | 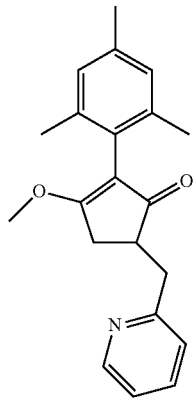 | LC-MS (Method C) ES$^+$: MH$^+$ = 322. rt = 2.84 min |
| P11 | 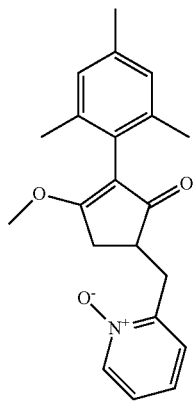 | LC-MS (Method C) ES$^+$: MH$^+$ = 338. rt = 3.17 min |
| P12 | 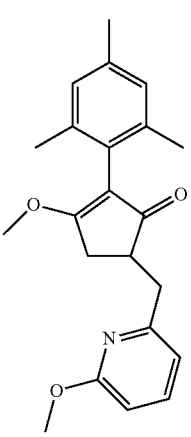 | LC-MS (Method C) ES$^+$: MH$^+$ = 352. rt = 4.26 min |
| P13 | 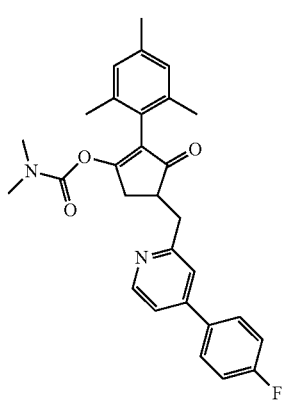 [SMILES: Cc1cc(C)c(C2=C(OC(=O)N(C)C)CC(Cc3cc(-c4ccc(F)cc4)ccn3)C2=O)c(C)c1] | LC-MS (Method C) ES$^+$: MH$^+$ = 473. rt = 3.73 min |
| P14 | 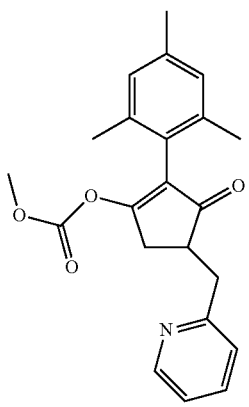 | LC-MS (Method C) ES$^+$: MH$^+$ = 366. rt = 3.09 min |

TABLE P1-continued

| Compound Number | Structure | ¹H nmr (CDCl₃ unless stated) or other physical data |
|---|---|---|
| P15 | 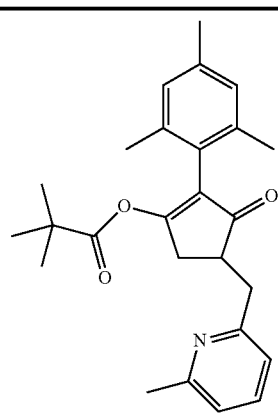 | LC-MS (Method C) ES⁺: MH⁺ = 406. rt = 3.35 min |
| P16 | 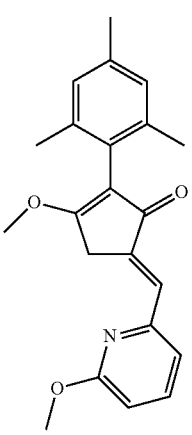 | LC-MS (Method C) ES⁺: MH⁺ = 350. rt = 4.59 min |

The compounds of the following Tables 1 to 58 can be obtained in an analogous manner. Table 1 covers 1731 compounds of structural type T-1:

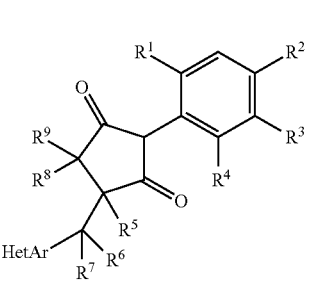

wherein $R^1$ and $R^3$ are methyl and $R^2$ and $R^4$ are hydrogen and where $R^5$, $R^6$, $R^7$, $R^8$, $R^9$ and HetAr are defined in the table below:

| Compound number | R⁵ | R⁶ | R⁷ | R⁸ | R⁹ | HetAr |
|---|---|---|---|---|---|---|
| 1 | H | H | H | H | H | 2-pyridyl |
| 2 | H | H | H | H | H | 3-fluoro-2-pyridyl |
| 3 | H | H | H | H | H | 4-fluoro-2-pyridyl |
| 4 | H | H | H | H | H | 5-fluoro-2-pyridyl |
| 5 | H | H | H | H | H | 6-fluoro-2-pyridyl |
| 6 | H | H | H | H | H | 3-chloro-2-pyridyl |
| 7 | H | H | H | H | H | 4-chloro-2-pyridyl |
| 8 | H | H | H | H | H | 5-chloro-2-pyridyl |
| 9 | H | H | H | H | H | 6-chloro-2-pyridyl |
| 10 | H | H | H | H | H | 3-methyl-2-pyridyl |
| 11 | H | H | H | H | H | 4-methyl-2-pyridyl |
| 12 | H | H | H | H | H | 5-methyl-2-pyridyl |
| 13 | H | H | H | H | H | 6-methyl-2-pyridyl |
| 14 | H | H | H | H | H | 3-trifluoromethyl-2-pyridyl |
| 15 | H | H | H | H | H | 4-trifluoromethyl-2-pyridyl |
| 16 | H | H | H | H | H | 5-trifluoromethyl-2-pyridyl |
| 17 | H | H | H | H | H | 6-trifluoromethyl-2-pyridyl |
| 18 | H | H | H | H | H | 3-methoxy-2-pyridyl |
| 19 | H | H | H | H | H | 4-methoxy-2-pyridyl |
| 20 | H | H | H | H | H | 5-methoxy-2-pyridyl |
| 21 | H | H | H | H | H | 6-methoxy-2-pyridyl |
| 22 | H | H | H | H | H | 3-trifluoromethoxy-2-pyridyl |
| 23 | H | H | H | H | H | 4-trifluoromethoxy-2-pyridyl |
| 24 | H | H | H | H | H | 5-trifluoromethoxy-2-pyridyl |
| 25 | H | H | H | H | H | 6-trifluoromethoxy-2-pyridyl |
| 26 | H | H | H | H | H | 3-cyano-2-pyridyl |
| 27 | H | H | H | H | H | 4-cyano-2-pyridyl |
| 28 | H | H | H | H | H | 5-cyano-2-pyridyl |
| 29 | H | H | H | H | H | 6-cyano-2-pyridyl |
| 30 | H | H | H | H | H | 3-nitro-2-pyridyl |
| 31 | H | H | H | H | H | 4-nitro-2-pyridyl |
| 32 | H | H | H | H | H | 5-nitro-2-pyridyl |
| 33 | H | H | H | H | H | 6-nitro-2-pyridyl |
| 34 | H | H | H | H | H | 3-methanesulfonyl-2-pyridyl |
| 35 | H | H | H | H | H | 4-methanesulfonyl-2-pyridyl |
| 36 | H | H | H | H | H | 5-methanesulfonyl-2-pyridyl |
| 37 | H | H | H | H | H | 6-methanesulfonyl-2-pyridyl |
| 38 | H | H | H | H | H | 3-pyridyl |
| 39 | H | H | H | H | H | 2-fluoro-3-pyridyl |
| 40 | H | H | H | H | H | 4-fluoro-3-pyridyl |
| 41 | H | H | H | H | H | 5-fluoro-3-pyridyl |
| 42 | H | H | H | H | H | 6-fluoro-3-pyridyl |
| 43 | H | H | H | H | H | 2-chloro-3-pyridyl |
| 44 | H | H | H | H | H | 4-chloro-3-pyridyl |
| 45 | H | H | H | H | H | 5-chloro-3-pyridyl |
| 46 | H | H | H | H | H | 6-chloro-3-pyridyl |
| 47 | H | H | H | H | H | 2-bromo-3-pyridyl |
| 48 | H | H | H | H | H | 4-bromo-3-pyridyl |
| 49 | H | H | H | H | H | 5-bromo-3-pyridyl |
| 50 | H | H | H | H | H | 6-bromo-3-pyridyl |
| 51 | H | H | H | H | H | 2-methoxy-3-pyridyl |
| 52 | H | H | H | H | H | 4-methoxy-3-pyridyl |
| 53 | H | H | H | H | H | 5-methoxy-3-pyridyl |
| 54 | H | H | H | H | H | 6-methoxy-3-pyridyl |
| 55 | H | H | H | H | H | 2-trifluoromethoxy-3-pyridyl |
| 56 | H | H | H | H | H | 4-trifluoromethoxy-3-pyridyl |
| 57 | H | H | H | H | H | 5-trifluoromethoxy-3-pyridyl |
| 58 | H | H | H | H | H | 6-trifluoromethoxy-3-pyridyl |
| 59 | H | H | H | H | H | 2-methyl-3-pyridyl |
| 60 | H | H | H | H | H | 4-methyl-3-pyridyl |
| 61 | H | H | H | H | H | 5-methyl-3-pyridyl |
| 62 | H | H | H | H | H | 6-methyl-3-pyridyl |
| 63 | H | H | H | H | H | 2-trifluoromethyl-3-pyridyl |
| 64 | H | H | H | H | H | 4-trifluoromethyl-3-pyridyl |
| 65 | H | H | H | H | H | 5-trifluoromethyl-3-pyridyl |

| Compound number | R⁵ | R⁶ | R⁷ | R⁸ | R⁹ | HetAr |
|---|---|---|---|---|---|---|
| 66 | H | H | H | H | H | 6-trifluoromethyl-3-pyridyl |
| 67 | H | H | H | H | H | 2-cyano-3-pyridyl |
| 68 | H | H | H | H | H | 4-cyano-3-pyridyl |
| 69 | H | H | H | H | H | 5-cyano-3-pyridyl |
| 70 | H | H | H | H | H | 6-cyano-3-pyridyl |
| 71 | H | H | H | H | H | 2-nitro-3-pyridyl |
| 72 | H | H | H | H | H | 4-nitro-3-pyridyl |
| 73 | H | H | H | H | H | 5-nitro-3-pyridyl |
| 74 | H | H | H | H | H | 6-nitro-3-pyridyl |
| 75 | H | H | H | H | H | 2-methanesulfonyl-3-pyridyl |
| 76 | H | H | H | H | H | 4-methanesulfonyl-3-pyridyl |
| 77 | H | H | H | H | H | 5-methanesulfonyl-3-pyridyl |
| 78 | H | H | H | H | H | 6-methanesulfonyl-3-pyridyl |
| 79 | H | H | H | H | H | 4-pyridyl |
| 80 | H | H | H | H | H | 2-fluoro-4-pyridyl |
| 81 | H | H | H | H | H | 3-fluoro-4-pyridyl |
| 82 | H | H | H | H | H | 2-chloro-4-pyridyl |
| 83 | H | H | H | H | H | 3-chloro-4-pyridyl |
| 84 | H | H | H | H | H | 2-bromo-4-pyridyl |
| 85 | H | H | H | H | H | 3-bromo-4-pyridyl |
| 86 | H | H | H | H | H | 2-methoxy-4-pyridyl |
| 87 | H | H | H | H | H | 3-methoxy-4-pyridyl |
| 88 | H | H | H | H | H | 2-trifluoromethoxy-4-pyridyl |
| 89 | H | H | H | H | H | 3-trifluoromethoxy-4-pyridyl |
| 90 | H | H | H | H | H | 2-methyl-4-pyridyl |
| 91 | H | H | H | H | H | 3-methyl-4-pyridyl |
| 92 | H | H | H | H | H | 2-trifluoromethyl-4-pyridyl |
| 93 | H | H | H | H | H | 3-trifluoromethyl-4-pyridyl |
| 94 | H | H | H | H | H | 2-cyano-4-pyridyl |
| 95 | H | H | H | H | H | 3-cyano-4-pyridyl |
| 96 | H | H | H | H | H | 2-nitro-4-pyridyl |
| 97 | H | H | H | H | H | 3-nitro-4-pyridyl |
| 98 | H | H | H | H | H | 2-methanesulfonyl-4-pyridyl |
| 99 | H | H | H | H | H | 3-methanesulfonyl-4-pyridyl |
| 100 | H | H | H | H | H | 2-pyridazinyl |
| 101 | H | H | H | H | H | 4-fluoro-2-pyridazinyl |
| 102 | H | H | H | H | H | 5-fluoro-2-pyridazinyl |
| 103 | H | H | H | H | H | 6-fluoro-2-pyridazinyl |
| 104 | H | H | H | H | H | 4-chloro-2-pyridazinyl |
| 105 | H | H | H | H | H | 5-chloro-2-pyridazinyl |
| 106 | H | H | H | H | H | 6-chloro-2-pyridazinyl |
| 107 | H | H | H | H | H | 4-bromo-2-pyridazinyl |
| 108 | H | H | H | H | H | 5-bromo-2-pyridazinyl |
| 109 | H | H | H | H | H | 6-bromo-2-pyridazinyl |
| 110 | H | H | H | H | H | 4-methoxy-2-pyridazinyl |
| 111 | H | H | H | H | H | 5-methoxy-2-pyridazinyl |
| 112 | H | H | H | H | H | 6-methoxy-2-pyridazinyl |
| 113 | H | H | H | H | H | 4-trifluoromethoxy-2-pyridazinyl |
| 114 | H | H | H | H | H | 5-trifluoromethoxy-2-pyridazinyl |
| 115 | H | H | H | H | H | 6-trifluoromethoxy-2-pyridazinyl |
| 116 | H | H | H | H | H | 4-methyl-2-pyridazinyl |
| 117 | H | H | H | H | H | 5-methyl-2-pyridazinyl |
| 118 | H | H | H | H | H | 6-methyl-2-pyridazinyl |
| 119 | H | H | H | H | H | 4-trifluoromethyl-2-pyridazinyl |
| 120 | H | H | H | H | H | 5-trifluoromethyl-2-pyridazinyl |
| 121 | H | H | H | H | H | 6-trifluoromethyl-2-pyridazinyl |
| 122 | H | H | H | H | H | 4-cyano-2-pyridazinyl |
| 123 | H | H | H | H | H | 5-cyano-2-pyridazinyl |
| 124 | H | H | H | H | H | 6-cyano-2-pyridazinyl |
| 125 | H | H | H | H | H | 4-nitro-2-pyridazinyl |
| 126 | H | H | H | H | H | 5-nitro-2-pyridazinyl |
| 127 | H | H | H | H | H | 6-nitro-2-pyridazinyl |
| 128 | H | H | H | H | H | 4-methanesulfonyl-2-pyridazinyl |
| 129 | H | H | H | H | H | 5-methanesulfonyl-2-pyridazinyl |
| 130 | H | H | H | H | H | 6-methanesulfonyl-2-pyridazinyl |
| 131 | H | H | H | H | H | 3-pyridazinyl |
| 132 | H | H | H | H | H | 2-fluoro-3-pyridazinyl |
| 133 | H | H | H | H | H | 5-fluoro-3-pyridazinyl |
| 134 | H | H | H | H | H | 6-fluoro-3-pyridazinyl |
| 135 | H | H | H | H | H | 2-chloro-3-pyridazinyl |
| 136 | H | H | H | H | H | 5-chloro-3-pyridazinyl |
| 137 | H | H | H | H | H | 6-chloro-3-pyridazinyl |
| 138 | H | H | H | H | H | 2-bromo-3-pyridazinyl |
| 139 | H | H | H | H | H | 5-bromo-3-pyridazinyl |
| 140 | H | H | H | H | H | 6-bromo-3-pyridazinyl |
| 141 | H | H | H | H | H | 2-methoxy-3-pyridazinyl |
| 142 | H | H | H | H | H | 5-methoxy-3-pyridazinyl |
| 143 | H | H | H | H | H | 6-methoxy-3-pyridazinyl |
| 144 | H | H | H | H | H | 2-trifluoromethoxy-3-pyridazinyl |
| 145 | H | H | H | H | H | 5-trifluoromethoxy-3-pyridazinyl |
| 146 | H | H | H | H | H | 6-trifluoromethoxy-3-pyridazinyl |
| 147 | H | H | H | H | H | 2-methyl-3-pyridazinyl |
| 148 | H | H | H | H | H | 5-methyl-3-pyridazinyl |
| 149 | H | H | H | H | H | 6-methyl-3-pyridazinyl |
| 150 | H | H | H | H | H | 2-trifluoromethyl-3-pyridazinyl |
| 151 | H | H | H | H | H | 5-trifluoromethyl-3-pyridazinyl |
| 152 | H | H | H | H | H | 6-trifluoromethyl-3-pyridazinyl |
| 153 | H | H | H | H | H | 2-cyano-3-pyridazinyl |
| 154 | H | H | H | H | H | 5-cyano-3-pyridazinyl |
| 155 | H | H | H | H | H | 6-cyano-3-pyridazinyl |
| 156 | H | H | H | H | H | 2-nitro-3-pyridazinyl |
| 157 | H | H | H | H | H | 5-nitro-3-pyridazinyl |
| 158 | H | H | H | H | H | 6-nitro-3-pyridazinyl |
| 159 | H | H | H | H | H | 2-methanesulfonyl-3-pyridazinyl |
| 160 | H | H | H | H | H | 5-methanesulfonyl-3-pyridazinyl |
| 161 | H | H | H | H | H | 6-methanesulfonyl-3-pyridazinyl |
| 162 | H | H | H | H | H | 2-pyrimidyl |
| 163 | H | H | H | H | H | 4-fluoro-2-pyrimidyl |
| 164 | H | H | H | H | H | 5-fluoro-2-pyrimidyl |
| 165 | H | H | H | H | H | 4-chloro-2-pyrimidyl |
| 166 | H | H | H | H | H | 5-chloro-2-pyrimidyl |
| 167 | H | H | H | H | H | 4-bromo-2-pyrimidyl |
| 168 | H | H | H | H | H | 5-bromo-2-pyrimidyl |
| 169 | H | H | H | H | H | 4-methoxy-2-pyrimidyl |
| 170 | H | H | H | H | H | 5-methoxy-2-pyrimidyl |
| 171 | H | H | H | H | H | 4-trifluoromethoxy-2-pyrimidyl |
| 172 | H | H | H | H | H | 5-trifluoromethoxy-2-pyrimidyl |
| 173 | H | H | H | H | H | 4-methyl-2-pyrimidyl |
| 174 | H | H | H | H | H | 5-methyl-2-pyrimidyl |
| 175 | H | H | H | H | H | 4-trifluoromethyl-2-pyrimidyl |
| 176 | H | H | H | H | H | 5-trifluoromethyl-2-pyrimidyl |
| 177 | H | H | H | H | H | 4-cyano-2-pyrimidyl |
| 178 | H | H | H | H | H | 5-cyano-2-pyrimidyl |
| 179 | H | H | H | H | H | 4-nitro-2-pyrimidyl |
| 180 | H | H | H | H | H | 5-nitro-2-pyrimidyl |
| 181 | H | H | H | H | H | 4-methanesulfonyl-2-pyrimidyl |
| 182 | H | H | H | H | H | 5-methanesulfonyl-2-pyrimidyl |
| 183 | H | H | H | H | H | 4-pyrimidyl |
| 184 | H | H | H | H | H | 2-fluoro-4-pyrimidyl |
| 185 | H | H | H | H | H | 5-fluoro-4-pyrimidyl |

-continued

| Compound number | R⁵ | R⁶ | R⁷ | R⁸ | R⁹ | HetAr |
|---|---|---|---|---|---|---|
| 186 | H | H | H | H | H | 6-fluoro-4-pyrimidyl |
| 187 | H | H | H | H | H | 2-chloro-4-pyrimidyl |
| 188 | H | H | H | H | H | 5-chloro-4-pyrimidyl |
| 189 | H | H | H | H | H | 6-chloro-4-pyrimidyl |
| 190 | H | H | H | H | H | 2-bromo-4-pyrimidyl |
| 191 | H | H | H | H | H | 5-bromo-4-pyrimidyl |
| 192 | H | H | H | H | H | 6-bromo-4-pyrimidyl |
| 193 | H | H | H | H | H | 2-methoxy-4-pyrimidyl |
| 194 | H | H | H | H | H | 5-methoxy-4-pyrimidyl |
| 195 | H | H | H | H | H | 6-methoxy-4-pyrimidyl |
| 196 | H | H | H | H | H | 2-trifluoromethoxy-4-pyrimidyl |
| 197 | H | H | H | H | H | 5-trifluoromethoxy-4-pyrimidyl |
| 198 | H | H | H | H | H | 6-trifluoromethoxy-4-pyrimidyl |
| 199 | H | H | H | H | H | 2-methyl-4-pyrimidyl |
| 200 | H | H | H | H | H | 5-methyl-4-pyrimidyl |
| 201 | H | H | H | H | H | 6-methyl-4-pyrimidyl |
| 202 | H | H | H | H | H | 2-trifluoromethyl-4-pyrimidyl |
| 203 | H | H | H | H | H | 5-trifluoromethyl-4-pyrimidyl |
| 204 | H | H | H | H | H | 6-trifluoromethyl-4-pyrimidyl |
| 205 | H | H | H | H | H | 2-cyano-4-pyrimidyl |
| 206 | H | H | H | H | H | 5-cyano-4-pyrimidyl |
| 207 | H | H | H | H | H | 6-cyano-4-pyrimidyl |
| 208 | H | H | H | H | H | 2-nitro-4-pyrimidyl |
| 209 | H | H | H | H | H | 5-nitro-4-pyrimidyl |
| 210 | H | H | H | H | H | 6-nitro-4-pyrimidyl |
| 211 | H | H | H | H | H | 2-methanesulfonyl-4-pyrimidyl |
| 212 | H | H | H | H | H | 5-methanesulfonyl-4-pyrimidyl |
| 213 | H | H | H | H | H | 6-methanesulfonyl-4-pyrimidyl |
| 214 | H | H | H | H | H | 5-pyrimidyl |
| 215 | H | H | H | H | H | 2-fluoro-5-pyrimidyl |
| 216 | H | H | H | H | H | 4-fluoro-5-pyrimidyl |
| 217 | H | H | H | H | H | 2-chloro-5-pyrimidyl |
| 218 | H | H | H | H | H | 4-chloro-5-pyrimidyl |
| 219 | H | H | H | H | H | 2-bromo-5-pyrimidyl |
| 220 | H | H | H | H | H | 4-bromo-5-pyrimidyl |
| 221 | H | H | H | H | H | 2-methoxy-5-pyrimidyl |
| 222 | H | H | H | H | H | 4-methoxy-5-pyrimidyl |
| 223 | H | H | H | H | H | 2-trifluoromethoxy-5-pyrimidyl |
| 224 | H | H | H | H | H | 4-trifluoromethoxy-5-pyrimidyl |
| 225 | H | H | H | H | H | 2-methyl-5-pyrimidyl |
| 226 | H | H | H | H | H | 4-methyl-5-pyrimidyl |
| 227 | H | H | H | H | H | 2-trifluoromethyl-5-pyrimidyl |
| 228 | H | H | H | H | H | 4-trifluoromethyl-5-pyrimidyl |
| 229 | H | H | H | H | H | 2-cyano-5-pyrimidyl |
| 230 | H | H | H | H | H | 4-cyano-5-pyrimidyl |
| 231 | H | H | H | H | H | 2-nitro-5-pyrimidyl |
| 232 | H | H | H | H | H | 4-nitro-5-pyrimidyl |
| 233 | H | H | H | H | H | 2-methanesulfonyl-5-pyrimidyl |
| 234 | H | H | H | H | H | 4-methanesulfonyl-5-pyrimidyl |
| 235 | H | H | H | H | H | 2-pyrazinyl |
| 236 | H | H | H | H | H | 3-fluoro-2-pyrazinyl |
| 237 | H | H | H | H | H | 5-fluoro-2-pyrazinyl |
| 238 | H | H | H | H | H | 6-fluoro-2-pyrazinyl |
| 239 | H | H | H | H | H | 3-chloro-2-pyrazinyl |
| 240 | H | H | H | H | H | 5-chloro-2-pyrazinyl |
| 241 | H | H | H | H | H | 6-chloro-2-pyrazinyl |
| 242 | H | H | H | H | H | 3-bromo-2-pyrazinyl |
| 243 | H | H | H | H | H | 5-bromo-2-pyrazinyl |
| 244 | H | H | H | H | H | 6-bromo-2-pyrazinyl |
| 245 | H | H | H | H | H | 3-methoxy-2-pyrazinyl |
| 246 | H | H | H | H | H | 5-methoxy-2-pyrazinyl |
| 247 | H | H | H | H | H | 6-methoxy-2-pyrazinyl |
| 248 | H | H | H | H | H | 3-trifluoromethoxy-2-pyrazinyl |
| 249 | H | H | H | H | H | 5-trifluoromethoxy-2-pyrazinyl |
| 250 | H | H | H | H | H | 6-trifluoromethoxy-2-pyrazinyl |
| 251 | H | H | H | H | H | 3-methyl-2-pyrazinyl |
| 252 | H | H | H | H | H | 5-methyl-2-pyrazinyl |
| 253 | H | H | H | H | H | 6-methyl-2-pyrazinyl |
| 254 | H | H | H | H | H | 3-trifluoromethyl-2-pyrazinyl |
| 255 | H | H | H | H | H | 5-trifluoromethyl-2-pyrazinyl |
| 256 | H | H | H | H | H | 6-trifluoromethyl-2-pyrazinyl |
| 257 | H | H | H | H | H | 3-cyano-2-pyrazinyl |
| 258 | H | H | H | H | H | 5-cyano-2-pyrazinyl |
| 259 | H | H | H | H | H | 6-cyano-2-pyrazinyl |
| 260 | H | H | H | H | H | 3-nitro-2-pyrazinyl |
| 261 | H | H | H | H | H | 5-nitro-2-pyrazinyl |
| 262 | H | H | H | H | H | 6-nitro-2-pyrazinyl |
| 263 | H | H | H | H | H | 3-methylsulfonat-2-pyrazinyl |
| 264 | H | H | H | H | H | 5-methylsulfonate-2-pyrazinyl |
| 265 | H | H | H | H | H | 6-methylsulfonate-2-pyrazinyl |
| 266 | H | H | H | H | H | 2-furanyl |
| 267 | H | H | H | H | H | 3-fluoro-2-furanyl |
| 268 | H | H | H | H | H | 4-fluoro-2-furanyl |
| 269 | H | H | H | H | H | 5-fluoro-2-furanyl |
| 270 | H | H | H | H | H | 3-chloro-2-furanyl |
| 271 | H | H | H | H | H | 4-chloro-2-furanyl |
| 272 | H | H | H | H | H | 5-chloro-2-furanyl |
| 273 | H | H | H | H | H | 3-bromo-2-furanyl |
| 274 | H | H | H | H | H | 4-bromo-2-furanyl |
| 275 | H | H | H | H | H | 5-bromo-2-furanyl |
| 276 | H | H | H | H | H | 3-methoxy-2-furanyl |
| 277 | H | H | H | H | H | 4-methoxy-2-furanyl |
| 278 | H | H | H | H | H | 5-methoxy-2-furanyl |
| 279 | H | H | H | H | H | 3-trifluoromethoxy-2-furanyl |
| 280 | H | H | H | H | H | 4-trifluoromethoxy-2-furanyl |
| 281 | H | H | H | H | H | 5-trifluoromethoxy-2-furanyl |
| 282 | H | H | H | H | H | 3-methyl-2-furanyl |
| 283 | H | H | H | H | H | 4-methyl-2-furanyl |
| 284 | H | H | H | H | H | 5-methyl-2-furanyl |
| 285 | H | H | H | H | H | 3-trifluoromethyl-2-furanyl |
| 286 | H | H | H | H | H | 4-trifluoromethyl-2-furanyl |
| 287 | H | H | H | H | H | 5-trifluoromethyl-2-furanyl |
| 288 | H | H | H | H | H | 3-cyano-2-furanyl |
| 289 | H | H | H | H | H | 4-cyano-2-furanyl |
| 290 | H | H | H | H | H | 5-cyano-2-furanyl |
| 291 | H | H | H | H | H | 3-nitro-2-furanyl |
| 292 | H | H | H | H | H | 4-nitro-2-furanyl |
| 293 | H | H | H | H | H | 5-nitro-2-furanyl |
| 294 | H | H | H | H | H | 3-methanesulfonyl-2-furanyl |
| 295 | H | H | H | H | H | 4-methanesulfonyl-2-furanyl |
| 296 | H | H | H | H | H | 5-methanesufonyl-2-furanyl |
| 297 | H | H | H | H | H | 3-furanyl |
| 298 | H | H | H | H | H | 3-fluoro-2-furanyl |
| 299 | H | H | H | H | H | 4-fluoro-2-furanyl |
| 300 | H | H | H | H | H | 5-fluoro-2-furanyl |
| 301 | H | H | H | H | H | 3-chloro-2-furanyl |
| 302 | H | H | H | H | H | 4-chloro-2-furanyl |
| 303 | H | H | H | H | H | 5-chloro-2-furanyl |
| 304 | H | H | H | H | H | 3-bromo-2-furanyl |

| Compound number | R⁵ | R⁶ | R⁷ | R⁸ | R⁹ | HetAr |
|---|---|---|---|---|---|---|
| 305 | H | H | H | H | H | 4-bromo-2-furanyl |
| 306 | H | H | H | H | H | 5-bromo-2-furanyl |
| 307 | H | H | H | H | H | 3-methoxy-2-furanyl |
| 308 | H | H | H | H | H | 4-methoxy-2-furanyl |
| 309 | H | H | H | H | H | 5-methoxy-2-furanyl |
| 310 | H | H | H | H | H | 3-trifluoromethoxy-2-furanyl |
| 311 | H | H | H | H | H | 4-trifluoromethoxy-2-furanyl |
| 312 | H | H | H | H | H | 5-trifluoromethoxy-2-furanyl |
| 313 | H | H | H | H | H | 3-methyl-2-furanyl |
| 314 | H | H | H | H | H | 4-methyl-2-furanyl |
| 315 | H | H | H | H | H | 5-methyl-2-furanyl |
| 316 | H | H | H | H | H | 3-trifluoromethyl-2-furanyl |
| 317 | H | H | H | H | H | 4-trifluoromethyl-2-furanyl |
| 318 | H | H | H | H | H | 5-trifluoromethyl-2-furanyl |
| 319 | H | H | H | H | H | 3-cyano-2-furanyl |
| 320 | H | H | H | H | H | 4-cyano-2-furanyl |
| 321 | H | H | H | H | H | 5-cyano-2-furanyl |
| 322 | H | H | H | H | H | 3-nitro-2-furanyl |
| 323 | H | H | H | H | H | 4-nitro-2-furanyl |
| 324 | H | H | H | H | H | 5-nitro-2-furanyl |
| 325 | H | H | H | H | H | 3-methanesulfonyl-2-furanyl |
| 326 | H | H | H | H | H | 4-methanesulfonyl-2-furanyl |
| 327 | H | H | H | H | H | 5-methanesufonyl-2-furanyl |
| 328 | H | H | H | H | H | 3-furanyl |
| 329 | H | H | H | H | H | 2-fluoro-3-furanyl |
| 330 | H | H | H | H | H | 4-fluoro-3-furanyl |
| 331 | H | H | H | H | H | 5-fluoro-3-furanyl |
| 332 | H | H | H | H | H | 2-chloro-3-furanyl |
| 333 | H | H | H | H | H | 4-chloro-3-furanyl |
| 334 | H | H | H | H | H | 5-chloro-3-furanyl |
| 335 | H | H | H | H | H | 2-bromo-3-furanyl |
| 336 | H | H | H | H | H | 4-bromo-3-furanyl |
| 337 | H | H | H | H | H | 5-bromo-3-furanyl |
| 338 | H | H | H | H | H | 2-methoxy-3-furanyl |
| 339 | H | H | H | H | H | 4-methoxy-3-furanyl |
| 340 | H | H | H | H | H | 5-methoxy-3-furanyl |
| 341 | H | H | H | H | H | 2-trifluoromethoxy-3-furanyl |
| 342 | H | H | H | H | H | 4-trifluoromethoxy-3-furanyl |
| 343 | H | H | H | H | H | 5-trifluoromethoxy-3-furanyl |
| 344 | H | H | H | H | H | 2-methyl-3-furanyl |
| 345 | H | H | H | H | H | 4-methyl-3-furanyl |
| 346 | H | H | H | H | H | 5-methyl-3-furanyl |
| 347 | H | H | H | H | H | 2-trifluoromethyl-3-furanyl |
| 348 | H | H | H | H | H | 4-trifluoromethyl-3-furanyl |
| 349 | H | H | H | H | H | 5-trifluoromethyl-3-furanyl |
| 350 | H | H | H | H | H | 2-cyano-3-furanyl |
| 351 | H | H | H | H | H | 4-cyano-3-furanyl |
| 352 | H | H | H | H | H | 5-cyano-3-furanyl |
| 353 | H | H | H | H | H | 2-nitro-3-furanyl |
| 354 | H | H | H | H | H | 4-nitro-3-furanyl |
| 355 | H | H | H | H | H | 5-nitro-3-furanyl |
| 356 | H | H | H | H | H | 2-methanesulfonyl-3-furanyl |
| 357 | H | H | H | H | H | 4-methanesulfonyl-3-furanyl |
| 358 | H | H | H | H | H | 5-methanesufonyl-3-furanyl |
| 359 | H | H | H | H | H | 2-thiophenyl |
| 360 | H | H | H | H | H | 3-fluoro-2-thiophenyl |
| 361 | H | H | H | H | H | 4-fluoro-2-thiophenyl |
| 362 | H | H | H | H | H | 5-fluoro-2-thiophenyl |
| 363 | H | H | H | H | H | 3-chloro-2-thiophenyl |
| 364 | H | H | H | H | H | 4-chloro-2-thiophenyl |
| 365 | H | H | H | H | H | 5-chloro-2-thiophenyl |
| 366 | H | H | H | H | H | 3-bromo-2-thiophenyl |
| 367 | H | H | H | H | H | 4-bromo-2-thiophenyl |
| 368 | H | H | H | H | H | 5-bromo-2-thiophenyl |
| 369 | H | H | H | H | H | 3-methoxy-2-thiophenyl |
| 370 | H | H | H | H | H | 4-methoxy-2-thiophenyl |
| 371 | H | H | H | H | H | 5-methoxy-2-thiophenyl |
| 372 | H | H | H | H | H | 3-trifluoromethoxy-2-thiophenyl |
| 373 | H | H | H | H | H | 4-trifluoromethoxy-2-thiophenyl |
| 374 | H | H | H | H | H | 5-trifluoromethoxy-2-thiophenyl |
| 375 | H | H | H | H | H | 3-methyl-2-thiophenyl |
| 376 | H | H | H | H | H | 4-methyl-2-thiophenyl |
| 377 | H | H | H | H | H | 5-methyl-2-thiophenyl |
| 378 | H | H | H | H | H | 3-trifluoromethyl-2-thiophenyl |
| 379 | H | H | H | H | H | 4-trifluoromethyl-2-thiophenyl |
| 380 | H | H | H | H | H | 5-trifluoromethyl-2-thiophenyl |
| 381 | H | H | H | H | H | 3-cyano-2-thiophenyl |
| 382 | H | H | H | H | H | 4-cyano-2-thiophenyl |
| 383 | H | H | H | H | H | 5-cyano-2-thiophenyl |
| 384 | H | H | H | H | H | 3-nitro-2-thiophenyl |
| 385 | H | H | H | H | H | 4-nitro-2-thiophenyl |
| 386 | H | H | H | H | H | 5-nitro-2-thiophenyl |
| 387 | H | H | H | H | H | 3-methanesulfonyl-2-thiophenyl |
| 388 | H | H | H | H | H | 4-methanesulfonyl-2-thiophenyl |
| 389 | H | H | H | H | H | 5-methanesufonyl-2-thiophenyl |
| 390 | H | H | H | H | H | 3-thiophenyl |
| 391 | H | H | H | H | H | 3-fluoro-2-thiophenyl |
| 392 | H | H | H | H | H | 4-fluoro-2-thiophenyl |
| 393 | H | H | H | H | H | 5-fluoro-2-thiophenyl |
| 394 | H | H | H | H | H | 3-chloro-2-thiophenyl |
| 395 | H | H | H | H | H | 4-chloro-2-thiophenyl |
| 396 | H | H | H | H | H | 5-chloro-2-thiophenyl |
| 397 | H | H | H | H | H | 3-bromo-2-thiophenyl |
| 398 | H | H | H | H | H | 4-bromo-2-thiophenyl |
| 399 | H | H | H | H | H | 5-bromo-2-thiophenyl |
| 400 | H | H | H | H | H | 3-methoxy-2-thiophenyl |
| 401 | H | H | H | H | H | 4-methoxy-2-thiophenyl |
| 402 | H | H | H | H | H | 5-methoxy-2-thiophenyl |
| 403 | H | H | H | H | H | 3-trifluoromethoxy-2-thiophenyl |
| 404 | H | H | H | H | H | 4-trifluoromethoxy-2-thiophenyl |
| 405 | H | H | H | H | H | 5-trifluoromethoxy-2-thiophenyl |
| 406 | H | H | H | H | H | 3-methyl-2-thiophenyl |
| 407 | H | H | H | H | H | 4-methyl-2-thiophenyl |
| 408 | H | H | H | H | H | 5-methyl-2-thiophenyl |
| 409 | H | H | H | H | H | 3-trifluoromethyl-2-thiophenyl |
| 410 | H | H | H | H | H | 4-trifluoromethyl-2-thiophenyl |
| 411 | H | H | H | H | H | 5-trifluoromethyl-2-thiophenyl |
| 412 | H | H | H | H | H | 3-cyano-2-thiophenyl |
| 413 | H | H | H | H | H | 4-cyano-2-thiophenyl |
| 414 | H | H | H | H | H | 5-cyano-2-thiophenyl |
| 415 | H | H | H | H | H | 3-nitro-2-thiophenyl |
| 416 | H | H | H | H | H | 4-nitro-2-thiophenyl |
| 417 | H | H | H | H | H | 5-nitro-2-thiophenyl |
| 418 | H | H | H | H | H | 3-methanesulfonyl-2-thiophenyl |
| 419 | H | H | H | H | H | 4-methanesulfonyl-2-thiophenyl |
| 420 | H | H | H | H | H | 5-methanesufonyl-2-thiophenyl |

| Compound number | R⁵ | R⁶ | R⁷ | R⁸ | R⁹ | HetAr |
|---|---|---|---|---|---|---|
| 421 | H | H | H | H | H | 3-thiophenyl |
| 422 | H | H | H | H | H | 2-fluoro-3-thiophenyl |
| 423 | H | H | H | H | H | 4-fluoro-3-thiophenyl |
| 424 | H | H | H | H | H | 5-fluoro-3-thiophenyl |
| 425 | H | H | H | H | H | 2-chloro-3-thiophenyl |
| 426 | H | H | H | H | H | 4-chloro-3-thiophenyl |
| 427 | H | H | H | H | H | 5-chloro-3-thiophenyl |
| 428 | H | H | H | H | H | 2-bromo-3-thiophenyl |
| 429 | H | H | H | H | H | 4-bromo-3-thiophenyl |
| 430 | H | H | H | H | H | 5-bromo-3-thiophenyl |
| 431 | H | H | H | H | H | 2-methoxy-3-thiophenyl |
| 432 | H | H | H | H | H | 4-methoxy-3-thiophenyl |
| 433 | H | H | H | H | H | 5-methoxy-3-thiophenyl |
| 434 | H | H | H | H | H | 2-trifluoromethoxy-3-thiophenyl |
| 435 | H | H | H | H | H | 4-trifluoromethoxy-3-thiophenyl |
| 436 | H | H | H | H | H | 5-trifluoromethoxy-3-thiophenyl |
| 437 | H | H | H | H | H | 2-methyl-3-thiophenyl |
| 438 | H | H | H | H | H | 4-methyl-3-thiophenyl |
| 439 | H | H | H | H | H | 5-methyl-3-thiophenyl |
| 440 | H | H | H | H | H | 2-trifluoromethyl-3-thiophenyl |
| 441 | H | H | H | H | H | 4-trifluoromethyl-3-thiophenyl |
| 442 | H | H | H | H | H | 5-trifluoromethyl-3-thiophenyl |
| 443 | H | H | H | H | H | 2-cyano-3-thiophenyl |
| 444 | H | H | H | H | H | 4-cyano-3-thiophenyl |
| 445 | H | H | H | H | H | 5-cyano-3-thiophenyl |
| 446 | H | H | H | H | H | 2-nitro-3-thiophenyl |
| 447 | H | H | H | H | H | 4-nitro-3-thiophenyl |
| 448 | H | H | H | H | H | 5-nitro-3-thiophenyl |
| 449 | H | H | H | H | H | 2-methanesulfonyl-3-thiophenyl |
| 450 | H | H | H | H | H | 4-methanesulfonyl-3-thiophenyl |
| 451 | H | H | H | H | H | 5-methanesufonyl-3-thiophenyl |
| 452 | H | H | H | H | H | 2-oxazole |
| 453 | H | H | H | H | H | 4-fluoro-2-oxazole |
| 454 | H | H | H | H | H | 5-fluoro-2-oxazole |
| 455 | H | H | H | H | H | 4-chloro-2-oxazole |
| 456 | H | H | H | H | H | 5-chloro-2-oxazole |
| 457 | H | H | H | H | H | 4-bromo-2-oxazole |
| 458 | H | H | H | H | H | 5-bromo-2-oxazole |
| 459 | H | H | H | H | H | 4-methoxy-2-oxazole |
| 460 | H | H | H | H | H | 5-methoxy-2-oxazole |
| 461 | H | H | H | H | H | 4-trifluoromethoxy-2-oxazole |
| 462 | H | H | H | H | H | 5-trifluoromethoxy-2-oxazole |
| 463 | H | H | H | H | H | 4-methyl-2-oxazole |
| 464 | H | H | H | H | H | 5-methyl-2-oxazole |
| 465 | H | H | H | H | H | 4-trifluoromethyl-2-oxazole |
| 466 | H | H | H | H | H | 5-trifluoromethyl-2-oxazole |
| 467 | H | H | H | H | H | 4-cyano-2-oxazole |
| 468 | H | H | H | H | H | 5-cyano-2-oxazole |
| 469 | H | H | H | H | H | 4-nitro-2-oxazole |
| 470 | H | H | H | H | H | 5-nitro-2-oxazole |
| 471 | H | H | H | H | H | 4-methanesulfonyl-2-oxazole |
| 472 | H | H | H | H | H | 5-methanesulfonyl-2-oxazole |
| 473 | H | H | H | H | H | 4-oxazole |
| 474 | H | H | H | H | H | 2-fluoro-4-oxazole |
| 475 | H | H | H | H | H | 5-fluoro-4-oxazole |
| 476 | H | H | H | H | H | 2-chloro-4-oxazole |
| 477 | H | H | H | H | H | 5-chloro-4-oxazole |
| 478 | H | H | H | H | H | 2-bromo-4-oxazole |
| 479 | H | H | H | H | H | 5-bromo-4-oxazole |
| 480 | H | H | H | H | H | 2-methoxy-4-oxazole |
| 481 | H | H | H | H | H | 5-methoxy-4-oxazole |
| 482 | H | H | H | H | H | 2-trifluoromethoxy-4-oxazole |
| 483 | H | H | H | H | H | 5-trifluoromethoxy-4-oxazole |
| 484 | H | H | H | H | H | 2-methyl-4-oxazole |
| 485 | H | H | H | H | H | 5-methyl-4-oxazole |
| 486 | H | H | H | H | H | 4-trifluoromethyl-4-oxazole |
| 487 | H | H | H | H | H | 5-trifluoromethyl-4-oxazole |
| 488 | H | H | H | H | H | 4-cyano-4-oxazole |
| 489 | H | H | H | H | H | 5-cyano-4-oxazole |
| 490 | H | H | H | H | H | 4-nitro-4-oxazole |
| 491 | H | H | H | H | H | 5-nitro-4-oxazole |
| 492 | H | H | H | H | H | 4-methanesulfonyl-4-oxazole |
| 493 | H | H | H | H | H | 5-methanesulfonyl-4-oxazole |
| 494 | H | H | H | H | H | 5-oxazole |
| 495 | H | H | H | H | H | 2-fluoro-5-oxazole |
| 496 | H | H | H | H | H | 4-fluoro-5-oxazole |
| 497 | H | H | H | H | H | 2-chloro-5-oxazole |
| 498 | H | H | H | H | H | 4-chloro-5-oxazole |
| 499 | H | H | H | H | H | 2-bromo-5-oxazole |
| 500 | H | H | H | H | H | 4-bromo-5-oxazole |
| 501 | H | H | H | H | H | 2-methoxy-5-oxazole |
| 502 | H | H | H | H | H | 4-methoxy-5-oxazole |
| 503 | H | H | H | H | H | 2-trifluoromethoxy-5-oxazole |
| 504 | H | H | H | H | H | 4-trifluoromethoxy-5-oxazole |
| 505 | H | H | H | H | H | 2-methyl-5-oxazole |
| 506 | H | H | H | H | H | 4-methyl-5-oxazole |
| 507 | H | H | H | H | H | 2-trifluoromethyl-5-oxazole |
| 508 | H | H | H | H | H | 4-trifluoromethyl-5-oxazole |
| 509 | H | H | H | H | H | 2-cyano-5-oxazole |
| 510 | H | H | H | H | H | 4-cyano-5-oxazole |
| 511 | H | H | H | H | H | 2-nitro-5-oxazole |
| 512 | H | H | H | H | H | 4-nitro-5-oxazole |
| 513 | H | H | H | H | H | 2-methanesulfonyl-5-oxazole |
| 514 | H | H | H | H | H | 4-methanesulfonyl-5-oxazole |
| 515 | H | H | H | H | H | 2-thiazole |
| 516 | H | H | H | H | H | 4-fluoro-2-thiazole |
| 517 | H | H | H | H | H | 5-fluoro-2-thiazole |
| 518 | H | H | H | H | H | 4-chloro-2-thiazole |
| 519 | H | H | H | H | H | 5-chloro-2-thiazole |
| 520 | H | H | H | H | H | 4-bromo-2-thiazole |
| 521 | H | H | H | H | H | 5-bromo-2-thiazole |
| 522 | H | H | H | H | H | 4-methoxy-2-thiazole |
| 523 | H | H | H | H | H | 5-methoxy-2-thiazole |
| 524 | H | H | H | H | H | 4-trifluoromethoxy-2-thiazole |
| 525 | H | H | H | H | H | 5-trifluoromethoxy-2-thiazole |
| 526 | H | H | H | H | H | 4-methyl-2-thiazole |
| 527 | H | H | H | H | H | 5-methyl-2-thiazole |
| 528 | H | H | H | H | H | 4-trifluoromethyl-2-thiazole |
| 529 | H | H | H | H | H | 5-trifluoromethyl-2-thiazole |
| 530 | H | H | H | H | H | 4-cyano-2-thiazole |
| 531 | H | H | H | H | H | 5-cyano-2-thiazole |
| 532 | H | H | H | H | H | 4-nitro-2-thiazole |
| 533 | H | H | H | H | H | 5-nitro-2-thiazole |
| 534 | H | H | H | H | H | 4-methanesulfonyl-2-thiazole |
| 535 | H | H | H | H | H | 5-methanesulfonyl-2-thiazole |
| 536 | H | H | H | H | H | 4-thiazole |
| 537 | H | H | H | H | H | 2-fluoro-4-thiazole |
| 538 | H | H | H | H | H | 5-fluoro-4-thiazole |
| 539 | H | H | H | H | H | 2-chloro-4-thiazole |

| Compound number | R⁵ | R⁶ | R⁷ | R⁸ | R⁹ | HetAr |
|---|---|---|---|---|---|---|
| 540 | H | H | H | H | H | 5-chloro-4-thiazole |
| 541 | H | H | H | H | H | 2-bromo-4-thiazole |
| 542 | H | H | H | H | H | 5-bromo-4-thiazole |
| 543 | H | H | H | H | H | 2-methoxy-4-thiazole |
| 544 | H | H | H | H | H | 5-methoxy-4-thiazole |
| 545 | H | H | H | H | H | 2-trifluoromethoxy-4-thiazole |
| 546 | H | H | H | H | H | 5-trifluoromethoxy-4-thiazole |
| 547 | H | H | H | H | H | 2-methyl-4-thiazole |
| 548 | H | H | H | H | H | 5-methyl-4-thiazole |
| 549 | H | H | H | H | H | 4-trifluoromethyl-4-thiazole |
| 550 | H | H | H | H | H | 5-trifluoromethyl-4-thiazole |
| 551 | H | H | H | H | H | 4-cyano-4-thiazole |
| 552 | H | H | H | H | H | 5-cyano-4-thiazole |
| 553 | H | H | H | H | H | 4-nitro-4-thiazole |
| 554 | H | H | H | H | H | 5-nitro-4-thiazole |
| 555 | H | H | H | H | H | 4-methanesulfonyl-4-thiazole |
| 556 | H | H | H | H | H | 5-methanesulfonyl-4-thiazole |
| 557 | H | H | H | H | H | 5-thiazole |
| 558 | H | H | H | H | H | 2-fluoro-5-thiazole |
| 559 | H | H | H | H | H | 4-fluoro-5-thiazole |
| 560 | H | H | H | H | H | 2-chloro-5-thiazole |
| 561 | H | H | H | H | H | 4-chloro-5-thiazole |
| 562 | H | H | H | H | H | 2-bromo-5-thiazole |
| 563 | H | H | H | H | H | 4-bromo-5-thiazole |
| 564 | H | H | H | H | H | 2-methoxy-5-thiazole |
| 565 | H | H | H | H | H | 4-methoxy-5-thiazole |
| 566 | H | H | H | H | H | 2-trifluoromethoxy-5-thiazole |
| 567 | H | H | H | H | H | 4-trifluoromethoxy-5-thiazole |
| 568 | H | H | H | H | H | 2-methyl-5-thiazole |
| 569 | H | H | H | H | H | 4-methyl-5-thiazole |
| 570 | H | H | H | H | H | 2-trifluoromethyl-5-thiazole |
| 571 | H | H | H | H | H | 4-trifluoromethyl-5-thiazole |
| 572 | H | H | H | H | H | 2-cyano-5-thiazole |
| 573 | H | H | H | H | H | 4-cyano-5-thiazole |
| 574 | H | H | H | H | H | 2-nitro-5-thiazole |
| 575 | H | H | H | H | H | 4-nitro-5-thiazole |
| 576 | H | H | H | H | H | 2-methanesulfonyl-5-thiazole |
| 577 | H | CH₃ | H | H | H | 4-methanesulfonyl-5-thiazole |
| 578 | H | CH₃ | H | H | H | 2-pyridyl |
| 579 | H | CH₃ | H | H | H | 3-fluoro-2-pyridyl |
| 580 | H | CH₃ | H | H | H | 4-fluoro-2-pyridyl |
| 581 | H | CH₃ | H | H | H | 5-fluoro-2-pyridyl |
| 582 | H | CH₃ | H | H | H | 6-fluoro-2-pyridyl |
| 583 | H | CH₃ | H | H | H | 3-chloro-2-pyridyl |
| 584 | H | CH₃ | H | H | H | 4-chloro-2-pyridyl |
| 585 | H | CH₃ | H | H | H | 5-chloro-2-pyridyl |
| 586 | H | CH₃ | H | H | H | 6-chloro-2-pyridyl |
| 587 | H | CH₃ | H | H | H | 3-methyl-2-pyridyl |
| 588 | H | CH₃ | H | H | H | 4-methyl-2-pyridyl |
| 589 | H | CH₃ | H | H | H | 5-methyl-2-pyridyl |
| 590 | H | CH₃ | H | H | H | 6-methyl-2-pyridyl |
| 591 | H | CH₃ | H | H | H | 3-trifluoromethyl-2-pyridyl |
| 592 | H | CH₃ | H | H | H | 4-trifluoromethyl-2-pyridyl |
| 593 | H | CH₃ | H | H | H | 5-trifluoromethyl-2-pyridyl |
| 594 | H | CH₃ | H | H | H | 6-trifluoromethyl-2-pyridyl |
| 595 | H | CH₃ | H | H | H | 3-methoxy-2-pyridyl |
| 596 | H | CH₃ | H | H | H | 4-methoxy-2-pyridyl |
| 597 | H | CH₃ | H | H | H | 5-methoxy-2-pyridyl |
| 598 | H | CH₃ | H | H | H | 6-methoxy-2-pyridyl |
| 599 | H | CH₃ | H | H | H | 3-trifluoromethoxy-2-pyridyl |
| 600 | H | CH₃ | H | H | H | 4-trifluoromethoxy-2-pyridyl |
| 601 | H | CH₃ | H | H | H | 5-trifluoromethoxy-2-pyridyl |
| 602 | H | CH₃ | H | H | H | 6-trifluoromethoxy-2-pyridyl |
| 603 | H | CH₃ | H | H | H | 3-cyano-2-pyridyl |
| 604 | H | CH₃ | H | H | H | 4-cyano-2-pyridyl |
| 605 | H | CH₃ | H | H | H | 5-cyano-2-pyridyl |
| 606 | H | CH₃ | H | H | H | 6-cyano-2-pyridyl |
| 607 | H | CH₃ | H | H | H | 3-nitro-2-pyridyl |
| 608 | H | CH₃ | H | H | H | 4-nitro-2-pyridyl |
| 609 | H | CH₃ | H | H | H | 5-nitro-2-pyridyl |
| 610 | H | CH₃ | H | H | H | 6-nitro-2-pyridyl |
| 611 | H | CH₃ | H | H | H | 3-methanesulfonyl-2-pyridyl |
| 612 | H | CH₃ | H | H | H | 4-methanesulfonyl-2-pyridyl |
| 613 | H | CH₃ | H | H | H | 5-methanesulfonyl-2-pyridyl |
| 614 | H | CH₃ | H | H | H | 6-methanesulfonyl-2-pyridyl |
| 615 | H | CH₃ | H | H | H | 3-pyridyl |
| 616 | H | CH₃ | H | H | H | 2-fluoro-3-pyridyl |
| 617 | H | CH₃ | H | H | H | 4-fluoro-3-pyridyl |
| 618 | H | CH₃ | H | H | H | 5-fluoro-3-pyridyl |
| 619 | H | CH₃ | H | H | H | 6-fluoro-3-pyridyl |
| 620 | H | CH₃ | H | H | H | 2-chloro-3-pyridyl |
| 621 | H | CH₃ | H | H | H | 4-chloro-3-pyridyl |
| 622 | H | CH₃ | H | H | H | 5-chloro-3-pyridyl |
| 623 | H | CH₃ | H | H | H | 6-chloro-3-pyridyl |
| 624 | H | CH₃ | H | H | H | 2-bromo-3-pyridyl |
| 625 | H | CH₃ | H | H | H | 4-bromo-3-pyridyl |
| 626 | H | CH₃ | H | H | H | 5-bromo-3-pyridyl |
| 627 | H | CH₃ | H | H | H | 6-bromo-3-pyridyl |
| 628 | H | CH₃ | H | H | H | 2-methoxy-3-pyridyl |
| 629 | H | CH₃ | H | H | H | 4-methoxy-3-pyridyl |
| 630 | H | CH₃ | H | H | H | 5-methoxy-3-pyridyl |
| 631 | H | CH₃ | H | H | H | 6-methoxy-3-pyridyl |
| 632 | H | CH₃ | H | H | H | 2-trifluoromethoxy-3-pyridyl |
| 633 | H | CH₃ | H | H | H | 4-trifluoromethoxy-3-pyridyl |
| 634 | H | CH₃ | H | H | H | 5-trifluoromethoxy-3-pyridyl |
| 635 | H | CH₃ | H | H | H | 6-trifluoromethoxy-3-pyridyl |
| 636 | H | CH₃ | H | H | H | 2-methyl-3-pyridyl |
| 637 | H | CH₃ | H | H | H | 4-methyl-3-pyridyl |
| 638 | H | CH₃ | H | H | H | 5-methyl-3-pyridyl |
| 639 | H | CH₃ | H | H | H | 6-methyl-3-pyridyl |
| 640 | H | CH₃ | H | H | H | 2-trifluoromethyl-3-pyridyl |
| 641 | H | CH₃ | H | H | H | 4-trifluoromethyl-3-pyridyl |
| 642 | H | CH₃ | H | H | H | 5-trifluoromethyl-3-pyridyl |
| 643 | H | CH₃ | H | H | H | 6-trifluoromethyl-3-pyridyl |
| 644 | H | CH₃ | H | H | H | 2-cyano-3-pyridyl |
| 645 | H | CH₃ | H | H | H | 4-cyano-3-pyridyl |
| 646 | H | CH₃ | H | H | H | 5-cyano-3-pyridyl |
| 647 | H | CH₃ | H | H | H | 6-cyano-3-pyridyl |
| 648 | H | CH₃ | H | H | H | 2-nitro-3-pyridyl |
| 649 | H | CH₃ | H | H | H | 4-nitro-3-pyridyl |
| 650 | H | CH₃ | H | H | H | 5-nitro-3-pyridyl |
| 651 | H | CH₃ | H | H | H | 6-nitro-3-pyridyl |
| 652 | H | CH₃ | H | H | H | 2-methanesulfonyl-3-pyridyl |
| 652 | H | CH₃ | H | H | H | 4-methanesulfonyl-3-pyridyl |
| 654 | H | CH₃ | H | H | H | 5-methanesulfonyl-3-pyridyl |
| 655 | H | CH₃ | H | H | H | 6-methanesulfonyl-3-pyridyl |
| 656 | H | CH₃ | H | H | H | 4-pyridyl |
| 657 | H | CH₃ | H | H | H | 2-fluoro-4-pyridyl |
| 658 | H | CH₃ | H | H | H | 3-fluoro-4-pyridyl |
| 659 | H | CH₃ | H | H | H | 2-chloro-4-pyridyl |

| Compound number | R⁵ | R⁶ | R⁷ | R⁸ | R⁹ | HetAr |
|---|---|---|---|---|---|---|
| 660 | H | CH₃ | H | H | H | 3-chloro-4-pyridyl |
| 661 | H | CH₃ | H | H | H | 2-bromo-4-pyridyl |
| 662 | H | CH₃ | H | H | H | 3-bromo-4-pyridyl |
| 663 | H | CH₃ | H | H | H | 2-methoxy-4-pyridyl |
| 664 | H | CH₃ | H | H | H | 3-methoxy-4-pyridyl |
| 665 | H | CH₃ | H | H | H | 2-trifluoromethoxy-4-pyridyl |
| 666 | H | CH₃ | H | H | H | 3-trifluoromethoxy-4-pyridyl |
| 667 | H | CH₃ | H | H | H | 2-methyl-4-pyridyl |
| 668 | H | CH₃ | H | H | H | 3-methyl-4-pyridyl |
| 669 | H | CH₃ | H | H | H | 2-trifluoromethyl-4-pyridyl |
| 670 | H | CH₃ | H | H | H | 3-trifluoromethyl-4-pyridyl |
| 671 | H | CH₃ | H | H | H | 2-cyano-4-pyridyl |
| 672 | H | CH₃ | H | H | H | 3-cyano-4-pyridyl |
| 673 | H | CH₃ | H | H | H | 2-nitro-4-pyridyl |
| 674 | H | CH₃ | H | H | H | 3-nitro-4-pyridyl |
| 675 | H | CH₃ | H | H | H | 2-methanesulfonyl-4-pyridyl |
| 676 | H | CH₃ | H | H | H | 3-methanesulfonyl-4-pyridyl |
| 677 | H | CH₃ | H | H | H | 2-pyridazinyl |
| 678 | H | CH₃ | H | H | H | 4-fluoro-2-pyridazinyl |
| 679 | H | CH₃ | H | H | H | 5-fluoro-2-pyridazinyl |
| 680 | H | CH₃ | H | H | H | 6-fluoro-2-pyridazinyl |
| 681 | H | CH₃ | H | H | H | 4-chloro-2-pyridazinyl |
| 682 | H | CH₃ | H | H | H | 5-chloro-2-pyridazinyl |
| 683 | H | CH₃ | H | H | H | 6-chloro-2-pyridazinyl |
| 684 | H | CH₃ | H | H | H | 4-bromo-2-pyridazinyl |
| 685 | H | CH₃ | H | H | H | 5-bromo-2-pyridazinyl |
| 686 | H | CH₃ | H | H | H | 6-bromo-2-pyridazinyl |
| 687 | H | CH₃ | H | H | H | 4-methoxy-2-pyridazinyl |
| 688 | H | CH₃ | H | H | H | 5-methoxy-2-pyridazinyl |
| 689 | H | CH₃ | H | H | H | 6-methoxy-2-pyridazinyl |
| 690 | H | CH₃ | H | H | H | 4-trifluoromethoxy-2-pyridazinyl |
| 691 | H | CH₃ | H | H | H | 5-trifluoromethoxy-2-pyridazinyl |
| 692 | H | CH₃ | H | H | H | 6-trifluoromethoxy-2-pyridazinyl |
| 693 | H | CH₃ | H | H | H | 4-methyl-2-pyridazinyl |
| 694 | H | CH₃ | H | H | H | 5-methyl-2-pyridazinyl |
| 695 | H | CH₃ | H | H | H | 6-methyl-2-pyridazinyl |
| 696 | H | CH₃ | H | H | H | 4-trifluoromethyl-2-pyridazinyl |
| 697 | H | CH₃ | H | H | H | 5-trifluoromethyl-2-pyridazinyl |
| 698 | H | CH₃ | H | H | H | 6-trifluoromethyl-2-pyridazinyl |
| 699 | H | CH₃ | H | H | H | 4-cyano-2-pyridazinyl |
| 700 | H | CH₃ | H | H | H | 5-cyano-2-pyridazinyl |
| 701 | H | CH₃ | H | H | H | 6-cyano-2-pyridazinyl |
| 702 | H | CH₃ | H | H | H | 4-nitro-2-pyridazinyl |
| 703 | H | CH₃ | H | H | H | 5-nitro-2-pyridazinyl |
| 704 | H | CH₃ | H | H | H | 6-nitro-2-pyridazinyl |
| 705 | H | CH₃ | H | H | H | 4-methanesulfonyl-2-pyridazinyl |
| 706 | H | CH₃ | H | H | H | 5-methanesulfonyl-2-pyridazinyl |
| 707 | H | CH₃ | H | H | H | 6-methanesulfonyl-2-pyridazinyl |
| 708 | H | CH₃ | H | H | H | 3-pyridazinyl |
| 709 | H | CH₃ | H | H | H | 2-fluoro-3-pyridazinyl |
| 710 | H | CH₃ | H | H | H | 5-fluoro-3-pyridazinyl |
| 711 | H | CH₃ | H | H | H | 6-fluoro-3-pyridazinyl |
| 712 | H | CH₃ | H | H | H | 2-chloro-3-pyridazinyl |
| 713 | H | CH₃ | H | H | H | 5-chloro-3-pyridazinyl |
| 714 | H | CH₃ | H | H | H | 6-chloro-3-pyridazinyl |
| 715 | H | CH₃ | H | H | H | 2-bromo-3-pyridazinyl |
| 716 | H | CH₃ | H | H | H | 5-bromo-3-pyridazinyl |
| 717 | H | CH₃ | H | H | H | 6-bromo-3-pyridazinyl |
| 718 | H | CH₃ | H | H | H | 2-methoxy-3-pyridazinyl |
| 719 | H | CH₃ | H | H | H | 5-methoxy-3-pyridazinyl |
| 720 | H | CH₃ | H | H | H | 6-methoxy-3-pyridazinyl |
| 721 | H | CH₃ | H | H | H | 2-trifluoromethoxy-3-pyridazinyl |
| 722 | H | CH₃ | H | H | H | 5-trifluoromethoxy-3-pyridazinyl |
| 723 | H | CH₃ | H | H | H | 6-trifluoromethoxy-3-pyridazinyl |
| 724 | H | CH₃ | H | H | H | 2-methyl-3-pyridazinyl |
| 725 | H | CH₃ | H | H | H | 5-methyl-3-pyridazinyl |
| 726 | H | CH₃ | H | H | H | 6-methyl-3-pyridazinyl |
| 727 | H | CH₃ | H | H | H | 2-trifluoromethyl-3-pyridazinyl |
| 728 | H | CH₃ | H | H | H | 5-trifluoromethyl-3-pyridazinyl |
| 729 | H | CH₃ | H | H | H | 6-trifluoromethyl-3-pyridazinyl |
| 730 | H | CH₃ | H | H | H | 2-cyano-3-pyridazinyl |
| 731 | H | CH₃ | H | H | H | 5-cyano-3-pyridazinyl |
| 732 | H | CH₃ | H | H | H | 6-cyano-3-pyridazinyl |
| 733 | H | CH₃ | H | H | H | 2-nitro-3-pyridazinyl |
| 734 | H | CH₃ | H | H | H | 5-nitro-3-pyridazinyl |
| 735 | H | CH₃ | H | H | H | 6-nitro-3-pyridazinyl |
| 736 | H | CH₃ | H | H | H | 2-methanesulfonyl-3-pyridazinyl |
| 737 | H | CH₃ | H | H | H | 5-methanesulfonyl-3-pyridazinyl |
| 738 | H | CH₃ | H | H | H | 6-methanesulfonyl-3-pyridazinyl |
| 739 | H | CH₃ | H | H | H | 2-pyrimidyl |
| 740 | H | CH₃ | H | H | H | 4-fluoro-2-pyrimidyl |
| 741 | H | CH₃ | H | H | H | 5-fluoro-2-pyrimidyl |
| 742 | H | CH₃ | H | H | H | 4-chloro-2-pyrimidyl |
| 743 | H | CH₃ | H | H | H | 5-chloro-2-pyrimidyl |
| 744 | H | CH₃ | H | H | H | 4-bromo-2-pyrimidyl |
| 745 | H | CH₃ | H | H | H | 5-bromo-2-pyrimidyl |
| 746 | H | CH₃ | H | H | H | 4-methoxy-2-pyrimidyl |
| 747 | H | CH₃ | H | H | H | 5-methoxy-2-pyrimidyl |
| 748 | H | CH₃ | H | H | H | 4-trifluoromethoxy-2-pyrimidyl |
| 749 | H | CH₃ | H | H | H | 5-trifluoromethoxy-2-pyrimidyl |
| 750 | H | CH₃ | H | H | H | 4-methyl-2-pyrimidyl |
| 751 | H | CH₃ | H | H | H | 5-methyl-2-pyrimidyl |
| 752 | H | CH₃ | H | H | H | 4-trifluoromethyl-2-pyrimidyl |
| 753 | H | CH₃ | H | H | H | 5-trifluoromethyl-2-pyrimidyl |
| 754 | H | CH₃ | H | H | H | 4-cyano-2-pyrimidyl |
| 755 | H | CH₃ | H | H | H | 5-cyano-2-pyrimidyl |
| 756 | H | CH₃ | H | H | H | 4-nitro-2-pyrimidyl |
| 757 | H | CH₃ | H | H | H | 5-nitro-2-pyrimidyl |
| 758 | H | CH₃ | H | H | H | 4-methanesulfonyl-2-pyrimidyl |
| 759 | H | CH₃ | H | H | H | 5-methanesulfonyl-2-pyrimidyl |
| 760 | H | CH₃ | H | H | H | 4-pyrimidyl |
| 761 | H | CH₃ | H | H | H | 2-fluoro-4-pyrimidyl |
| 762 | H | CH₃ | H | H | H | 5-fluoro-4-pyrimidyl |
| 763 | H | CH₃ | H | H | H | 6-fluoro-4-pyrimidyl |
| 764 | H | CH₃ | H | H | H | 2-chloro-4-pyrimidyl |
| 765 | H | CH₃ | H | H | H | 5-chloro-4-pyrimidyl |
| 766 | H | CH₃ | H | H | H | 6-chloro-4-pyrimidyl |
| 767 | H | CH₃ | H | H | H | 2-bromo-4-pyrimidyl |
| 768 | H | CH₃ | H | H | H | 5-bromo-4-pyrimidyl |
| 769 | H | CH₃ | H | H | H | 6-bromo-4-pyrimidyl |
| 770 | H | CH₃ | H | H | H | 2-methoxy-4-pyrimidyl |
| 771 | H | CH₃ | H | H | H | 5-methoxy-4-pyrimidyl |
| 772 | H | CH₃ | H | H | H | 6-methoxy-4-pyrimidyl |
| 773 | H | CH₃ | H | H | H | 2-trifluoromethoxy-4-pyrimidyl |
| 774 | H | CH₃ | H | H | H | 5-trifluoromethoxy-4-pyrimidyl |
| 775 | H | CH₃ | H | H | H | 6-trifluoromethoxy-4-pyrimidyl |
| 776 | H | CH₃ | H | H | H | 2-methyl-4-pyrimidyl |
| 777 | H | CH₃ | H | H | H | 5-methyl-4-pyrimidyl |
| 778 | H | CH₃ | H | H | H | 6-methyl-4-pyrimidyl |
| 779 | H | CH₃ | H | H | H | 2-trifluoromethyl-4-pyrimidyl |

-continued

| Compound number | R⁵ | R⁶ | R⁷ | R⁸ | R⁹ | HetAr |
|---|---|---|---|---|---|---|
| 780 | H | CH₃ | H | H | H | 5-trifluoromethyl-4-pyrimidyl |
| 781 | H | CH₃ | H | H | H | 6-trifluoromethyl-4-pyrimidyl |
| 782 | H | CH₃ | H | H | H | 2-cyano-4-pyrimidyl |
| 783 | H | CH₃ | H | H | H | 5-cyano-4-pyrimidyl |
| 784 | H | CH₃ | H | H | H | 6-cyano-4-pyrimidyl |
| 785 | H | CH₃ | H | H | H | 2-nitro-4-pyrimidyl |
| 786 | H | CH₃ | H | H | H | 5-nitro-4-pyrimidyl |
| 787 | H | CH₃ | H | H | H | 6-nitro-4-pyrimidyl |
| 788 | H | CH₃ | H | H | H | 2-methanesulfonyl-4-pyrimidyl |
| 789 | H | CH₃ | H | H | H | 5-methanesulfonyl-4-pyrimidyl |
| 790 | H | CH₃ | H | H | H | 6-methanesulfonyl-4-pyrimidyl |
| 791 | H | CH₃ | H | H | H | 5-pyrimidyl |
| 792 | H | CH₃ | H | H | H | 2-fluoro-5-pyrimidyl |
| 793 | H | CH₃ | H | H | H | 4-fluoro-5-pyrimidyl |
| 794 | H | CH₃ | H | H | H | 2-chloro-5-pyrimidyl |
| 795 | H | CH₃ | H | H | H | 4-chloro-5-pyrimidyl |
| 796 | H | CH₃ | H | H | H | 2-bromo-5-pyrimidyl |
| 797 | H | CH₃ | H | H | H | 4-bromo-5-pyrimidyl |
| 798 | H | CH₃ | H | H | H | 2-methoxy-5-pyrimidyl |
| 799 | H | CH₃ | H | H | H | 4-methoxy-5-pyrimidyl |
| 800 | H | CH₃ | H | H | H | 2-trifluoromethoxy-5-pyrimidyl |
| 801 | H | CH₃ | H | H | H | 4-trifluoromethoxy-5-pyrimidyl |
| 802 | H | CH₃ | H | H | H | 2-methyl-5-pyrimidyl |
| 803 | H | CH₃ | H | H | H | 4-methyl-5-pyrimidyl |
| 804 | H | CH₃ | H | H | H | 2-trifluoromethyl-5-pyrimidyl |
| 805 | H | CH₃ | H | H | H | 4-trifluoromethyl-5-pyrimidyl |
| 806 | H | CH₃ | H | H | H | 2-cyano-5-pyrimidyl |
| 807 | H | CH₃ | H | H | H | 4-cyano-5-pyrimidyl |
| 808 | H | CH₃ | H | H | H | 2-nitro-5-pyrimidyl |
| 809 | H | CH₃ | H | H | H | 4-nitro-5-pyrimidyl |
| 810 | H | CH₃ | H | H | H | 2-methanesulfonyl-5-pyrimidyl |
| 811 | H | CH₃ | H | H | H | 4-methanesulfonyl-5-pyrimidyl |
| 812 | H | CH₃ | H | H | H | 2-pyrazinyl |
| 813 | H | CH₃ | H | H | H | 3-fluoro-2-pyrazinyl |
| 814 | H | CH₃ | H | H | H | 5-fluoro-2-pyrazinyl |
| 815 | H | CH₃ | H | H | H | 6-fluoro-2-pyrazinyl |
| 816 | H | CH₃ | H | H | H | 3-chloro-2-pyrazinyl |
| 817 | H | CH₃ | H | H | H | 5-chloro-2-pyrazinyl |
| 818 | H | CH₃ | H | H | H | 6-chloro-2-pyrazinyl |
| 819 | H | CH₃ | H | H | H | 3-bromo-2-pyrazinyl |
| 820 | H | CH₃ | H | H | H | 5-bromo-2-pyrazinyl |
| 821 | H | CH₃ | H | H | H | 6-bromo-2-pyrazinyl |
| 822 | H | CH₃ | H | H | H | 3-methoxy-2-pyrazinyl |
| 823 | H | CH₃ | H | H | H | 5-methoxy-2-pyrazinyl |
| 824 | H | CH₃ | H | H | H | 6-methoxy-2-pyrazinyl |
| 825 | H | CH₃ | H | H | H | 3-trifluoromethoxy-2-pyrazinyl |
| 826 | H | CH₃ | H | H | H | 5-trifluoromethoxy-2-pyrazinyl |
| 827 | H | CH₃ | H | H | H | 6-trifluoromethoxy-2-pyrazinyl |
| 828 | H | CH₃ | H | H | H | 3-methyl-2-pyrazinyl |
| 829 | H | CH₃ | H | H | H | 5-methyl-2-pyrazinyl |
| 830 | H | CH₃ | H | H | H | 6-methyl-2-pyrazinyl |
| 831 | H | CH₃ | H | H | H | 3-trifluoromethyl-2-pyrazinyl |
| 832 | H | CH₃ | H | H | H | 5-trifluoromethyl-2-pyrazinyl |
| 833 | H | CH₃ | H | H | H | 6-trifluoromethyl-2-pyrazinyl |
| 834 | H | CH₃ | H | H | H | 3-cyano-2-pyrazinyl |
| 835 | H | CH₃ | H | H | H | 5-cyano-2-pyrazinyl |
| 836 | H | CH₃ | H | H | H | 6-cyano-2-pyrazinyl |
| 837 | H | CH₃ | H | H | H | 3-nitro-2-pyrazinyl |
| 838 | H | CH₃ | H | H | H | 5-nitro-2-pyrazinyl |
| 839 | H | CH₃ | H | H | H | 6-nitro-2-pyrazinyl |
| 840 | H | CH₃ | H | H | H | 3-methylsulfonat-2-pyrazinyl |
| 841 | H | CH₃ | H | H | H | 5-methylsulfonate-2-pyrazinyl |
| 842 | H | CH₃ | H | H | H | 6-methylsulfonate-2-pyrazinyl |
| 843 | H | CH₃ | H | H | H | 2-furanyl |
| 844 | H | CH₃ | H | H | H | 3-fluoro-2-furanyl |
| 845 | H | CH₃ | H | H | H | 4-fluoro-2-furanyl |
| 846 | H | CH₃ | H | H | H | 5-fluoro-2-furanyl |
| 847 | H | CH₃ | H | H | H | 3-chloro-2-furanyl |
| 848 | H | CH₃ | H | H | H | 4-chloro-2-furanyl |
| 849 | H | CH₃ | H | H | H | 5-chloro-2-furanyl |
| 850 | H | CH₃ | H | H | H | 3-bromo-2-furanyl |
| 851 | H | CH₃ | H | H | H | 4-bromo-2-furanyl |
| 852 | H | CH₃ | H | H | H | 5-bromo-2-furanyl |
| 853 | H | CH₃ | H | H | H | 3-methoxy-2-furanyl |
| 854 | H | CH₃ | H | H | H | 4-methoxy-2-furanyl |
| 855 | H | CH₃ | H | H | H | 5-methoxy-2-furanyl |
| 856 | H | CH₃ | H | H | H | 3-trifluoromethoxy-2-furanyl |
| 857 | H | CH₃ | H | H | H | 4-trifluoromethoxy-2-furanyl |
| 858 | H | CH₃ | H | H | H | 5-trifluoromethoxy-2-furanyl |
| 859 | H | CH₃ | H | H | H | 3-methyl-2-furanyl |
| 860 | H | CH₃ | H | H | H | 4-methyl-2-furanyl |
| 861 | H | CH₃ | H | H | H | 5-methyl-2-furanyl |
| 862 | H | CH₃ | H | H | H | 3-trifluoromethyl-2-furanyl |
| 863 | H | CH₃ | H | H | H | 4-trifluoromethyl-2-furanyl |
| 864 | H | CH₃ | H | H | H | 5-trifluoromethyl-2-furanyl |
| 865 | H | CH₃ | H | H | H | 3-cyano-2-furanyl |
| 866 | H | CH₃ | H | H | H | 4-cyano-2-furanyl |
| 867 | H | CH₃ | H | H | H | 5-cyano-2-furanyl |
| 868 | H | CH₃ | H | H | H | 3-nitro-2-furanyl |
| 869 | H | CH₃ | H | H | H | 4-nitro-2-furanyl |
| 870 | H | CH₃ | H | H | H | 5-nitro-2-furanyl |
| 871 | H | CH₃ | H | H | H | 3-methanesulfonyl-2-furanyl |
| 872 | H | CH₃ | H | H | H | 4-methanesulfonyl-2-furanyl |
| 873 | H | CH₃ | H | H | H | 5-methansufonyl-2-furanyl |
| 874 | H | CH₃ | H | H | H | 3-furanyl |
| 875 | H | CH₃ | H | H | H | 3-fluoro-2-furanyl |
| 876 | H | CH₃ | H | H | H | 4-fluoro-2-furanyl |
| 877 | H | CH₃ | H | H | H | 5-fluoro-2-furanyl |
| 878 | H | CH₃ | H | H | H | 3-chloro-2-furanyl |
| 879 | H | CH₃ | H | H | H | 4-chloro-2-furanyl |
| 880 | H | CH₃ | H | H | H | 5-chloro-2-furanyl |
| 881 | H | CH₃ | H | H | H | 3-bromo-2-furanyl |
| 882 | H | CH₃ | H | H | H | 4-bromo-2-furanyl |
| 883 | H | CH₃ | H | H | H | 5-bromo-2-furanyl |
| 884 | H | CH₃ | H | H | H | 3-methoxy-2-furanyl |
| 885 | H | CH₃ | H | H | H | 4-methoxy-2-furanyl |
| 886 | H | CH₃ | H | H | H | 5-methoxy-2-furanyl |
| 887 | H | CH₃ | H | H | H | 3-trifluoromethoxy-2-furanyl |
| 888 | H | CH₃ | H | H | H | 4-trifluoromethoxy-2-furanyl |
| 889 | H | CH₃ | H | H | H | 5-trifluoromethoxy-2-furanyl |
| 890 | H | CH₃ | H | H | H | 3-methyl-2-furanyl |
| 891 | H | CH₃ | H | H | H | 4-methyl-2-furanyl |
| 892 | H | CH₃ | H | H | H | 5-methyl-2-furanyl |
| 893 | H | CH₃ | H | H | H | 3-trifluoromethyl-2-furanyl |
| 894 | H | CH₃ | H | H | H | 4-trifluoromethyl-2-furanyl |
| 895 | H | CH₃ | H | H | H | 5-trifluoromethyl-2-furanyl |
| 896 | H | CH₃ | H | H | H | 3-cyano-2-furanyl |

| Compound number | R⁵ | R⁶ | R⁷ | R⁸ | R⁹ | HetAr |
|---|---|---|---|---|---|---|
| 897 | H | CH₃ | H | H | H | 4-cyano-2-furanyl |
| 898 | H | CH₃ | H | H | H | 5-cyano-2-furanyl |
| 899 | H | CH₃ | H | H | H | 3-nitro-2-furanyl |
| 900 | H | CH₃ | H | H | H | 4-nitro-2-furanyl |
| 901 | H | CH₃ | H | H | H | 5-nitro-2-furanyl |
| 902 | H | CH₃ | H | H | H | 3-methanesulfonyl-2-furanyl |
| 903 | H | CH₃ | H | H | H | 4-methanesulfonyl-2-furanyl |
| 904 | H | CH₃ | H | H | H | 5-methanesufonyl-2-furanyl |
| 905 | H | CH₃ | H | H | H | 3-furanyl |
| 906 | H | CH₃ | H | H | H | 2-fluoro-3-furanyl |
| 907 | H | CH₃ | H | H | H | 4-fluoro-3-furanyl |
| 908 | H | CH₃ | H | H | H | 5-fluoro-3-furanyl |
| 909 | H | CH₃ | H | H | H | 2-chloro-3-furanyl |
| 910 | H | CH₃ | H | H | H | 4-chloro-3-furanyl |
| 911 | H | CH₃ | H | H | H | 5-chloro-3-furanyl |
| 912 | H | CH₃ | H | H | H | 2-bromo-3-furanyl |
| 913 | H | CH₃ | H | H | H | 4-bromo-3-furanyl |
| 914 | H | CH₃ | H | H | H | 5-bromo-3-furanyl |
| 915 | H | CH₃ | H | H | H | 2-methoxy-3-furanyl |
| 916 | H | CH₃ | H | H | H | 4-methoxy-3-furanyl |
| 917 | H | CH₃ | H | H | H | 5-methoxy-3-furanyl |
| 918 | H | CH₃ | H | H | H | 2-trifluoromethoxy-3-furanyl |
| 919 | H | CH₃ | H | H | H | 4-trifluoromethoxy-3-furanyl |
| 920 | H | CH₃ | H | H | H | 5-trifluoromethoxy-3-furanyl |
| 921 | H | CH₃ | H | H | H | 2-methyl-3-furanyl |
| 922 | H | CH₃ | H | H | H | 4-methyl-3-furanyl |
| 923 | H | CH₃ | H | H | H | 5-methyl-3-furanyl |
| 924 | H | CH₃ | H | H | H | 2-trifluoromethyl-3-furanyl |
| 925 | H | CH₃ | H | H | H | 4-trifluoromethyl-3-furanyl |
| 926 | H | CH₃ | H | H | H | 5-trifluoromethyl-3-furanyl |
| 927 | H | CH₃ | H | H | H | 2-cyano-3-furanyl |
| 928 | H | CH₃ | H | H | H | 4-cyano-3-furanyl |
| 929 | H | CH₃ | H | H | H | 5-cyano-3-furanyl |
| 930 | H | CH₃ | H | H | H | 2-nitro-3-furanyl |
| 931 | H | CH₃ | H | H | H | 4-nitro-3-furanyl |
| 932 | H | CH₃ | H | H | H | 5-nitro-3-furanyl |
| 933 | H | CH₃ | H | H | H | 2-methanesulfonyl-3-furanyl |
| 934 | H | CH₃ | H | H | H | 4-methanesulfonyl-3-furanyl |
| 935 | H | CH₃ | H | H | H | 5-methanesufonyl-3-furanyl |
| 936 | H | CH₃ | H | H | H | 2-thiophenyl |
| 937 | H | CH₃ | H | H | H | 3-fluoro-2-thiophenyl |
| 938 | H | CH₃ | H | H | H | 4-fluoro-2-thiophenyl |
| 939 | H | CH₃ | H | H | H | 5-fluoro-2-thiophenyl |
| 940 | H | CH₃ | H | H | H | 3-chloro-2-thiophenyl |
| 941 | H | CH₃ | H | H | H | 4-chloro-2-thiophenyl |
| 942 | H | CH₃ | H | H | H | 5-chloro-2-thiophenyl |
| 943 | H | CH₃ | H | H | H | 3-bromo-2-thiophenyl |
| 944 | H | CH₃ | H | H | H | 4-bromo-2-thiophenyl |
| 945 | H | CH₃ | H | H | H | 5-bromo-2-thiophenyl |
| 946 | H | CH₃ | H | H | H | 3-methoxy-2-thiophenyl |
| 947 | H | CH₃ | H | H | H | 4-methoxy-2-thiophenyl |
| 948 | H | CH₃ | H | H | H | 5-methoxy-2-thiophenyl |
| 949 | H | CH₃ | H | H | H | 3-trifluoromethoxy-2-thiophenyl |
| 950 | H | CH₃ | H | H | H | 4-trifluoromethoxy-2-thiophenyl |
| 951 | H | CH₃ | H | H | H | 5-trifluoromethoxy-2-thiophenyl |
| 952 | H | CH₃ | H | H | H | 3-methyl-2-thiophenyl |
| 953 | H | CH₃ | H | H | H | 4-methyl-2-thiophenyl |
| 954 | H | CH₃ | H | H | H | 5-methyl-2-thiophenyl |
| 955 | H | CH₃ | H | H | H | 3-trifluoromethyl-2-thiophenyl |
| 956 | H | CH₃ | H | H | H | 4-trifluoromethyl-2-thiophenyl |
| 957 | H | CH₃ | H | H | H | 5-trifluoromethyl-2-thiophenyl |
| 958 | H | CH₃ | H | H | H | 3-cyano-2-thiophenyl |
| 959 | H | CH₃ | H | H | H | 4-cyano-2-thiophenyl |
| 960 | H | CH₃ | H | H | H | 5-cyano-2-thiophenyl |
| 961 | H | CH₃ | H | H | H | 3-nitro-2-thiophenyl |
| 962 | H | CH₃ | H | H | H | 4-nitro-2-thiophenyl |
| 963 | H | CH₃ | H | H | H | 5-nitro-2-thiophenyl |
| 964 | H | CH₃ | H | H | H | 3-methanesulfonyl-2-thiophenyl |
| 965 | H | CH₃ | H | H | H | 4-methanesulfonyl-2-thiophenyl |
| 966 | H | CH₃ | H | H | H | 5-methanesufonyl-2-thiophenyl |
| 967 | H | CH₃ | H | H | H | 3-thiophenyl |
| 968 | H | CH₃ | H | H | H | 3-fluoro-2-thiophenyl |
| 969 | H | CH₃ | H | H | H | 4-fluoro-2-thiophenyl |
| 970 | H | CH₃ | H | H | H | 5-fluoro-2-thiophenyl |
| 971 | H | CH₃ | H | H | H | 3-chloro-2-thiophenyl |
| 972 | H | CH₃ | H | H | H | 4-chloro-2-thiophenyl |
| 973 | H | CH₃ | H | H | H | 5-chloro-2-thiophenyl |
| 974 | H | CH₃ | H | H | H | 3-bromo-2-thiophenyl |
| 975 | H | CH₃ | H | H | H | 4-bromo-2-thiophenyl |
| 976 | H | CH₃ | H | H | H | 5-bromo-2-thiophenyl |
| 977 | H | CH₃ | H | H | H | 3-methoxy-2-thiophenyl |
| 978 | H | CH₃ | H | H | H | 4-methoxy-2-thiophenyl |
| 979 | H | CH₃ | H | H | H | 5-methoxy-2-thiophenyl |
| 980 | H | CH₃ | H | H | H | 3-trifluoromethoxy-2-thiophenyl |
| 981 | H | CH₃ | H | H | H | 4-trifluoromethoxy-2-thiophenyl |
| 982 | H | CH₃ | H | H | H | 5-trifluoromethoxy-2-thiophenyl |
| 983 | H | CH₃ | H | H | H | 3-methyl-2-thiophenyl |
| 984 | H | CH₃ | H | H | H | 4-methyl-2-thiophenyl |
| 985 | H | CH₃ | H | H | H | 5-methyl-2-thiophenyl |
| 986 | H | CH₃ | H | H | H | 3-trifluoromethyl-2-thiophenyl |
| 987 | H | CH₃ | H | H | H | 4-trifluoromethyl-2-thiophenyl |
| 988 | H | CH₃ | H | H | H | 5-trifluoromethyl-2-thiophenyl |
| 989 | H | CH₃ | H | H | H | 3-cyano-2-thiophenyl |
| 990 | H | CH₃ | H | H | H | 4-cyano-2-thiophenyl |
| 991 | H | CH₃ | H | H | H | 5-cyano-2-thiophenyl |
| 992 | H | CH₃ | H | H | H | 3-nitro-2-thiophenyl |
| 993 | H | CH₃ | H | H | H | 4-nitro-2-thiophenyl |
| 994 | H | CH₃ | H | H | H | 5-nitro-2-thiophenyl |
| 995 | H | CH₃ | H | H | H | 3-methanesulfonyl-2-thiophenyl |
| 996 | H | CH₃ | H | H | H | 4-methanesulfonyl-2-thiophenyl |
| 997 | H | CH₃ | H | H | H | 5-methanesufonyl-2-thiophenyl |
| 998 | H | CH₃ | H | H | H | 3-thiophenyl |
| 999 | H | CH₃ | H | H | H | 2-fluoro-3-thiophenyl |
| 1000 | H | CH₃ | H | H | H | 4-fluoro-3-thiophenyl |
| 1001 | H | CH₃ | H | H | H | 5-fluoro-3-thiophenyl |
| 1002 | H | CH₃ | H | H | H | 2-chloro-3-thiophenyl |
| 1003 | H | CH₃ | H | H | H | 4-chloro-3-thiophenyl |
| 1004 | H | CH₃ | H | H | H | 5-chloro-3-thiophenyl |
| 1005 | H | CH₃ | H | H | H | 2-bromo-3-thiophenyl |
| 1006 | H | CH₃ | H | H | H | 4-bromo-3-thiophenyl |
| 1007 | H | CH₃ | H | H | H | 5-bromo-3-thiophenyl |
| 1008 | H | CH₃ | H | H | H | 2-methoxy-3-thiophenyl |
| 1009 | H | CH₃ | H | H | H | 4-methoxy-3-thiophenyl |
| 1010 | H | CH₃ | H | H | H | 5-methoxy-3-thiophenyl |
| 1011 | H | CH₃ | H | H | H | 2-trifluoromethoxy-3-thiophenyl |
| 1012 | H | CH₃ | H | H | H | 4-trifluoromethoxy-3-thiophenyl |
| 1013 | H | CH₃ | H | H | H | 5-trifluoromethoxy-3-thiophenyl |
| 1014 | H | CH₃ | H | H | H | 2-methyl-3-thiophenyl |

| Compound number | R⁵ | R⁶ | R⁷ | R⁸ | R⁹ | HetAr |
|---|---|---|---|---|---|---|
| 1015 | H | CH₃ | H | H | H | 4-methyl-3-thiophenyl |
| 1016 | H | CH₃ | H | H | H | 5-methyl-3-thiophenyl |
| 1017 | H | CH₃ | H | H | H | 2-trifluoromethyl-3-thiophenyl |
| 1018 | H | CH₃ | H | H | H | 4-trifluoromethyl-3-thiophenyl |
| 1019 | H | CH₃ | H | H | H | 5-trifluoromethyl-3-thiophenyl |
| 1020 | H | CH₃ | H | H | H | 2-cyano-3-thiophenyl |
| 1021 | H | CH₃ | H | H | H | 4-cyano-3-thiophenyl |
| 1022 | H | CH₃ | H | H | H | 5-cyano-3-thiophenyl |
| 1023 | H | CH₃ | H | H | H | 2-nitro-3-thiophenyl |
| 1024 | H | CH₃ | H | H | H | 4-nitro-3-thiophenyl |
| 1025 | H | CH₃ | H | H | H | 5-nitro-3-thiophenyl |
| 1026 | H | CH₃ | H | H | H | 2-methanesulfonyl-3-thiophenyl |
| 1027 | H | CH₃ | H | H | H | 4-methanesulfonyl-3-thiophenyl |
| 1028 | H | CH₃ | H | H | H | 5-methanesufonyl-3-thiophenyl |
| 1029 | H | CH₃ | H | H | H | 2-oxazole |
| 1030 | H | CH₃ | H | H | H | 4-fluoro-2-oxazole |
| 1031 | H | CH₃ | H | H | H | 5-fluoro-2-oxazole |
| 1032 | H | CH₃ | H | H | H | 4-chloro-2-oxazole |
| 1033 | H | CH₃ | H | H | H | 5-chloro-2-oxazole |
| 1034 | H | CH₃ | H | H | H | 4-bromo-2-oxazole |
| 1035 | H | CH₃ | H | H | H | 5-bromo-2-oxazole |
| 1036 | H | CH₃ | H | H | H | 4-methoxy-2-oxazole |
| 1037 | H | CH₃ | H | H | H | 5-methoxy-2-oxazole |
| 1038 | H | CH₃ | H | H | H | 4-trifluoromethoxy-2-oxazole |
| 1039 | H | CH₃ | H | H | H | 5-trifluoromethoxy-2-oxazole |
| 1040 | H | CH₃ | H | H | H | 4-methyl-2-oxazole |
| 1041 | H | CH₃ | H | H | H | 5-methyl-2-oxazole |
| 1042 | H | CH₃ | H | H | H | 4-trifluoromethyl-2-oxazole |
| 1043 | H | CH₃ | H | H | H | 5-trifluoromethyl-2-oxazole |
| 1044 | H | CH₃ | H | H | H | 4-cyano-2-oxazole |
| 1045 | H | CH₃ | H | H | H | 5-cyano-2-oxazole |
| 1046 | H | CH₃ | H | H | H | 4-nitro-2-oxazole |
| 1047 | H | CH₃ | H | H | H | 5-nitro-2-oxazole |
| 1048 | H | CH₃ | H | H | H | 4-methanesulfonyl-2-oxazole |
| 1049 | H | CH₃ | H | H | H | 5-methanesulfonyl-2-oxazole |
| 1050 | H | CH₃ | H | H | H | 4-oxazole |
| 1051 | H | CH₃ | H | H | H | 2-fluoro-4-oxazole |
| 1052 | H | CH₃ | H | H | H | 5-fluoro-4-oxazole |
| 1053 | H | CH₃ | H | H | H | 2-chloro-4-oxazole |
| 1054 | H | CH₃ | H | H | H | 5-chloro-4-oxazole |
| 1055 | H | CH₃ | H | H | H | 2-bromo-4-oxazole |
| 1056 | H | CH₃ | H | H | H | 5-bromo-4-oxazole |
| 1057 | H | CH₃ | H | H | H | 2-methoxy-4-oxazole |
| 1058 | H | CH₃ | H | H | H | 5-methoxy-4-oxazole |
| 1059 | H | CH₃ | H | H | H | 2-trifluoromethoxy-4-oxazole |
| 1060 | H | CH₃ | H | H | H | 5-trifluoromethoxy-4-oxazole |
| 1061 | H | CH₃ | H | H | H | 2-methyl-4-oxazole |
| 1062 | H | CH₃ | H | H | H | 5-methyl-4-oxazole |
| 1063 | H | CH₃ | H | H | H | 4-trifluoromethyl-4-oxazole |
| 1064 | H | CH₃ | H | H | H | 5-trifluoromethyl-4-oxazole |
| 1065 | H | CH₃ | H | H | H | 4-cyano-4-oxazole |
| 1066 | H | CH₃ | H | H | H | 5-cyano-4-oxazole |
| 1067 | H | CH₃ | H | H | H | 4-nitro-4-oxazole |
| 1068 | H | CH₃ | H | H | H | 5-nitro-4-oxazole |
| 1069 | H | CH₃ | H | H | H | 4-methanesulfonyl-4-oxazole |
| 1070 | H | CH₃ | H | H | H | 5-methanesulfonyl-4-oxazole |
| 1071 | H | CH₃ | H | H | H | 5-oxazole |
| 1072 | H | CH₃ | H | H | H | 2-fluoro-5-oxazole |
| 1073 | H | CH₃ | H | H | H | 4-fluoro-5-oxazole |
| 1074 | H | CH₃ | H | H | H | 2-chloro-5-oxazole |
| 1075 | H | CH₃ | H | H | H | 4-chloro-5-oxazole |
| 1076 | H | CH₃ | H | H | H | 2-bromo-5-oxazole |
| 1077 | H | CH₃ | H | H | H | 4-bromo-5-oxazole |
| 1078 | H | CH₃ | H | H | H | 2-methoxy-5-oxazole |
| 1079 | H | CH₃ | H | H | H | 4-methoxy-5-oxazole |
| 1080 | H | CH₃ | H | H | H | 2-trifluoromethoxy-5-oxazole |
| 1081 | H | CH₃ | H | H | H | 4-trifluoromethoxy-5-oxazole |
| 1082 | H | CH₃ | H | H | H | 2-methyl-5-oxazole |
| 1083 | H | CH₃ | H | H | H | 4-methyl-5-oxazole |
| 1084 | H | CH₃ | H | H | H | 2-trifluoromethyl-5-oxazole |
| 1085 | H | CH₃ | H | H | H | 4-trifluoromethyl-5-oxazole |
| 1086 | H | CH₃ | H | H | H | 2-cyano-5-oxazole |
| 1087 | H | CH₃ | H | H | H | 4-cyano-5-oxazole |
| 1088 | H | CH₃ | H | H | H | 2-nitro-5-oxazole |
| 1089 | H | CH₃ | H | H | H | 4-nitro-5-oxazole |
| 1090 | H | CH₃ | H | H | H | 2-methanesulfonyl-5-oxazole |
| 1091 | H | CH₃ | H | H | H | 4-methanesulfonyl-5-oxazole |
| 1092 | H | CH₃ | H | H | H | 2-thiazole |
| 1093 | H | CH₃ | H | H | H | 4-fluoro-2-thiazole |
| 1094 | H | CH₃ | H | H | H | 5-fluoro-2-thiazole |
| 1095 | H | CH₃ | H | H | H | 4-chloro-2-thiazole |
| 1096 | H | CH₃ | H | H | H | 5-chloro-2-thiazole |
| 1097 | H | CH₃ | H | H | H | 4-bromo-2-thiazole |
| 1098 | H | CH₃ | H | H | H | 5-bromo-2-thiazole |
| 1099 | H | CH₃ | H | H | H | 4-methoxy-2-thiazole |
| 1100 | H | CH₃ | H | H | H | 5-methoxy-2-thiazole |
| 1101 | H | CH₃ | H | H | H | 4-trifluoromethoxy-2-thiazole |
| 1102 | H | CH₃ | H | H | H | 5-trifluoromethoxy-2-thiazole |
| 1103 | H | CH₃ | H | H | H | 4-methyl-2-thiazole |
| 1104 | H | CH₃ | H | H | H | 5-methyl-2-thiazole |
| 1105 | H | CH₃ | H | H | H | 4-trifluoromethyl-2-thiazole |
| 1106 | H | CH₃ | H | H | H | 5-trifluoromethyl-2-thiazole |
| 1107 | H | CH₃ | H | H | H | 4-cyano-2-thiazole |
| 1108 | H | CH₃ | H | H | H | 5-cyano-2-thiazole |
| 1109 | H | CH₃ | H | H | H | 4-nitro-2-thiazole |
| 1110 | H | CH₃ | H | H | H | 5-nitro-2-thiazole |
| 1111 | H | CH₃ | H | H | H | 4-methanesulfonyl-2-thiazole |
| 1112 | H | CH₃ | H | H | H | 5-methanesulfonyl-2-thiazole |
| 1113 | H | CH₃ | H | H | H | 4-thiazole |
| 1114 | H | CH₃ | H | H | H | 2-fluoro-4-thiazole |
| 1115 | H | CH₃ | H | H | H | 5-fluoro-4-thiazole |
| 1116 | H | CH₃ | H | H | H | 2-chloro-4-thiazole |
| 1117 | H | CH₃ | H | H | H | 5-chloro-4-thiazole |
| 1118 | H | CH₃ | H | H | H | 2-bromo-4-thiazole |
| 1119 | H | CH₃ | H | H | H | 5-bromo-4-thiazole |
| 1120 | H | CH₃ | H | H | H | 2-methoxy-4-thiazole |
| 1121 | H | CH₃ | H | H | H | 5-methoxy-4-thiazole |
| 1122 | H | CH₃ | H | H | H | 2-trifluoromethoxy-4-thiazole |
| 1123 | H | CH₃ | H | H | H | 5-trifluoromethoxy-4-thiazole |
| 1124 | H | CH₃ | H | H | H | 2-methyl-4-thiazole |
| 1125 | H | CH₃ | H | H | H | 5-methyl-4-thiazole |
| 1126 | H | CH₃ | H | H | H | 4-trifluoromethyl-4-thiazole |
| 1127 | H | CH₃ | H | H | H | 5-trifluoromethyl-4-thiazole |
| 1128 | H | CH₃ | H | H | H | 4-cyano-4-thiazole |
| 1129 | H | CH₃ | H | H | H | 5-cyano-4-thiazole |
| 1130 | H | CH₃ | H | H | H | 4-nitro-4-thiazole |
| 1131 | H | CH₃ | H | H | H | 5-nitro-4-thiazole |

-continued

| Compound number | R⁵ | R⁶ | R⁷ | R⁸ | R⁹ | HetAr |
|---|---|---|---|---|---|---|
| 1132 | H | CH₃ | H | H | H | 4-methanesulfonyl-4-thiazole |
| 1133 | H | CH₃ | H | H | H | 5-methanesulfonyl-4-thiazole |
| 1134 | H | CH₃ | H | H | H | 5-thiazole |
| 1135 | H | CH₃ | H | H | H | 2-fluoro-5-thiazole |
| 1136 | H | CH₃ | H | H | H | 4-fluoro-5-thiazole |
| 1137 | H | CH₃ | H | H | H | 2-chloro-5-thiazole |
| 1138 | H | CH₃ | H | H | H | 4-chloro-5-thiazole |
| 1139 | H | CH₃ | H | H | H | 2-bromo-5-thiazole |
| 1140 | H | CH₃ | H | H | H | 4-bromo-5-thiazole |
| 1141 | H | CH₃ | H | H | H | 2-methoxy-5-thiazole |
| 1142 | H | CH₃ | H | H | H | 4-methoxy-5-thiazole |
| 1143 | H | CH₃ | H | H | H | 2-trifluoromethoxy-5-thiazole |
| 1144 | H | CH₃ | H | H | H | 4-trifluoromethoxy-5-thiazole |
| 1145 | H | CH₃ | H | H | H | 2-methyl-5-thiazole |
| 1146 | H | CH₃ | H | H | H | 4-methyl-5-thiazole |
| 1147 | H | CH₃ | H | H | H | 2-trifluoromethyl-5-thiazole |
| 1148 | H | CH₃ | H | H | H | 4-trifluoromethyl-5-thiazole |
| 1149 | H | CH₃ | H | H | H | 2-cyano-5-thiazole |
| 1150 | H | CH₃ | H | H | H | 4-cyano-5-thiazole |
| 1151 | H | CH₃ | H | H | H | 2-nitro-5-thiazole |
| 1152 | H | CH₃ | H | H | H | 4-nitro-5-thiazole |
| 1153 | H | CH₃ | H | H | H | 2-methanesulfonyl-5-thiazole |
| 1154 | H | CH₃ | CH₃ | H | H | 4-methanesulfonyl-5-thiazole |
| 1155 | H | CH₃ | CH₃ | H | H | 2-pyridyl |
| 1156 | H | CH₃ | CH₃ | H | H | 3-fluoro-2-pyridyl |
| 1157 | H | CH₃ | CH₃ | H | H | 4-fluoro-2-pyridyl |
| 1158 | H | CH₃ | CH₃ | H | H | 5-fluoro-2-pyridyl |
| 1159 | H | CH₃ | CH₃ | H | H | 6-fluoro-2-pyridyl |
| 1160 | H | CH₃ | CH₃ | H | H | 3-chloro-2-pyridyl |
| 1161 | H | CH₃ | CH₃ | H | H | 4-chloro-2-pyridyl |
| 1162 | H | CH₃ | CH₃ | H | H | 5-chloro-2-pyridyl |
| 1163 | H | CH₃ | CH₃ | H | H | 6-chloro-2-pyridyl |
| 1164 | H | CH₃ | CH₃ | H | H | 3-methyl-2-pyridyl |
| 1165 | H | CH₃ | CH₃ | H | H | 4-methyl-2-pyridyl |
| 1166 | H | CH₃ | CH₃ | H | H | 5-methyl-2-pyridyl |
| 1167 | H | CH₃ | CH₃ | H | H | 6-methyl-2-pyridyl |
| 1168 | H | CH₃ | CH₃ | H | H | 3-trifluoromethyl-2-pyridyl |
| 1169 | H | CH₃ | CH₃ | H | H | 4-trifluoromethyl-2-pyridyl |
| 1170 | H | CH₃ | CH₃ | H | H | 5-trifluoromethyl-2-pyridyl |
| 1171 | H | CH₃ | CH₃ | H | H | 6-trifluoromethyl-2-pyridyl |
| 1172 | H | CH₃ | CH₃ | H | H | 3-methoxy-2-pyridyl |
| 1173 | H | CH₃ | CH₃ | H | H | 4-methoxy-2-pyridyl |
| 1174 | H | CH₃ | CH₃ | H | H | 5-methoxy-2-pyridyl |
| 1175 | H | CH₃ | CH₃ | H | H | 6-methoxy-2-pyridyl |
| 1176 | H | CH₃ | CH₃ | H | H | 3-trifluoromethoxy-2-pyridyl |
| 1177 | H | CH₃ | CH₃ | H | H | 4-trifluoromethoxy-2-pyridyl |
| 1178 | H | CH₃ | CH₃ | H | H | 5-trifluoromethoxy-2-pyridyl |
| 1179 | H | CH₃ | CH₃ | H | H | 6-trifluoromethoxy-2-pyridyl |
| 1180 | H | CH₃ | CH₃ | H | H | 3-cyano-2-pyridyl |
| 1181 | H | CH₃ | CH₃ | H | H | 4-cyano-2-pyridyl |
| 1182 | H | CH₃ | CH₃ | H | H | 5-cyano-2-pyridyl |
| 1183 | H | CH₃ | CH₃ | H | H | 6-cyano-2-pyridyl |
| 1184 | H | CH₃ | CH₃ | H | H | 3-nitro-2-pyridyl |
| 1185 | H | CH₃ | CH₃ | H | H | 4-nitro-2-pyridyl |
| 1186 | H | CH₃ | CH₃ | H | H | 5-nitro-2-pyridyl |
| 1187 | H | CH₃ | CH₃ | H | H | 6-nitro-2-pyridyl |
| 1188 | H | CH₃ | CH₃ | H | H | 3-methanesulfonyl-2-pyridyl |
| 1189 | H | CH₃ | CH₃ | H | H | 4-methanesulfonyl-2-pyridyl |
| 1190 | H | CH₃ | CH₃ | H | H | 5-methanesulfonyl-2-pyridyl |
| 1191 | H | CH₃ | CH₃ | H | H | 6-methanesulfonyl-2-pyridyl |
| 1192 | H | CH₃ | CH₃ | H | H | 3-pyridyl |
| 1193 | H | CH₃ | CH₃ | H | H | 2-fluoro-3-pyridyl |
| 1194 | H | CH₃ | CH₃ | H | H | 4-fluoro-3-pyridyl |
| 1195 | H | CH₃ | CH₃ | H | H | 5-fluoro-3-pyridyl |
| 1196 | H | CH₃ | CH₃ | H | H | 6-fluoro-3-pyridyl |
| 1197 | H | CH₃ | CH₃ | H | H | 2-chloro-3-pyridyl |
| 1198 | H | CH₃ | CH₃ | H | H | 4-chloro-3-pyridyl |
| 1199 | H | CH₃ | CH₃ | H | H | 5-chloro-3-pyridyl |
| 1200 | H | CH₃ | CH₃ | H | H | 6-chloro-3-pyridyl |
| 1201 | H | CH₃ | CH₃ | H | H | 2-bromo-3-pyridyl |
| 1202 | H | CH₃ | CH₃ | H | H | 4-bromo-3-pyridyl |
| 1203 | H | CH₃ | CH₃ | H | H | 5-bromo-3-pyridyl |
| 1204 | H | CH₃ | CH₃ | H | H | 6-bromo-3-pyridyl |
| 1205 | H | CH₃ | CH₃ | H | H | 2-methoxy-3-pyridyl |
| 1206 | H | CH₃ | CH₃ | H | H | 4-methoxy-3-pyridyl |
| 1207 | H | CH₃ | CH₃ | H | H | 5-methoxy-3-pyridyl |
| 1208 | H | CH₃ | CH₃ | H | H | 6-methoxy-3-pyridyl |
| 1209 | H | CH₃ | CH₃ | H | H | 2-trifluoromethoxy-3-pyridyl |
| 1210 | H | CH₃ | CH₃ | H | H | 4-trifluoromethoxy-3-pyridyl |
| 1211 | H | CH₃ | CH₃ | H | H | 5-trifluoromethoxy-3-pyridyl |
| 1212 | H | CH₃ | CH₃ | H | H | 6-trifluoromethoxy-3-pyridyl |
| 1213 | H | CH₃ | CH₃ | H | H | 2-methyl-3-pyridyl |
| 1214 | H | CH₃ | CH₃ | H | H | 4-methyl-3-pyridyl |
| 1215 | H | CH₃ | CH₃ | H | H | 5-methyl-3-pyridyl |
| 1216 | H | CH₃ | CH₃ | H | H | 6-methyl-3-pyridyl |
| 1217 | H | CH₃ | CH₃ | H | H | 2-trifluoromethyl-3-pyridyl |
| 1218 | H | CH₃ | CH₃ | H | H | 4-trifluoromethyl-3-pyridyl |
| 1219 | H | CH₃ | CH₃ | H | H | 5-trifluoromethyl-3-pyridyl |
| 1220 | H | CH₃ | CH₃ | H | H | 6-trifluoromethyl-3-pyridyl |
| 1221 | H | CH₃ | CH₃ | H | H | 2-cyano-3-pyridyl |
| 1222 | H | CH₃ | CH₃ | H | H | 4-cyano-3-pyridyl |
| 1223 | H | CH₃ | CH₃ | H | H | 5-cyano-3-pyridyl |
| 1224 | H | CH₃ | CH₃ | H | H | 6-cyano-3-pyridyl |
| 1225 | H | CH₃ | CH₃ | H | H | 2-nitro-3-pyridyl |
| 1226 | H | CH₃ | CH₃ | H | H | 4-nitro-3-pyridyl |
| 1227 | H | CH₃ | CH₃ | H | H | 5-nitro-3-pyridyl |
| 1228 | H | CH₃ | CH₃ | H | H | 6-nitro-3-pyridyl |
| 1229 | H | CH₃ | CH₃ | H | H | 2-methanesulfonyl-3-pyridyl |
| 1230 | H | CH₃ | CH₃ | H | H | 4-methanesulfonyl-3-pyridyl |
| 1231 | H | CH₃ | CH₃ | H | H | 5-methanesulfonyl-3-pyridyl |
| 1232 | H | CH₃ | CH₃ | H | H | 6-methanesulfonyl-3-pyridyl |
| 1233 | H | CH₃ | CH₃ | H | H | 4-pyridyl |
| 1234 | H | CH₃ | CH₃ | H | H | 2-fluoro-4-pyridyl |
| 1235 | H | CH₃ | CH₃ | H | H | 3-fluoro-4-pyridyl |
| 1236 | H | CH₃ | CH₃ | H | H | 2-chloro-4-pyridyl |
| 1237 | H | CH₃ | CH₃ | H | H | 3-chloro-4-pyridyl |
| 1238 | H | CH₃ | CH₃ | H | H | 2-bromo-4-pyridyl |
| 1239 | H | CH₃ | CH₃ | H | H | 3-bromo-4-pyridyl |
| 1240 | H | CH₃ | CH₃ | H | H | 2-methoxy-4-pyridyl |
| 1241 | H | CH₃ | CH₃ | H | H | 3-methoxy-4-pyridyl |
| 1242 | H | CH₃ | CH₃ | H | H | 2-trifluoromethoxy-4-pyridyl |
| 1243 | H | CH₃ | CH₃ | H | H | 3-trifluoromethoxy-4-pyridyl |
| 1244 | H | CH₃ | CH₃ | H | H | 2-methyl-4-pyridyl |
| 1245 | H | CH₃ | CH₃ | H | H | 3-methyl-4-pyridyl |
| 1246 | H | CH₃ | CH₃ | H | H | 2-trifluoromethyl-4-pyridyl |
| 1247 | H | CH₃ | CH₃ | H | H | 3-trifluoromethyl-4-pyridyl |
| 1248 | H | CH₃ | CH₃ | H | H | 2-cyano-4-pyridyl |
| 1249 | H | CH₃ | CH₃ | H | H | 3-cyano-4-pyridyl |
| 1250 | H | CH₃ | CH₃ | H | H | 2-nitro-4-pyridyl |
| 1251 | H | CH₃ | CH₃ | H | H | 3-nitro-4-pyridyl |

| Compound number | R⁵ | R⁶ | R⁷ | R⁸ | R⁹ | HetAr |
|---|---|---|---|---|---|---|
| 1252 | H | CH₃ | CH₃ | H | H | 2-methanesulfonyl-4-pyridyl |
| 1253 | H | CH₃ | CH₃ | H | H | 3-methanesulfonyl-4-pyridyl |
| 1254 | H | CH₃ | CH₃ | H | H | 2-pyridazinyl |
| 1255 | H | CH₃ | CH₃ | H | H | 4-fluoro-2-pyridazinyl |
| 1256 | H | CH₃ | CH₃ | H | H | 5-fluoro-2-pyridazinyl |
| 1257 | H | CH₃ | CH₃ | H | H | 6-fluoro-2-pyridazinyl |
| 1258 | H | CH₃ | CH₃ | H | H | 4-chloro-2-pyridazinyl |
| 1259 | H | CH₃ | CH₃ | H | H | 5-chloro-2-pyridazinyl |
| 1260 | H | CH₃ | CH₃ | H | H | 6-chloro-2-pyridazinyl |
| 1261 | H | CH₃ | CH₃ | H | H | 4-bromo-2-pyridazinyl |
| 1262 | H | CH₃ | CH₃ | H | H | 5-bromo-2-pyridazinyl |
| 1263 | H | CH₃ | CH₃ | H | H | 6-bromo-2-pyridazinyl |
| 1264 | H | CH₃ | CH₃ | H | H | 4-methoxy-2-pyridazinyl |
| 1265 | H | CH₃ | CH₃ | H | H | 5-methoxy-2-pyridazinyl |
| 1266 | H | CH₃ | CH₃ | H | H | 6-methoxy-2-pyridazinyl |
| 1267 | H | CH₃ | CH₃ | H | H | 4-trifluoromethoxy-2-pyridazinyl |
| 1268 | H | CH₃ | CH₃ | H | H | 5-trifluoromethoxy-2-pyridazinyl |
| 1269 | H | CH₃ | CH₃ | H | H | 6-trifluoromethoxy-2-pyridazinyl |
| 1270 | H | CH₃ | CH₃ | H | H | 4-methyl-2-pyridazinyl |
| 1271 | H | CH₃ | CH₃ | H | H | 5-methyl-2-pyridazinyl |
| 1272 | H | CH₃ | CH₃ | H | H | 6-methyl-2-pyridazinyl |
| 1273 | H | CH₃ | CH₃ | H | H | 4-trifluoromethyl-2-pyridazinyl |
| 1274 | H | CH₃ | CH₃ | H | H | 5-trifluoromethyl-2-pyridazinyl |
| 1275 | H | CH₃ | CH₃ | H | H | 6-trifluoromethyl-2-pyridazinyl |
| 1276 | H | CH₃ | CH₃ | H | H | 4-cyano-2-pyridazinyl |
| 1277 | H | CH₃ | CH₃ | H | H | 5-cyano-2-pyridazinyl |
| 1278 | H | CH₃ | CH₃ | H | H | 6-cyano-2-pyridazinyl |
| 1279 | H | CH₃ | CH₃ | H | H | 4-nitro-2-pyridazinyl |
| 1280 | H | CH₃ | CH₃ | H | H | 5-nitro-2-pyridazinyl |
| 1281 | H | CH₃ | CH₃ | H | H | 6-nitro-2-pyridazinyl |
| 1282 | H | CH₃ | CH₃ | H | H | 4-methanesulfonyl-2-pyridazinyl |
| 1283 | H | CH₃ | CH₃ | H | H | 5-methanesulfonyl-2-pyridazinyl |
| 1284 | H | CH₃ | CH₃ | H | H | 6-methanesulfonyl-2-pyridazinyl |
| 1285 | H | CH₃ | CH₃ | H | H | 3-pyridazinyl |
| 1286 | H | CH₃ | CH₃ | H | H | 2-fluoro-3-pyridazinyl |
| 1287 | H | CH₃ | CH₃ | H | H | 5-fluoro-3-pyridazinyl |
| 1288 | H | CH₃ | CH₃ | H | H | 6-fluoro-3-pyridazinyl |
| 1289 | H | CH₃ | CH₃ | H | H | 2-chloro-3-pyridazinyl |
| 1290 | H | CH₃ | CH₃ | H | H | 5-chloro-3-pyridazinyl |
| 1291 | H | CH₃ | CH₃ | H | H | 6-chloro-3-pyridazinyl |
| 1292 | H | CH₃ | CH₃ | H | H | 2-bromo-3-pyridazinyl |
| 1293 | H | CH₃ | CH₃ | H | H | 5-bromo-3-pyridazinyl |
| 1294 | H | CH₃ | CH₃ | H | H | 6-bromo-3-pyridazinyl |
| 1295 | H | CH₃ | CH₃ | H | H | 2-methoxy-3-pyridazinyl |
| 1296 | H | CH₃ | CH₃ | H | H | 5-methoxy-3-pyridazinyl |
| 1297 | H | CH₃ | CH₃ | H | H | 6-methoxy-3-pyridazinyl |
| 1298 | H | CH₃ | CH₃ | H | H | 2-trifluoromethoxy-3-pyridazinyl |
| 1299 | H | CH₃ | CH₃ | H | H | 5-trifluoromethoxy-3-pyridazinyl |
| 1300 | H | CH₃ | CH₃ | H | H | 6-trifluoromethoxy-3-pyridazinyl |
| 1301 | H | CH₃ | CH₃ | H | H | 2-methyl-3-pyridazinyl |
| 1302 | H | CH₃ | CH₃ | H | H | 5-methyl-3-pyridazinyl |
| 1303 | H | CH₃ | CH₃ | H | H | 6-methyl-3-pyridazinyl |
| 1304 | H | CH₃ | CH₃ | H | H | 2-trifluoromethyl-3-pyridazinyl |
| 1305 | H | CH₃ | CH₃ | H | H | 5-trifluoromethyl-3-pyridazinyl |
| 1306 | H | CH₃ | CH₃ | H | H | 6-trifluoromethyl-3-pyridazinyl |
| 1307 | H | CH₃ | CH₃ | H | H | 2-cyano-3-pyridazinyl |
| 1308 | H | CH₃ | CH₃ | H | H | 5-cyano-3-pyridazinyl |
| 1309 | H | CH₃ | CH₃ | H | H | 6-cyano-3-pyridazinyl |
| 1310 | H | CH₃ | CH₃ | H | H | 2-nitro-3-pyridazinyl |
| 1311 | H | CH₃ | CH₃ | H | H | 5-nitro-3-pyridazinyl |
| 1312 | H | CH₃ | CH₃ | H | H | 6-nitro-3-pyridazinyl |
| 1313 | H | CH₃ | CH₃ | H | H | 2-methanesulfonyl-3-pyridazinyl |
| 1314 | H | CH₃ | CH₃ | H | H | 5-methanesulfonyl-3-pyridazinyl |
| 1315 | H | CH₃ | CH₃ | H | H | 6-methanesulfonyl-3-pyridazinyl |
| 1316 | H | CH₃ | CH₃ | H | H | 2-pyrimidyl |
| 1317 | H | CH₃ | CH₃ | H | H | 4-fluoro-2-pyrimidyl |
| 1318 | H | CH₃ | CH₃ | H | H | 5-fluoro-2-pyrimidyl |
| 1319 | H | CH₃ | CH₃ | H | H | 4-chloro-2-pyrimidyl |
| 1320 | H | CH₃ | CH₃ | H | H | 5-chloro-2-pyrimidyl |
| 1321 | H | CH₃ | CH₃ | H | H | 4-bromo-2-pyrimidyl |
| 1322 | H | CH₃ | CH₃ | H | H | 5-bromo-2-pyrimidyl |
| 1323 | H | CH₃ | CH₃ | H | H | 4-methoxy-2-pyrimidyl |
| 1324 | H | CH₃ | CH₃ | H | H | 5-methoxy-2-pyrimidyl |
| 1325 | H | CH₃ | CH₃ | H | H | 4-trifluoromethoxy-2-pyrimidyl |
| 1326 | H | CH₃ | CH₃ | H | H | 5-trifluoromethoxy-2-pyrimidyl |
| 1327 | H | CH₃ | CH₃ | H | H | 4-methyl-2-pyrimidyl |
| 1328 | H | CH₃ | CH₃ | H | H | 5-methyl-2-pyrimidyl |
| 1329 | H | CH₃ | CH₃ | H | H | 4-trifluoromethyl-2-pyrimidyl |
| 1330 | H | CH₃ | CH₃ | H | H | 5-trifluoromethyl-2-pyrimidyl |
| 1331 | H | CH₃ | CH₃ | H | H | 4-cyano-2-pyrimidyl |
| 1332 | H | CH₃ | CH₃ | H | H | 5-cyano-2-pyrimidyl |
| 1333 | H | CH₃ | CH₃ | H | H | 4-nitro-2-pyrimidyl |
| 1334 | H | CH₃ | CH₃ | H | H | 5-nitro-2-pyrimidyl |
| 1335 | H | CH₃ | CH₃ | H | H | 4-methanesulfonyl-2-pyrimidyl |
| 1336 | H | CH₃ | CH₃ | H | H | 5-methanesulfonyl-2-pyrimidyl |
| 1337 | H | CH₃ | CH₃ | H | H | 4-pyrimidyl |
| 1338 | H | CH₃ | CH₃ | H | H | 2-fluoro-4-pyrimidyl |
| 1339 | H | CH₃ | CH₃ | H | H | 5-fluoro-4-pyrimidyl |
| 1340 | H | CH₃ | CH₃ | H | H | 6-fluoro-4-pyrimidyl |
| 1341 | H | CH₃ | CH₃ | H | H | 2-chloro-4-pyrimidyl |
| 1342 | H | CH₃ | CH₃ | H | H | 5-chloro-4-pyrimidyl |
| 1343 | H | CH₃ | CH₃ | H | H | 6-chloro-4-pyrimidyl |
| 1344 | H | CH₃ | CH₃ | H | H | 2-bromo-4-pyrimidyl |
| 1345 | H | CH₃ | CH₃ | H | H | 5-bromo-4-pyrimidyl |
| 1346 | H | CH₃ | CH₃ | H | H | 6-bromo-4-pyrimidyl |
| 1347 | H | CH₃ | CH₃ | H | H | 2-methoxy-4-pyrimidyl |
| 1348 | H | CH₃ | CH₃ | H | H | 5-methoxy-4-pyrimidyl |
| 1349 | H | CH₃ | CH₃ | H | H | 6-methoxy-4-pyrimidyl |
| 1350 | H | CH₃ | CH₃ | H | H | 2-trifluoromethoxy-4-pyrimidyl |
| 1351 | H | CH₃ | CH₃ | H | H | 5-trifluoromethoxy-4-pyrimidyl |
| 1352 | H | CH₃ | CH₃ | H | H | 6-trifluoromethoxy-4-pyrimidyl |
| 1353 | H | CH₃ | CH₃ | H | H | 2-methyl-4-pyrimidyl |
| 1354 | H | CH₃ | CH₃ | H | H | 5-methyl-4-pyrimidyl |
| 1355 | H | CH₃ | CH₃ | H | H | 6-methyl-4-pyrimidyl |
| 1356 | H | CH₃ | CH₃ | H | H | 2-trifluoromethyl-4-pyrimidyl |
| 1357 | H | CH₃ | CH₃ | H | H | 5-trifluoromethyl-4-pyrimidyl |
| 1358 | H | CH₃ | CH₃ | H | H | 6-trifluoromethyl-4-pyrimidyl |
| 1359 | H | CH₃ | CH₃ | H | H | 2-cyano-4-pyrimidyl |
| 1360 | H | CH₃ | CH₃ | H | H | 5-cyano-4-pyrimidyl |
| 1361 | H | CH₃ | CH₃ | H | H | 6-cyano-4-pyrimidyl |
| 1362 | H | CH₃ | CH₃ | H | H | 2-nitro-4-pyrimidyl |
| 1363 | H | CH₃ | CH₃ | H | H | 5-nitro-4-pyrimidyl |
| 1364 | H | CH₃ | CH₃ | H | H | 6-nitro-4-pyrimidyl |
| 1365 | H | CH₃ | CH₃ | H | H | 2-methanesulfonyl-4-pyrimidyl |
| 1366 | H | CH₃ | CH₃ | H | H | 5-methanesulfonyl-4-pyrimidyl |
| 1367 | H | CH₃ | CH₃ | H | H | 6-methanesulfonyl-4-pyrimidyl |
| 1368 | H | CH₃ | CH₃ | H | H | 5-pyrimidyl |

-continued

| Compound number | R⁵ | R⁶ | R⁷ | R⁸ | R⁹ | HetAr |
|---|---|---|---|---|---|---|
| 1369 | H | CH₃ | CH₃ | H | H | 2-fluoro-5-pyrimidyl |
| 1370 | H | CH₃ | CH₃ | H | H | 4-fluoro-5-pyrimidyl |
| 1371 | H | CH₃ | CH₃ | H | H | 2-chloro-5-pyrimidyl |
| 1372 | H | CH₃ | CH₃ | H | H | 4-chloro-5-pyrimidyl |
| 1373 | H | CH₃ | CH₃ | H | H | 2-bromo-5-pyrimidyl |
| 1374 | H | CH₃ | CH₃ | H | H | 4-bromo-5-pyrimidyl |
| 1375 | H | CH₃ | CH₃ | H | H | 2-methoxy-5-pyrimidyl |
| 1376 | H | CH₃ | CH₃ | H | H | 4-methoxy-5-pyrimidyl |
| 1377 | H | CH₃ | CH₃ | H | H | 2-trifluoromethoxy-5-pyrimidyl |
| 1378 | H | CH₃ | CH₃ | H | H | 4-trifluoromethoxy-5-pyrimidyl |
| 1379 | H | CH₃ | CH₃ | H | H | 2-methyl-5-pyrimidyl |
| 1380 | H | CH₃ | CH₃ | H | H | 4-methyl-5-pyrimidyl |
| 1381 | H | CH₃ | CH₃ | H | H | 2-trifluoromethyl-5-pyrimidyl |
| 1382 | H | CH₃ | CH₃ | H | H | 4-trifluoromethyl-5-pyrimidyl |
| 1383 | H | CH₃ | CH₃ | H | H | 2-cyano-5-pyrimidyl |
| 1384 | H | CH₃ | CH₃ | H | H | 4-cyano-5-pyrimidyl |
| 1385 | H | CH₃ | CH₃ | H | H | 2-nitro-5-pyrimidyl |
| 1386 | H | CH₃ | CH₃ | H | H | 4-nitro-5-pyrimidyl |
| 1387 | H | CH₃ | CH₃ | H | H | 2-methanesulfonyl-5-pyrimidyl |
| 1388 | H | CH₃ | CH₃ | H | H | 4-methanesulfonyl-5-pyrimidyl |
| 1389 | H | CH₃ | CH₃ | H | H | 2-pyrazinyl |
| 1390 | H | CH₃ | CH₃ | H | H | 3-fluoro-2-pyrazinyl |
| 1391 | H | CH₃ | CH₃ | H | H | 5-fluoro-2-pyrazinyl |
| 1392 | H | CH₃ | CH₃ | H | H | 6-fluoro-2-pyrazinyl |
| 1393 | H | CH₃ | CH₃ | H | H | 3-chloro-2-pyrazinyl |
| 1394 | H | CH₃ | CH₃ | H | H | 5-chloro-2-pyrazinyl |
| 1395 | H | CH₃ | CH₃ | H | H | 6-chloro-2-pyrazinyl |
| 1396 | H | CH₃ | CH₃ | H | H | 3-bromo-2-pyrazinyl |
| 1397 | H | CH₃ | CH₃ | H | H | 5-bromo-2-pyrazinyl |
| 1398 | H | CH₃ | CH₃ | H | H | 6-bromo-2-pyrazinyl |
| 1399 | H | CH₃ | CH₃ | H | H | 3-methoxy-2-pyrazinyl |
| 1400 | H | CH₃ | CH₃ | H | H | 5-methoxy-2-pyrazinyl |
| 1401 | H | CH₃ | CH₃ | H | H | 6-methoxy-2-pyrazinyl |
| 1402 | H | CH₃ | CH₃ | H | H | 3-trifluoromethoxy-2-pyrazinyl |
| 1403 | H | CH₃ | CH₃ | H | H | 5-trifluoromethoxy-2-pyrazinyl |
| 1404 | H | CH₃ | CH₃ | H | H | 6-trifluoromethoxy-2-pyrazinyl |
| 1405 | H | CH₃ | CH₃ | H | H | 3-methyl-2-pyrazinyl |
| 1406 | H | CH₃ | CH₃ | H | H | 5-methyl-2-pyrazinyl |
| 1407 | H | CH₃ | CH₃ | H | H | 6-methyl-2-pyrazinyl |
| 1408 | H | CH₃ | CH₃ | H | H | 3-trifluoromethyl-2-pyrazinyl |
| 1409 | H | CH₃ | CH₃ | H | H | 5-trifluoromethyl-2-pyrazinyl |
| 1410 | H | CH₃ | CH₃ | H | H | 6-trifluoromethyl-2-pyrazinyl |
| 1411 | H | CH₃ | CH₃ | H | H | 3-cyano-2-pyrazinyl |
| 1412 | H | CH₃ | CH₃ | H | H | 5-cyano-2-pyrazinyl |
| 1413 | H | CH₃ | CH₃ | H | H | 6-cyano-2-pyrazinyl |
| 1414 | H | CH₃ | CH₃ | H | H | 3-nitro-2-pyrazinyl |
| 1415 | H | CH₃ | CH₃ | H | H | 5-nitro-2-pyrazinyl |
| 1416 | H | CH₃ | CH₃ | H | H | 6-nitro-2-pyrazinyl |
| 1417 | H | CH₃ | CH₃ | H | H | 3-methylsulfonat-2-pyrazinyl |
| 1418 | H | CH₃ | CH₃ | H | H | 5-methylsulfonate-2-pyrazinyl |
| 1419 | H | CH₃ | CH₃ | H | H | 6-methylsulfonate-2-pyrazinyl |
| 1420 | H | CH₃ | CH₃ | H | H | 2-furanyl |
| 1421 | H | CH₃ | CH₃ | H | H | 3-fluoro-2-furanyl |
| 1422 | H | CH₃ | CH₃ | H | H | 4-fluoro-2-furanyl |
| 1423 | H | CH₃ | CH₃ | H | H | 5-fluoro-2-furanyl |
| 1424 | H | CH₃ | CH₃ | H | H | 3-chloro-2-furanyl |
| 1425 | H | CH₃ | CH₃ | H | H | 4-chloro-2-furanyl |
| 1426 | H | CH₃ | CH₃ | H | H | 5-chloro-2-furanyl |
| 1427 | H | CH₃ | CH₃ | H | H | 3-bromo-2-furanyl |
| 1428 | H | CH₃ | CH₃ | H | H | 4-bromo-2-furanyl |
| 1429 | H | CH₃ | CH₃ | H | H | 5-bromo-2-furanyl |
| 1430 | H | CH₃ | CH₃ | H | H | 3-methoxy-2-furanyl |
| 1431 | H | CH₃ | CH₃ | H | H | 4-methoxy-2-furanyl |
| 1432 | H | CH₃ | CH₃ | H | H | 5-methoxy-2-furanyl |
| 1433 | H | CH₃ | CH₃ | H | H | 3-trifluoromethoxy-2-furanyl |
| 1434 | H | CH₃ | CH₃ | H | H | 4-trifluoromethoxy-2-furanyl |
| 1435 | H | CH₃ | CH₃ | H | H | 5-trifluoromethoxy-2-furanyl |
| 1436 | H | CH₃ | CH₃ | H | H | 3-methyl-2-furanyl |
| 1437 | H | CH₃ | CH₃ | H | H | 4-methyl-2-furanyl |
| 1438 | H | CH₃ | CH₃ | H | H | 5-methyl-2-furanyl |
| 1439 | H | CH₃ | CH₃ | H | H | 3-trifluoromethyl-2-furanyl |
| 1440 | H | CH₃ | CH₃ | H | H | 4-trifluoromethyl-2-furanyl |
| 1441 | H | CH₃ | CH₃ | H | H | 5-trifluoromethyl-2-furanyl |
| 1442 | H | CH₃ | CH₃ | H | H | 3-cyano-2-furanyl |
| 1443 | H | CH₃ | CH₃ | H | H | 4-cyano-2-furanyl |
| 1444 | H | CH₃ | CH₃ | H | H | 5-cyano-2-furanyl |
| 1445 | H | CH₃ | CH₃ | H | H | 3-nitro-2-furanyl |
| 1446 | H | CH₃ | CH₃ | H | H | 4-nitro-2-furanyl |
| 1447 | H | CH₃ | CH₃ | H | H | 5-nitro-2-furanyl |
| 1448 | H | CH₃ | CH₃ | H | H | 3-methanesulfonyl-2-furanyl |
| 1449 | H | CH₃ | CH₃ | H | H | 4-methanesulfonyl-2-furanyl |
| 1450 | H | CH₃ | CH₃ | H | H | 5-methanesulfonyl-2-furanyl |
| 1451 | H | CH₃ | CH₃ | H | H | 3-furanyl |
| 1452 | H | CH₃ | CH₃ | H | H | 3-fluoro-2-furanyl |
| 1453 | H | CH₃ | CH₃ | H | H | 4-fluoro-2-furanyl |
| 1454 | H | CH₃ | CH₃ | H | H | 5-fluoro-2-furanyl |
| 1455 | H | CH₃ | CH₃ | H | H | 3-chloro-2-furanyl |
| 1456 | H | CH₃ | CH₃ | H | H | 4-chloro-2-furanyl |
| 1457 | H | CH₃ | CH₃ | H | H | 5-chloro-2-furanyl |
| 1458 | H | CH₃ | CH₃ | H | H | 3-bromo-2-furanyl |
| 1459 | H | CH₃ | CH₃ | H | H | 4-bromo-2-furanyl |
| 1460 | H | CH₃ | CH₃ | H | H | 5-bromo-2-furanyl |
| 1461 | H | CH₃ | CH₃ | H | H | 3-methoxy-2-furanyl |
| 1462 | H | CH₃ | CH₃ | H | H | 4-methoxy-2-furanyl |
| 1463 | H | CH₃ | CH₃ | H | H | 5-methoxy-2-furanyl |
| 1464 | H | CH₃ | CH₃ | H | H | 3-trifluoromethoxy-2-furanyl |
| 1465 | H | CH₃ | CH₃ | H | H | 4-trifluoromethoxy-2-furanyl |
| 1466 | H | CH₃ | CH₃ | H | H | 5-trifluoromethoxy-2-furanyl |
| 1467 | H | CH₃ | CH₃ | H | H | 3-methyl-2-furanyl |
| 1468 | H | CH₃ | CH₃ | H | H | 4-methyl-2-furanyl |
| 1469 | H | CH₃ | CH₃ | H | H | 5-methyl-2-furanyl |
| 1470 | H | CH₃ | CH₃ | H | H | 3-trifluoromethyl-2-furanyl |
| 1471 | H | CH₃ | CH₃ | H | H | 4-trifluoromethyl-2-furanyl |
| 1472 | H | CH₃ | CH₃ | H | H | 5-trifluoromethyl-2-furanyl |
| 1473 | H | CH₃ | CH₃ | H | H | 3-cyano-2-furanyl |
| 1474 | H | CH₃ | CH₃ | H | H | 4-cyano-2-furanyl |
| 1475 | H | CH₃ | CH₃ | H | H | 5-cyano-2-furanyl |
| 1476 | H | CH₃ | CH₃ | H | H | 3-nitro-2-furanyl |
| 1477 | H | CH₃ | CH₃ | H | H | 4-nitro-2-furanyl |
| 1478 | H | CH₃ | CH₃ | H | H | 5-nitro-2-furanyl |
| 1479 | H | CH₃ | CH₃ | H | H | 3-methanesulfonyl-2-furanyl |
| 1480 | H | CH₃ | CH₃ | H | H | 4-methanesulfonyl-2-furanyl |
| 1481 | H | CH₃ | CH₃ | H | H | 5-methanesufonyl-2-furanyl |
| 1482 | H | CH₃ | CH₃ | H | H | 3-furanyl |
| 1483 | H | CH₃ | CH₃ | H | H | 2-fluoro-3-furanyl |
| 1484 | H | CH₃ | CH₃ | H | H | 4-fluoro-3-furanyl |
| 1485 | H | CH₃ | CH₃ | H | H | 5-fluoro-3-furanyl |
| 1486 | H | CH₃ | CH₃ | H | H | 2-chloro-3-furanyl |
| 1487 | H | CH₃ | CH₃ | H | H | 4-chloro-3-furanyl |

-continued

| Compound number | R⁵ | R⁶ | R⁷ | R⁸ | R⁹ | HetAr |
|---|---|---|---|---|---|---|
| 1488 | H | CH₃ | CH₃ | H | H | 5-chloro-3-furanyl |
| 1489 | H | CH₃ | CH₃ | H | H | 2-bromo-3-furanyl |
| 1490 | H | CH₃ | CH₃ | H | H | 4-bromo-3-furanyl |
| 1491 | H | CH₃ | CH₃ | H | H | 5-bromo-3-furanyl |
| 1492 | H | CH₃ | CH₃ | H | H | 2-methoxy-3-furanyl |
| 1493 | H | CH₃ | CH₃ | H | H | 4-methoxy-3-furanyl |
| 1494 | H | CH₃ | CH₃ | H | H | 5-methoxy-3-furanyl |
| 1495 | H | CH₃ | CH₃ | H | H | 2-trifluoromethoxy-3-furanyl |
| 1496 | H | CH₃ | CH₃ | H | H | 4-trifluoromethoxy-3-furanyl |
| 1497 | H | CH₃ | CH₃ | H | H | 5-trifluoromethoxy-3-furanyl |
| 1498 | H | CH₃ | CH₃ | H | H | 2-methyl-3-furanyl |
| 1499 | H | CH₃ | CH₃ | H | H | 4-methyl-3-furanyl |
| 1500 | H | CH₃ | CH₃ | H | H | 5-methyl-3-furanyl |
| 1501 | H | CH₃ | CH₃ | H | H | 2-trifluoromethyl-3-furanyl |
| 1502 | H | CH₃ | CH₃ | H | H | 4-trifluoromethyl-3-furanyl |
| 1503 | H | CH₃ | CH₃ | H | H | 5-trifluoromethyl-3-furanyl |
| 1504 | H | CH₃ | CH₃ | H | H | 2-cyano-3-furanyl |
| 1505 | H | CH₃ | CH₃ | H | H | 4-cyano-3-furanyl |
| 1506 | H | CH₃ | CH₃ | H | H | 5-cyano-3-furanyl |
| 1507 | H | CH₃ | CH₃ | H | H | 2-nitro-3-furanyl |
| 1508 | H | CH₃ | CH₃ | H | H | 4-nitro-3-furanyl |
| 1509 | H | CH₃ | CH₃ | H | H | 5-nitro-3-furanyl |
| 1510 | H | CH₃ | CH₃ | H | H | 2-methanesulfonyl-3-furanyl |
| 1511 | H | CH₃ | CH₃ | H | H | 4-methanesulfonyl-3-furanyl |
| 1512 | H | CH₃ | CH₃ | H | H | 5-methanesufonyl-3-furanyl |
| 1513 | H | CH₃ | CH₃ | H | H | 2-thiophenyl |
| 1514 | H | CH₃ | CH₃ | H | H | 3-fluoro-2-thiophenyl |
| 1515 | H | CH₃ | CH₃ | H | H | 4-fluoro-2-thiophenyl |
| 1516 | H | CH₃ | CH₃ | H | H | 5-fluoro-2-thiophenyl |
| 1517 | H | CH₃ | CH₃ | H | H | 3-chloro-2-thiophenyl |
| 1518 | H | CH₃ | CH₃ | H | H | 4-chloro-2-thiophenyl |
| 1519 | H | CH₃ | CH₃ | H | H | 5-chloro-2-thiophenyl |
| 1520 | H | CH₃ | CH₃ | H | H | 3-bromo-2-thiophenyl |
| 1521 | H | CH₃ | CH₃ | H | H | 4-bromo-2-thiophenyl |
| 1522 | H | CH₃ | CH₃ | H | H | 5-bromo-2-thiophenyl |
| 1523 | H | CH₃ | CH₃ | H | H | 3-methoxy-2-thiophenyl |
| 1524 | H | CH₃ | CH₃ | H | H | 4-methoxy-2-thiophenyl |
| 1525 | H | CH₃ | CH₃ | H | H | 5-methoxy-2-thiophenyl |
| 1526 | H | CH₃ | CH₃ | H | H | 3-trifluoromethoxy-2-thiophenyl |
| 1527 | H | CH₃ | CH₃ | H | H | 4-trifluoromethoxy-2-thiophenyl |
| 1528 | H | CH₃ | CH₃ | H | H | 5-trifluoromethoxy-2-thiophenyl |
| 1529 | H | CH₃ | CH₃ | H | H | 3-methyl-2-thiophenyl |
| 1530 | H | CH₃ | CH₃ | H | H | 4-methyl-2-thiophenyl |
| 1531 | H | CH₃ | CH₃ | H | H | 5-methyl-2-thiophenyl |
| 1532 | H | CH₃ | CH₃ | H | H | 3-trifluoromethyl-2-thiophenyl |
| 1533 | H | CH₃ | CH₃ | H | H | 4-trifluoromethyl-2-thiophenyl |
| 1534 | H | CH₃ | CH₃ | H | H | 5-trifluoromethyl-2-thiophenyl |
| 1535 | H | CH₃ | CH₃ | H | H | 3-cyano-2-thiophenyl |
| 1536 | H | CH₃ | CH₃ | H | H | 4-cyano-2-thiophenyl |
| 1537 | H | CH₃ | CH₃ | H | H | 5-cyano-2-thiophenyl |
| 1538 | H | CH₃ | CH₃ | H | H | 3-nitro-2-thiophenyl |
| 1539 | H | CH₃ | CH₃ | H | H | 4-nitro-2-thiophenyl |
| 1540 | H | CH₃ | CH₃ | H | H | 5-nitro-2-thiophenyl |
| 1541 | H | CH₃ | CH₃ | H | H | 3-methanesulfonyl-2-thiophenyl |
| 1542 | H | CH₃ | CH₃ | H | H | 4-methanesulfonyl-2-thiophenyl |
| 1543 | H | CH₃ | CH₃ | H | H | 5-methanesufonyl-2-thiophenyl |
| 1544 | H | CH₃ | CH₃ | H | H | 3-thiophenyl |
| 1545 | H | CH₃ | CH₃ | H | H | 3-fluoro-2-thiophenyl |
| 1546 | H | CH₃ | CH₃ | H | H | 4-fluoro-2-thiophenyl |
| 1547 | H | CH₃ | CH₃ | H | H | 5-fluoro-2-thiophenyl |
| 1548 | H | CH₃ | CH₃ | H | H | 3-chloro-2-thiophenyl |
| 1549 | H | CH₃ | CH₃ | H | H | 4-chloro-2-thiophenyl |
| 1550 | H | CH₃ | CH₃ | H | H | 5-chloro-2-thiophenyl |
| 1551 | H | CH₃ | CH₃ | H | H | 3-bromo-2-thiophenyl |
| 1552 | H | CH₃ | CH₃ | H | H | 4-bromo-2-thiophenyl |
| 1553 | H | CH₃ | CH₃ | H | H | 5-bromo-2-thiophenyl |
| 1554 | H | CH₃ | CH₃ | H | H | 3-methoxy-2-thiophenyl |
| 1555 | H | CH₃ | CH₃ | H | H | 4-methoxy-2-thiophenyl |
| 1556 | H | CH₃ | CH₃ | H | H | 5-methoxy-2-thiophenyl |
| 1557 | H | CH₃ | CH₃ | H | H | 3-trifluoromethoxy-2-thiophenyl |
| 1558 | H | CH₃ | CH₃ | H | H | 4-trifluoromethoxy-2-thiophenyl |
| 1559 | H | CH₃ | CH₃ | H | H | 5-trifluoromethoxy-2-thiophenyl |
| 1560 | H | CH₃ | CH₃ | H | H | 3-methyl-2-thiophenyl |
| 1561 | H | CH₃ | CH₃ | H | H | 4-methyl-2-thiophenyl |
| 1562 | H | CH₃ | CH₃ | H | H | 5-methyl-2-thiophenyl |
| 1563 | H | CH₃ | CH₃ | H | H | 3-trifluoromethyl-2-thiophenyl |
| 1564 | H | CH₃ | CH₃ | H | H | 4-trifluoromethyl-2-thiophenyl |
| 1565 | H | CH₃ | CH₃ | H | H | 5-trifluoromethyl-2-thiophenyl |
| 1566 | H | CH₃ | CH₃ | H | H | 3-cyano-2-thiophenyl |
| 1567 | H | CH₃ | CH₃ | H | H | 4-cyano-2-thiophenyl |
| 1568 | H | CH₃ | CH₃ | H | H | 5-cyano-2-thiophenyl |
| 1569 | H | CH₃ | CH₃ | H | H | 3-nitro-2-thiophenyl |
| 1570 | H | CH₃ | CH₃ | H | H | 4-nitro-2-thiophenyl |
| 1571 | H | CH₃ | CH₃ | H | H | 5-nitro-2-thiophenyl |
| 1572 | H | CH₃ | CH₃ | H | H | 3-methanesulfonyl-2-thiophenyl |
| 1573 | H | CH₃ | CH₃ | H | H | 4-methanesulfonyl-2-thiophenyl |
| 1574 | H | CH₃ | CH₃ | H | H | 5-methanesulfonyl-2-thiophenyl |
| 1575 | H | CH₃ | CH₃ | H | H | 3-thiophenyl |
| 1576 | H | CH₃ | CH₃ | H | H | 2-fluoro-3-thiophenyl |
| 1577 | H | CH₃ | CH₃ | H | H | 4-fluoro-3-thiophenyl |
| 1578 | H | CH₃ | CH₃ | H | H | 5-fluoro-3-thiophenyl |
| 1579 | H | CH₃ | CH₃ | H | H | 2-chloro-3-thiophenyl |
| 1580 | H | CH₃ | CH₃ | H | H | 4-chloro-3-thiophenyl |
| 1581 | H | CH₃ | CH₃ | H | H | 5-chloro-3-thiophenyl |
| 1582 | H | CH₃ | CH₃ | H | H | 2-bromo-3-thiophenyl |
| 1583 | H | CH₃ | CH₃ | H | H | 4-bromo-3-thiophenyl |
| 1584 | H | CH₃ | CH₃ | H | H | 5-bromo-3-thiophenyl |
| 1585 | H | CH₃ | CH₃ | H | H | 2-methoxy-3-thiophenyl |
| 1586 | H | CH₃ | CH₃ | H | H | 4-methoxy-3-thiophenyl |
| 1587 | H | CH₃ | CH₃ | H | H | 5-methoxy-3-thiophenyl |
| 1588 | H | CH₃ | CH₃ | H | H | 2-trifluoromethoxy-3-thiophenyl |
| 1589 | H | CH₃ | CH₃ | H | H | 4-trifluoromethoxy-3-thiophenyl |
| 1590 | H | CH₃ | CH₃ | H | H | 5-trifluoromethoxy-3-thiophenyl |
| 1591 | H | CH₃ | CH₃ | H | H | 2-methyl-3-thiophenyl |
| 1592 | H | CH₃ | CH₃ | H | H | 4-methyl-3-thiophenyl |
| 1593 | H | CH₃ | CH₃ | H | H | 5-methyl-3-thiophenyl |
| 1594 | H | CH₃ | CH₃ | H | H | 2-trifluoromethyl-3-thiophenyl |
| 1595 | H | CH₃ | CH₃ | H | H | 4-trifluoromethyl-3-thiophenyl |
| 1596 | H | CH₃ | CH₃ | H | H | 5-trifluoromethyl-3-thiophenyl |
| 1597 | H | CH₃ | CH₃ | H | H | 2-cyano-3-thiophenyl |
| 1598 | H | CH₃ | CH₃ | H | H | 4-cyano-3-thiophenyl |
| 1599 | H | CH₃ | CH₃ | H | H | 5-cyano-3-thiophenyl |
| 1600 | H | CH₃ | CH₃ | H | H | 2-nitro-3-thiophenyl |
| 1601 | H | CH₃ | CH₃ | H | H | 4-nitro-3-thiophenyl |
| 1602 | H | CH₃ | CH₃ | H | H | 5-nitro-3-thiophenyl |
| 1603 | H | CH₃ | CH₃ | H | H | 2-methanesulfonyl-3-thiophenyl |
| 1604 | H | CH₃ | CH₃ | H | H | 4-methanesulfonyl-3-thiophenyl |

| Compound number | R⁵ | R⁶ | R⁷ | R⁸ | R⁹ | HetAr |
|---|---|---|---|---|---|---|
| 1605 | H | CH₃ | CH₃ | H | H | 5-methanesufonyl-3-thiophenyl |
| 1606 | H | CH₃ | CH₃ | H | H | 2-oxazole |
| 1607 | H | CH₃ | CH₃ | H | H | 4-fluoro-2-oxazole |
| 1608 | H | CH₃ | CH₃ | H | H | 5-fluoro-2-oxazole |
| 1609 | H | CH₃ | CH₃ | H | H | 4-chloro-2-oxazole |
| 1610 | H | CH₃ | CH₃ | H | H | 5-chloro-2-oxazole |
| 1611 | H | CH₃ | CH₃ | H | H | 4-bromo-2-oxazole |
| 1612 | H | CH₃ | CH₃ | H | H | 5-bromo-2-oxazole |
| 1613 | H | CH₃ | CH₃ | H | H | 4-methoxy-2-oxazole |
| 1614 | H | CH₃ | CH₃ | H | H | 5-methoxy-2-oxazole |
| 1615 | H | CH₃ | CH₃ | H | H | 4-trifluoromethoxy-2-oxazole |
| 1616 | H | CH₃ | CH₃ | H | H | 5-trifluoromethoxy-2-oxazole |
| 1617 | H | CH₃ | CH₃ | H | H | 4-methyl-2-oxazole |
| 1618 | H | CH₃ | CH₃ | H | H | 5-methyl-2-oxazole |
| 1619 | H | CH₃ | CH₃ | H | H | 4-trifluoromethyl-2-oxazole |
| 1620 | H | CH₃ | CH₃ | H | H | 5-trifluoromethyl-2-oxazole |
| 1621 | H | CH₃ | CH₃ | H | H | 4-cyano-2-oxazole |
| 1622 | H | CH₃ | CH₃ | H | H | 5-cyano-2-oxazole |
| 1623 | H | CH₃ | CH₃ | H | H | 4-nitro-2-oxazole |
| 1624 | H | CH₃ | CH₃ | H | H | 5-nitro-2-oxazole |
| 1625 | H | CH₃ | CH₃ | H | H | 4-methanesulfonyl-2-oxazole |
| 1626 | H | CH₃ | CH₃ | H | H | 5-methanesulfonyl-2-oxazole |
| 1627 | H | CH₃ | CH₃ | H | H | 4-oxazole |
| 1628 | H | CH₃ | CH₃ | H | H | 2-fluoro-4-oxazole |
| 1629 | H | CH₃ | CH₃ | H | H | 5-fluoro-4-oxazole |
| 1630 | H | CH₃ | CH₃ | H | H | 2-chloro-4-oxazole |
| 1631 | H | CH₃ | CH₃ | H | H | 5-chloro-4-oxazole |
| 1632 | H | CH₃ | CH₃ | H | H | 2-bromo-4-oxazole |
| 1633 | H | CH₃ | CH₃ | H | H | 5-bromo-4-oxazole |
| 1634 | H | CH₃ | CH₃ | H | H | 2-methoxy-4-oxazole |
| 1635 | H | CH₃ | CH₃ | H | H | 5-methoxy-4-oxazole |
| 1636 | H | CH₃ | CH₃ | H | H | 2-trifluoromethoxy-4-oxazole |
| 1637 | H | CH₃ | CH₃ | H | H | 5-trifluoromethoxy-4-oxazole |
| 1638 | H | CH₃ | CH₃ | H | H | 2-methyl-4-oxazole |
| 1639 | H | CH₃ | CH₃ | H | H | 5-methyl-4-oxazole |
| 1640 | H | CH₃ | CH₃ | H | H | 4-trifluoromethyl-4-oxazole |
| 1641 | H | CH₃ | CH₃ | H | H | 5-trifluoromethyl-4-oxazole |
| 1642 | H | CH₃ | CH₃ | H | H | 4-cyano-4-oxazole |
| 1643 | H | CH₃ | CH₃ | H | H | 5-cyano-4-oxazole |
| 1644 | H | CH₃ | CH₃ | H | H | 4-nitro-4-oxazole |
| 1645 | H | CH₃ | CH₃ | H | H | 5-nitro-4-oxazole |
| 1646 | H | CH₃ | CH₃ | H | H | 4-methanesulfonyl-4-oxazole |
| 1647 | H | CH₃ | CH₃ | H | H | 5-methanesulfonyl-4-oxazole |
| 1648 | H | CH₃ | CH₃ | H | H | 5-oxazole |
| 1649 | H | CH₃ | CH₃ | H | H | 2-fluoro-5-oxazole |
| 1650 | H | CH₃ | CH₃ | H | H | 4-fluoro-5-oxazole |
| 1651 | H | CH₃ | CH₃ | H | H | 2-chloro-5-oxazole |
| 1652 | H | CH₃ | CH₃ | H | H | 4-chloro-5-oxazole |
| 1653 | H | CH₃ | CH₃ | H | H | 2-bromo-5-oxazole |
| 1654 | H | CH₃ | CH₃ | H | H | 4-bromo-5-oxazole |
| 1655 | H | CH₃ | CH₃ | H | H | 2-methoxy-5-oxazole |
| 1656 | H | CH₃ | CH₃ | H | H | 4-methoxy-5-oxazole |
| 1657 | H | CH₃ | CH₃ | H | H | 2-trifluoromethoxy-5-oxazole |
| 1658 | H | CH₃ | CH₃ | H | H | 4-trifluoromethoxy-5-oxazole |
| 1659 | H | CH₃ | CH₃ | H | H | 2-methyl-5-oxazole |
| 1660 | H | CH₃ | CH₃ | H | H | 4-methyl-5-oxazole |
| 1661 | H | CH₃ | CH₃ | H | H | 2-trifluoromethyl-5-oxazole |
| 1662 | H | CH₃ | CH₃ | H | H | 4-trifluoromethyl-5-oxazole |
| 1663 | H | CH₃ | CH₃ | H | H | 2-cyano-5-oxazole |
| 1664 | H | CH₃ | CH₃ | H | H | 4-cyano-5-oxazole |
| 1665 | H | CH₃ | CH₃ | H | H | 2-nitro-5-oxazole |
| 1666 | H | CH₃ | CH₃ | H | H | 4-nitro-5-oxazole |
| 1667 | H | CH₃ | CH₃ | H | H | 2-methanesulfonyl-5-oxazole |
| 1668 | H | CH₃ | CH₃ | H | H | 4-methanesulfonyl-5-oxazole |
| 1669 | H | CH₃ | CH₃ | H | H | 2-thiazole |
| 1670 | H | CH₃ | CH₃ | H | H | 4-fluoro-2-thiazole |
| 1671 | H | CH₃ | CH₃ | H | H | 5-fluoro-2-thiazole |
| 1672 | H | CH₃ | CH₃ | H | H | 4-chloro-2-thiazole |
| 1673 | H | CH₃ | CH₃ | H | H | 5-chloro-2-thiazole |
| 1674 | H | CH₃ | CH₃ | H | H | 4-bromo-2-thiazole |
| 1675 | H | CH₃ | CH₃ | H | H | 5-bromo-2-thiazole |
| 1676 | H | CH₃ | CH₃ | H | H | 4-methoxy-2-thiazole |
| 1677 | H | CH₃ | CH₃ | H | H | 5-methoxy-2-thiazole |
| 1678 | H | CH₃ | CH₃ | H | H | 4-trifluoromethoxy-2-thiazole |
| 1679 | H | CH₃ | CH₃ | H | H | 5-trifluoromethoxy-2-thiazole |
| 1680 | H | CH₃ | CH₃ | H | H | 4-methyl-2-thiazole |
| 1681 | H | CH₃ | CH₃ | H | H | 5-methyl-2-thiazole |
| 1682 | H | CH₃ | CH₃ | H | H | 4-trifluoromethyl-2-thiazole |
| 1683 | H | CH₃ | CH₃ | H | H | 5-trifluoromethyl-2-thiazole |
| 1684 | H | CH₃ | CH₃ | H | H | 4-cyano-2-thiazole |
| 1685 | H | CH₃ | CH₃ | H | H | 5-cyano-2-thiazole |
| 1686 | H | CH₃ | CH₃ | H | H | 4-nitro-2-thiazole |
| 1687 | H | CH₃ | CH₃ | H | H | 5-nitro-2-thiazole |
| 1688 | H | CH₃ | CH₃ | H | H | 4-methanesulfonyl-2-thiazole |
| 1689 | H | CH₃ | CH₃ | H | H | 5-methanesulfonyl-2-thiazole |
| 1690 | H | CH₃ | CH₃ | H | H | 4-thiazole |
| 1691 | H | CH₃ | CH₃ | H | H | 2-fluoro-4-thiazole |
| 1692 | H | CH₃ | CH₃ | H | H | 5-fluoro-4-thiazole |
| 1693 | H | CH₃ | CH₃ | H | H | 2-chloro-4-thiazole |
| 1694 | H | CH₃ | CH₃ | H | H | 5-chloro-4-thiazole |
| 1695 | H | CH₃ | CH₃ | H | H | 2-bromo-4-thiazole |
| 1696 | H | CH₃ | CH₃ | H | H | 5-bromo-4-thiazole |
| 1697 | H | CH₃ | CH₃ | H | H | 2-methoxy-4-thiazole |
| 1698 | H | CH₃ | CH₃ | H | H | 5-methoxy-4-thiazole |
| 1699 | H | CH₃ | CH₃ | H | H | 2-trifluoromethoxy-4-thiazole |
| 1700 | H | CH₃ | CH₃ | H | H | 5-trifluoromethoxy-4-thiazole |
| 1701 | H | CH₃ | CH₃ | H | H | 2-methyl-4-thiazole |
| 1702 | H | CH₃ | CH₃ | H | H | 5-methyl-4-thiazole |
| 1703 | H | CH₃ | CH₃ | H | H | 4-trifluoromethyl-4-thiazole |
| 1704 | H | CH₃ | CH₃ | H | H | 5-trifluoromethyl-4-thiazole |
| 1705 | H | CH₃ | CH₃ | H | H | 4-cyano-4-thiazole |
| 1706 | H | CH₃ | CH₃ | H | H | 5-cyano-4-thiazole |
| 1707 | H | CH₃ | CH₃ | H | H | 4-nitro-4-thiazole |
| 1708 | H | CH₃ | CH₃ | H | H | 5-nitro-4-thiazole |
| 1709 | H | CH₃ | CH₃ | H | H | 4-methanesulfonyl-4-thiazole |
| 1710 | H | CH₃ | CH₃ | H | H | 5-methanesulfonyl-4-thiazole |
| 1711 | H | CH₃ | CH₃ | H | H | 5-thiazole |
| 1712 | H | CH₃ | CH₃ | H | H | 2-fluoro-5-thiazole |
| 1713 | H | CH₃ | CH₃ | H | H | 4-fluoro-5-thiazole |
| 1714 | H | CH₃ | CH₃ | H | H | 2-chloro-5-thiazole |
| 1715 | H | CH₃ | CH₃ | H | H | 4-chloro-5-thiazole |
| 1716 | H | CH₃ | CH₃ | H | H | 2-bromo-5-thiazole |
| 1717 | H | CH₃ | CH₃ | H | H | 4-bromo-5-thiazole |
| 1718 | H | CH₃ | CH₃ | H | H | 2-methoxy-5-thiazole |
| 1719 | H | CH₃ | CH₃ | H | H | 4-methoxy-5-thiazole |
| 1720 | H | CH₃ | CH₃ | H | H | 2-trifluoromethoxy-5-thiazole |
| 1721 | H | CH₃ | CH₃ | H | H | 4-trifluoromethoxy-5-thiazole |
| 1722 | H | CH₃ | CH₃ | H | H | 2-methyl-5-thiazole |
| 1723 | H | CH₃ | CH₃ | H | H | 4-methyl-5-thiazole |

| Compound number | $R^5$ | $R^6$ | $R^7$ | $R^8$ | $R^9$ | HetAr |
|---|---|---|---|---|---|---|
| 1724 | H | CH$_3$ | CH$_3$ | H | H | 2-trifluoromethyl-5-thiazole |
| 1725 | H | CH$_3$ | CH$_3$ | H | H | 4-trifluoromethyl-5-thiazole |
| 1726 | H | CH$_3$ | CH$_3$ | H | H | 2-cyano-5-thiazole |
| 1727 | H | CH$_3$ | CH$_3$ | H | H | 4-cyano-5-thiazole |
| 1728 | H | CH$_3$ | CH$_3$ | H | H | 2-nitro-5-thiazole |
| 1729 | H | CH$_3$ | CH$_3$ | H | H | 4-nitro-5-thiazole |
| 1730 | H | CH$_3$ | CH$_3$ | H | H | 2-methanesulfonyl-5-thiazole |
| 1731 | H | CH$_3$ | CH$_3$ | H | H | 4-methanesulfonyl-5-thiazole |

Table 2 covers 1731 compounds of the structural type T-1, wherein $R^1$, $R^2$ and $R^4$ are methyl and $R^3$ is hydrogen and $R^5$, $R^6$, $R^7$, $R^8$, $R^9$ and HetAr are as defined in Table 1.

Table 3 covers 1731 compounds of the structural type T-1, wherein $R^1$ and $R^4$ are methyl and $R^2$ is chloride and $R^3$ is hydrogen and $R^5$, $R^6$, $R^7$, $R^8$, $R^9$ and HetAr are as defined in Table 1.

Table 4 covers 1731 compounds of the structural type T-1, wherein $R^1$ and $R^4$ are methyl and $R^2$ is chloride and $R^3$ is hydrogen and $R^5$, $R^6$, $R^7$, $R^8$, $R^9$ and HetAr are as defined in Table 1.

Table 5 covers 1731 compounds of the structural type T-1, wherein $R^1$ and $R^2$ are methyl and $R^4$ is chloride and $R^3$ is hydrogen and $R^5$, $R^6$, $R^7$, $R^8$, $R^9$ and HetAr are as defined in Table 1.

Table 6 covers 1731 compounds of the structural type T-1, wherein $R^1$ and $R^4$ are methyl and $R^2$ is bromide and $R^3$ is hydrogen and $R^5$, $R^6$, $R^7$, $R^8$, $R^9$ and HetAr are as defined in Table 1.

Table 7 covers 1731 compounds of the structural type T-1, wherein $R^1$ and $R^4$ are methyl, $R^2$ is bromide, $R^3$ is hydrogen and $R^5$, $R^6$, $R^7$, $R^8$, $R^9$ and HetAr are as defined in Table 1.

Table 8 covers 1731 compounds of the structural type T-1, wherein $R^1$ is methyl, $R^2$ is chloride, $R^3$ is hydrogen, $R^4$ is methoxy and $R^5$, $R^6$, $R^7$, $R^8$, $R^9$ and HetAr are as defined in Table 1.

Table 9 covers 1731 compounds of the structural type T-1, wherein $R^1$ is methyl, $R^2$ is bromide, $R^3$ is hydrogen, $R^4$ is methoxy and $R^5$, $R^6$, $R^7$, $R^8$, $R^9$ and HetAr are as defined in Table 1.

Table 10 covers 1731 compounds of the structural type T-1, wherein $R^1$ and $R^2$ are methyl, $R^4$ is ethenyl, $R^3$ is hydrogen and $R^5$, $R^6$, $R^7$, $R^8$, $R^9$ and HetAr are as defined in Table 1.

Table 11 covers 1731 compounds of the structural type T-1, wherein $R^1$ and $R^4$ are methyl, $R^2$ is ethynyl, $R^3$ is hydrogen and $R^5$, $R^6$, $R^7$, $R^8$, $R^9$ and HetAr are as defined in Table 1.

Table 12 covers 1731 compounds of the structural type T-1, wherein $R^1$ and $R^2$ are methyl, $R^4$ is ethynyl, $R^3$ is hydrogen and $R^5$, $R^6$, $R^7$, $R^8$, $R^9$ and HetAr are as defined in Table 1.

Table 13 covers 1731 compounds of the structural type T-1, wherein $R^1$ and $R^4$ are methyl, $R^2$ is phenyl, $R^3$ is hydrogen and $R^5$, $R^6$, $R^7$, $R^8$, $R^9$ and HetAr are as defined in Table 1.

Table 14 covers 1731 compounds of the structural type T-1, wherein $R^1$ and $R^4$ are methyl, $R^2$ is 3-fluoro-phenyl, $R^3$ is hydrogen and $R^5$, $R^6$, $R^7$, $R^8$, $R^9$ and HetAr are as defined in Table 1.

Table 15 covers 1731 compounds of the structural type T-1, wherein $R^1$ and $R^4$ are methyl, $R^2$ is 3-chloro-phenyl, $R^3$ is hydrogen and $R^5$, $R^6$, $R^7$, $R^8$, $R^9$ and HetAr are as defined in Table 1.

Table 16 covers 1731 compounds of the structural type T-1, wherein $R^1$ and $R^4$ are methyl, $R^2$ is 3-trifluoro-phenyl, $R^3$ is hydrogen and $R^5$, $R^6$, $R^7$, $R^8$, $R^9$ and HetAr are as defined in Table 1.

Table 17 covers 1731 compounds of the structural type T-1, wherein $R^1$ and $R^4$ are methyl, $R^2$ is 4-fluoro-phenyl, $R^3$ is hydrogen and $R^5$, $R^6$, $R^7$, $R^8$, $R^9$ and HetAr are as defined in Table 1.

Table 18 covers 1731 compounds of the structural type T-1, wherein $R^1$ and $R^4$ are methyl, $R^2$ is 4-chloro-phenyl, $R^3$ is hydrogen and $R^5$, $R^6$, $R^7$, $R^8$, $R^9$ and HetAr are as defined in Table 1.

Table 19 covers 1731 compounds of the structural type T-1, wherein $R^1$ and $R^4$ are methyl, $R^2$ is 4-trifluoro-phenyl, $R^3$ is hydrogen and $R^5$, $R^6$, $R^7$, $R^8$, $R^9$ and HetAr are as defined in Table 1.

Table 20 covers 1731 compounds of the structural type T-1, wherein $R^1$ and $R^4$ are methyl, $R^2$ is 3,4-difluoro-phenyl, $R^3$ is hydrogen and $R^5$, $R^6$, $R^7$, $R^8$, $R^9$ and HetAr are as defined in Table 1.

Table 21 covers 1731 compounds of the structural type T-1, wherein $R^1$ and $R^4$ are methyl, $R^2$ is 3-fluoro-4-chloro-phenyl, $R^3$ is hydrogen and $R^5$, $R^6$, $R^7$, $R^8$, $R^9$ and HetAr are as defined in Table 1.

Table 22 covers 1731 compounds of the structural type T-1, wherein $R^1$ and $R^4$ are methyl, $R^2$ is 3-chloro-4-fluoro-phenyl, $R^3$ is hydrogen and $R^5$, $R^6$, $R^7$, $R^8$, $R^9$ and HetAr are as defined in Table 1.

Table 23 covers 1731 compounds of the structural type T-1, wherein $R^1$ and $R^4$ are methyl, $R^2$ is 3,4-dichloro-phenyl, $R^3$ is hydrogen and $R^5$, $R^6$, $R^7$, $R^8$, $R^9$ and HetAr are as defined in Table 1.

Table 24 covers 1731 compounds of the structural type T-1, wherein $R^1$ is methyl, $R^2$ and $R^4$ are hydrogen and $R^3$ is 4-chloro-phenyl and $R^5$, $R^6$, $R^7$, $R^8$, $R^9$ and HetAr are as defined in Table 1.

Table 25 covers 1731 compounds of the structural type T-1, wherein $R^1$ is methyl, $R^2$ and $R^4$ are hydrogen and $R^3$ is 4-bromo-phenyl and $R^5$, $R^6$, $R^7$, $R^8$, $R^9$ and HetAr are as defined in Table 1.

Table 26 covers 1731 compounds of the structural type T-1, wherein $R^1$ is methyl, $R^2$ and $R^4$ are hydrogen and $R^3$ is 4-difluoromethoxy-phenyl and $R^5$, $R^6$, $R^7$, $R^8$, $R^9$ and HetAr are as defined in Table 1.

Table 27 covers 1731 compounds of the structural type T-1, wherein $R^1$ is methyl, $R^2$ and $R^4$ are hydrogen and $R^3$ is 2-fluoro-4-chloro-phenyl and $R^5$, $R^6$, $R^7$, $R^8$, $R^9$ and HetAr are as defined in Table 1.

Table 28 covers 1731 compounds of the structural type T-1, wherein $R^1$ is methyl, $R^2$ and $R^4$ are hydrogen and $R^3$ is 2,4-dichloro-phenyl and $R^5$, $R^6$, $R^7$, $R^8$, $R^9$ and HetAr are as defined in Table 1.

Table 29 covers 1731 compounds of the structural type T-1, wherein $R^1$ is methyl, $R^2$ and $R^4$ are hydrogen and $R^3$ is 2-methyl-4-dichloro-phenyl and $R^5$, $R^6$, $R^7$, $R^8$, $R^9$ and HetAr are as defined in Table 1.

Table 30 covers 1731 compounds of the structural type T-1, wherein $R^1$ is ethyl, $R^2$ and $R^4$ are methyl and $R^3$ is hydrogen and $R^5$, $R^6$, $R^7$, $R^8$, $R^9$ and HetAr are as defined in Table 1.

Table 31 covers 1731 compounds of the structural type T-1, wherein $R^1$ is ethyl, $R^4$ is methyl and $R^2$ is chloride and $R^3$ is hydrogen and $R^5$, $R^6$, $R^7$, $R^8$, $R^9$ and HetAr are as defined in Table 1.

Table 32 covers 1731 compounds of the structural type T-1, wherein $R^1$ is ethyl, $R^4$ is methyl and $R^2$ is chloride and $R^3$ is hydrogen and $R^5$, $R^6$, $R^7$, $R^8$, $R^9$ and HetAr are as defined in Table 1.

Table 33 covers 1731 compounds of the structural type T-1, wherein $R^1$ is ethyl, $R^2$ is methyl and $R^4$ is chloride and $R^3$ is hydrogen and $R^5$, $R^6$, $R^7$, $R^8$, $R^9$ and HetAr are as defined in Table 1.

Table 34 covers 1731 compounds of the structural type T-1, wherein $R^1$ is ethyl $R^4$ is methyl and $R^2$ is bromide and $R^3$ is hydrogen and $R^5$, $R^6$, $R^7$, $R^8$, $R^9$ and HetAr are as defined in Table 1.

Table 35 covers 1731 compounds of the structural type T-1, wherein $R^1$ is ethyl, $R^4$ is methyl, $R^2$ is bromide, $R^3$ is hydrogen and $R^5$, $R^6$, $R^7$, $R^8$, $R^9$ and HetAr are as defined in Table 1.

Table 36 covers 1731 compounds of the structural type T-1, wherein $R^1$ is ethyl, $R^2$ is chloride, $R^3$ is hydrogen, $R^4$ is methoxy and $R^5$, $R^6$, $R^7$, $R^8$, $R^9$ and HetAr are as defined in Table 1.

Table 37 covers 1731 compounds of the structural type T-1, wherein $R^1$ is ethyl, $R^2$ is bromide, $R^3$ is hydrogen, $R^4$ is methoxy and $R^5$, $R^6$, $R^7$, $R^8$, $R^9$ and HetAr are as defined in Table 1.

Table 38 covers 1731 compounds of the structural type T-1, wherein $R^1$ is ethyl, $R^2$ is methyl, $R^4$ is ethenyl, $R^3$ is hydrogen and $R^5$, $R^6$, $R^7$, $R^8$, $R^9$ and HetAr are as defined in Table 1.

Table 39 covers 1731 compounds of the structural type T-1, wherein $R^1$ is ethyl, $R^4$ are methyl, $R^2$ is ethynyl, $R^3$ is hydrogen and $R^5$, $R^6$, $R^7$, $R^8$, $R^9$ and HetAr are as defined in Table 1.

Table 40 covers 1731 compounds of the structural type T-1, wherein $R^1$ is ethyl, $R^2$ is methyl, $R^4$ is ethynyl, $R^3$ is hydrogen and $R^5$, $R^6$, $R^7$, $R^8$, $R^9$ and HetAr are as defined in Table 1.

Table 41 covers 1731 compounds of the structural type T-1, wherein $R^1$ is ethyl, $R^4$ is methyl, $R^2$ is phenyl, $R^3$ is hydrogen and $R^5$, $R^6$, $R^7$, $R^8$, $R^9$ and HetAr are as defined in Table 1.

Table 42 covers 1731 compounds of the structural type T-1, wherein $R^1$ is ethyl, $R^4$ is methyl, $R^2$ is 3-fluoro-phenyl, $R^3$ is hydrogen and $R^5$, $R^6$, $R^7$, $R^8$, $R^9$ and HetAr are as defined in Table 1.

Table 43 covers 1731 compounds of the structural type T-1, wherein $R^1$ is ethyl, $R^4$ is methyl, $R^2$ is 3-chloro-phenyl, $R^3$ is hydrogen and $R^5$, $R^6$, $R^7$, $R^8$, $R^9$ and HetAr are as defined in Table 1.

Table 44 covers 1731 compounds of the structural type T-1, wherein $R^1$ is ethyl, $R^4$ is methyl, $R^2$ is 3-trifluoro-phenyl, $R^3$ is hydrogen and $R^5$, $R^6$, $R^7$, $R^8$, $R^9$ and HetAr are as defined in Table 1.

Table 45 covers 1731 compounds of the structural type T-1, wherein $R^1$ is ethyl, $R^4$ is methyl, $R^2$ is 4-fluoro-phenyl, $R^3$ is hydrogen and $R^5$, $R^6$, $R^7$, $R^8$, $R^9$ and HetAr are as defined in Table 1.

Table 46 covers 1731 compounds of the structural type T-1, wherein $R^1$ is ethyl, $R^4$ is methyl, $R^2$ is 4-chloro-phenyl, $R^3$ is hydrogen and $R^5$, $R^6$, $R^7$, $R^8$, $R^9$ and HetAr are as defined in Table 1.

Table 47 covers 1731 compounds of the structural type T-1, wherein $R^1$ is ethyl, $R^4$ is methyl, $R^2$ is 4-trifluoro-phenyl, $R^3$ is hydrogen and $R^5$, $R^6$, $R^7$, $R^8$, $R^9$ and HetAr are as defined in Table 1.

Table 48 covers 1731 compounds of the structural type T-1, wherein $R^1$ is ethyl, $R^4$ is methyl, $R^2$ is 3,4-difluoro-phenyl, $R^3$ is hydrogen and $R^5$, $R^6$, $R^7$, $R^8$, $R^9$ and HetAr are as defined in Table 1.

Table 49 covers 1731 compounds of the structural type T-1, wherein $R^1$ is ethyl, $R^4$ is methyl, $R^2$ is 3-fluoro-4-chloro-phenyl, $R^3$ is hydrogen and $R^5$, $R^6$, $R^7$, $R^8$, $R^9$ and HetAr are as defined in Table 1.

Table 50 covers 1731 compounds of the structural type T-1, wherein $R^1$ is ethyl, $R^4$ is methyl, $R^2$ is 3-chloro-4-fluoro-phenyl, $R^3$ is hydrogen and $R^5$, $R^6$, $R^7$, $R^8$, $R^9$ and HetAr are as defined in Table 1.

Table 51 covers 1731 compounds of the structural type T-1, wherein $R^1$ is ethyl, $R^4$ is methyl, $R^2$ is 3,4-dichloro-phenyl, $R^3$ is hydrogen and $R^5$, $R^6$, $R^7$, $R^8$, $R^9$ and HetAr are as defined in Table 1.

Table 52 covers 1731 compounds of the structural type T-1, wherein $R^1$ is ethyl, $R^2$ and $R^4$ are hydrogen and $R^3$ is 4-chloro-phenyl and $R^5$, $R^6$, $R^7$, $R^8$, $R^9$ and HetAr are as defined in Table 1.

Table 53 covers 1731 compounds of the structural type T-1, wherein $R^1$ is ethyl, $R^2$ and $R^4$ are hydrogen and $R^3$ is 4-bromo-phenyl and $R^5$, $R^6$, $R^7$, $R^8$, $R^9$ and HetAr are as defined in Table 1.

Table 54 covers 1731 compounds of the structural type T-1, wherein $R^1$ is ethyl, $R^2$ and $R^4$ are hydrogen and $R^3$ is 4-difluoromethoxy-phenyl and $R^5$, $R^6$, $R^7$, $R^8$, $R^9$ and HetAr are as defined in Table 1.

Table 55 covers 1731 compounds of the structural type T-1, wherein $R^1$ is ethyl, $R^2$ and $R^4$ are hydrogen and $R^3$ is 2-fluoro-4-chloro-phenyl and $R^5$, $R^6$, $R^7$, $R^8$, $R^9$ and HetAr are as defined in Table 1.

Table 56 covers 1731 compounds of the structural type T-1, wherein $R^1$ is ethyl, $R^2$ and $R^4$ are hydrogen and $R^3$ is 2,4-dichloro-phenyl and $R^5$, $R^6$, $R^7$, $R^8$, $R^9$ and HetAr are as defined in Table 1.

Table 57 covers 1731 compounds of the structural type T-1, wherein $R^1$ is ethyl, $R^2$ and $R^4$ are hydrogen and $R^3$ is 2-methyl-4-dichloro-phenyl and $R^5$, $R^6$, $R^7$, $R^8$, $R^9$ and HetAr are as defined in Table 1.

Table 58 covers 1731 compounds of the structural type T-1, wherein $R^1$ and $R^4$ is ethyl, $R^2$ is methyl and $R^3$ is hydrogen $R^5$, $R^6$, $R^7$, $R^8$, $R^9$ and HetAr are as defined in Table 1.

BIOLOGICAL EXAMPLES

Seeds of a variety of test species are sown in standard soil in pots. After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants are then grown in a glasshouse under controlled conditions in a glasshouse (at 24/16° C., day/night; 14 hours light; 65% humidity) and watered twice daily. After 13 days for pre and post-emergence, the test is evaluated (100=total damage to plant; 0=no damage to plant).

Test plants:
*Lolium perenne* (LOLPE), *Alopecurus myosuroides* (ALOMY), *Echinochloa crus-galli* (ECHCG), *Avena fatua* (AVEFA)

| | Post-Emergence Activity | | | | |
|---|---|---|---|---|---|
| Compound Number | Rate g/ha | LOLPE | ALOMY | ECHCG | AVEFA |
| T2 | 250 | 80 | 60 | 80 | 20 |
| T3 | 250 | 90 | 90 | 80 | 80 |
| T4 | 250 | 50 | 40 | 30 | 20 |
| T8 | 250 | 30 | 10 | 30 | 0 |

| Pre-Emergence Activity | | | | | |
|---|---|---|---|---|---|
| Compound Number | Rate g/ha | LOLPE | ALOMY | ECHCG | AVEFA |
| T2 | 250 | 80 | 30 | 0 | 20 |
| T3 | 250 | 100 | 100 | 80 | 70 |
| P1 | 250 | 40 | 0 | 0 | 0 |
| P2 | 250 | 90 | 0 | 0 | 0 |

What is claimed is:

1. A compound of formula I

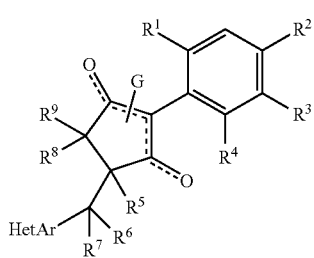

(I)

wherein

G is hydrogen or an agriculturally acceptable metal, sulfonium, ammonium or latentiating group;

$R^1$ is methyl, ethyl, n-propyl, isopropyl, cyclopropyl, halomethyl, haloethyl, vinyl, ethynyl, halogen, $C_1$-$C_2$alkoxy or $C_1$-$C_2$haloalkoxy;

$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, $C_1$-$C_2$alkoxy, $C_1$-$C_2$haloalkoxy, optionally substituted aryl or optionally substituted heteroaryl;

and wherein, in $R^2$ and $R^3$, when present, the optional substituents on aryl and heteroaryl are selected, independently, from: halogen, nitro, cyano, rhodano, isothiocyanato, $C_1$-$C_6$alkyl, $C_1$-$C_6$haloalkyl, $C_1$-$C_6$alkoxy($C_1$-$C_6$) alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, or arylcarbonyl (where the aryl group is itself optionally substituted with halogen or $C_1$-$C_6$alkyl); or two adjacent positions on an aryl or heteroaryl system are cyclised to form a 5, 6 or 7 membered carbocyclic or heterocyclic ring, itself optionally substituted with halogen or $C_1$-$C_6$alkyl;

$R^4$ is hydrogen, methyl, ethyl, n-propyl, isopropyl, cyclopropyl, halomethyl, haloethyl, vinyl, propenyl, ethynyl, propynyl, halogen, $C_1$-$C_2$alkoxy or $C_1$-$C_2$haloalkoxy; and $R^5$, $R^6$, $R^7$, $R^8$ and $R^9$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl; or $R^6$ and $R^7$ or $R^8$ and $R^9$ together with the carbon atoms to which they are attached form an optionally substituted carbocyclic ring, or a heterocyclyl optionally substituted by $C_1$-$C_6$alkyl or $C_1$-$C_6$haloalkyl;

wherein a "carbocyclic ring" means a cycloalkyl or cycloalkenyl group; and wherein, when present, the optional substituents on cycloalkyl or cycloalkenyl are $C_1$-$C_3$alkyl; or $R^5$ and $R^6$ together form a bond; and HetAr is an heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;

and wherein when G is a latentiating group then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;

wherein $X^a$, $X^b$, $X^c$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$ alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$ cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$ alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ may loin together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$ alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$ alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; and wherein "aryl" means phenyl;

wherein "heteroaryl" means fury, thienyl, pyrrolyl, pyrazolyl, imidazolyl, 1,2,3-triazolyl, 1 ,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2, 5-thiadiazolyl, pyridly, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; and wherein "heterocyclyl" means 1,3-dioxolane, oxetane, tetrahydrofuran, morpholine, thiomorpholine or piperazine.

2. A compound according to claim 1, wherein $R^1$ is methyl, ethyl, n-propyl, vinyl, ethynyl, halogen, $C_1$-$C_2$alkoxy or $C_1$-$C_2$haloalkoxy;

$R^2$ is methyl, halogen, $C_1$-$C_2$alkoxy or $C_1$-$C_2$haloalkoxy, or optionally substituted phenyl;

$R^3$ is hydrogen;

$R^4$ is methyl ethyl, n-propyl, vinyl, ethynyl or methoxy; and $R^5$, $R^6$, $R^7$, $R^8$ and $R^9$ are independently hydrogen, halogen, $C_1$-$C_4$alkyl, $C_1$-$C_4$haloalkyl, $C_1$-$C_4$alkoxy, $C_1$-$C_4$haloalkoxy, $C_2$-$C_4$alkenyl, $C_2$-$C_4$haloalkenyl, $C_2$-$C_4$alkynyl;

$R^6$ and $R^7$ or $R^8$ and $R^9$ together with the carbon atoms to which they are attached form an optionally substituted carbocyclic ring or an optionally substituted heterocyclyl; or $R^5$ and $R^6$ together form a bond; and HetAr is heteroaryl or heteroaryl substituted one to three times by fluoro, chloro, bromo, methyl, methoxy, cyano or trifluoromethyl.

3. A compound according to claim 2, wherein $R^1$ is methyl or ethyl, $R^2$ is methyl or chloro, $R^3$ is hydrogen, and $R^4$ is methyl, ethyl or methoxy, and $R^5$, $R^6$, $R^7$, $R^8$ and $R^9$ are hydrogen, or $R^5$ and $R^6$ together form a bond; and
HetAr is a 5- or 6-membered heteroaryl or is a 5- or 6-membered heteroaryl which is substituted one to three times by fluoro, chloro, bromo, methyl, methoxy, cyano or trifluoromethyl.

4. A compound according to claim 3, wherein the HetAr moieties contain 1 or 2 nitrogen, oxygen or sulphur atoms.

5. A compound according to claim 4, wherein HetAr is thienyl, furyl, oxazolyl, isoxazolyl, benzofuryl, thiazolyl, oxazolyl, isothiazolyl, benzothienyl, benzoisothienyl, benzothiazolyl, benzisothiazolyl, benzoxazolyl or benzisoxazolyl, where these rings are optionally substituted one or two times by fluoro, chloro, bromo, methyl, methoxy, cyano or trifluoromethyl.

6. A compound according to claim 4, wherein HetAr is pyridyl, pyrimidinyl, pyridazinyl, quinolinyl, isoquinolinyl, cinnolinyl, phthalazinyl, quinazolinyl or quinoxalinyl, where these rings are optionally substituted one or two times by fluoro, chloro, bromo, methyl, methoxy, cyano or trifluoromethyl.

7. A compound according to claim 1, wherein $R^1$ is methyl, ethyl, n-propyl, cyclopropyl, halogen or $C_1$-$C_2$ haloalkoxy, $R^2$ is hydrogen, $R^3$ is phenyl or pyridyl, where these rings are optionally substituted one to three times by fluoro, chloro, bromo, methyl, methoxy, cyano or trifluoromethyl, and $R^4$ is hydrogen.

8. A compound according to claim 1, wherein "heteroaryl" means pyridyl, pyrimidinyl, pyridazinyl, pyrazinyl, quinolinyl, isoquinolinyl, cinnolinyl, phthalazinyl, quinazolinyl, quinoxalinyl, naphthyridinyl, or pteridinyl.

9. A compound according to claim 1, wherein "heteroaryl" means:
a 6-membered heteroaryl ring which is optionally benzannellated, optionally substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

10. A compound according to claim 1, wherein G is hydrogen.

11. A compound according to claim 1, wherein, when G is a latentiating group, then G is a group —C($X^a$)—$R^a$ or —C($X^b$)—$X^c$—$R^b$, and the meanings of $X^a$, $R^a$, $X^b$, $X^c$ and $R^b$ are as defined in claim 1.

12. A herbicidal composition, which, in addition to comprising formulation adjuvants, comprises a herbicidally effective amount of a compound of formula I as defined in claim 1.

13. A herbicidal composition according to claim 12, which, in addition to comprising formulation adjuvants, comprises a herbicidally effective amount of the compound of formula I, a further herbicide, and optionally a safener.

14. A herbicidal composition according to claim 12, which, in addition to comprising formulation adjuvants, comprises a herbicidally effective amount of the compound of formula I, a safener, and optionally a further herbicide.

15. A mixture of a compound of formula I, as defined in claim 1, in combination with a further herbicide, wherein the mixture of the compound of formula I is selected from:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl) phenoxy]-2-pyridyloxy]acetic acid ethyl ester, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid, compound of formula I+BAY747 which has Chemical Abstracts Service Reference Number 335104-84-2, compound of formula I+topramezone, compound of formula I+4-hydroxy-3-[[2-[(2-methoxyethoxy)methyl]-6-(trifluoromethyl)-3-pyridinyl]carbonyl]bicyclo [3.2.1]oct-3-en-2-one, and compound of formula I+4-hydroxy-3-[[2-(3-methoxypropyl)-6-(difluoromethyl)-3-pyridinyl]carbonyl]-bicyclo[3.2.1]oct-3-en-2-one;

and wherein the mixture partner for the compound of formula I is optionally in the form of an ester or a salt.

16. A method of controlling grasses and weeds in crops of useful plants, which comprises applying a herbicidally effective amount of a compound of formula I as defined in claim 1, or of a composition comprising such a compound, to the plants or to the locus thereof.

17. A method according to claim 16, which is a method of controlling grasses and weeds in crops of useful plants, which comprises applying a herbicidally effective amount of a composition comprising the compound of formula I to the plants or to the locus thereof, and wherein the crops of useful plants are cereals, rice, corn, rape, sugarbeet, sugarcane, soybean, cotton, sunflower, peanut or plantation crops.

18. A method according to claim 17, wherein the crops of useful plants are wheat or barley.

* * * * *